(12) United States Patent
Lee et al.

(10) Patent No.: US 11,078,487 B2
(45) Date of Patent: Aug. 3, 2021

(54) CANCER-SPECIFIC TRANS-SPLICING RIBOZYMES AND USE THEREOF

(71) Applicants: Rznomics Inc., Gwangju (KR); Dong-A University Research Foundation for Industry Academy Cooperation, Busan (KR); Industry-Academic Cooperation Foundation, Dankook University, Yongin-si (KR)

(72) Inventors: Seong-Wook Lee, Seoul (KR); Chang Ho Lee, Yongin-si (KR); Seung Ryul I Han, Yongin-si (KR); Ji Hyun Kim, Seoul (KR); Eun Yi Cho, Yongin-si (KR); Jin Sook Jeong, Busan (KR); Mi Ha Ju, Busan (KR)

(73) Assignees: Rznomics Inc., Gwangju (KR); Dong-A University Research Foundation for Industry Academy Cooperation, Busan (KR); Industry-Academic Cooperation Foundation, Dankook University, Yongin-si (KR)

( * ) Notice: Subject to any disclaimer, the term of this patent is extended or adjusted under 35 U.S.C. 154(b) by 0 days.

(21) Appl. No.: 16/797,663

(22) Filed: Feb. 21, 2020

(65) Prior Publication Data
US 2020/0270612 A1     Aug. 27, 2020

(30) Foreign Application Priority Data
Feb. 22, 2019  (KR) .................... 10-2019-0021191
Feb. 20, 2020  (KR) .................... 10-2020-0021014

(51) Int. Cl.
*C07H 21/04*     (2006.01)
*C12N 15/113*    (2010.01)
*A61P 35/00*     (2006.01)
*C12N 15/86*     (2006.01)
*A61K 9/00*      (2006.01)

(52) U.S. Cl.
CPC .......... *C12N 15/1135* (2013.01); *A61P 35/00* (2018.01); *C12N 15/113* (2013.01); *C12N 15/86* (2013.01); *A61K 9/0019* (2013.01); *C12N 2310/141* (2013.01); *C12N 2710/10343* (2013.01)

(58) Field of Classification Search
None
See application file for complete search history.

(56) References Cited

U.S. PATENT DOCUMENTS 10,039,841 B2 *   8/2018   Kim ............... C12Y 305/04001
10,280,420 B2     5/2019   Lee et al.

FOREIGN PATENT DOCUMENTS

KR   10-2016-0038674 A    4/2016
WO      2016/052851 A1    4/2016

OTHER PUBLICATIONS

Kwon, Byung-Su, et al. "Intracellular efficacy of tumor-targeting group I intron-based trans-splicing ribozyme." The journal of gene medicine 13.2 (2011): 89-100.*

* cited by examiner

*Primary Examiner* — Kimberly Chong
(74) *Attorney, Agent, or Firm* — Sughrue Mion, PLLC

(57) ABSTRACT

A cancer-specific trans-splicing ribozyme and a use thereof are disclosed. The trans-splicing ribozyme does not act on normal tissue, but is specifically expressed in cancer tissue. Therefore, it is very safe and has excellent expression efficiency at the post-transcription level, and thus can be effectively used in treatment of cancer.

17 Claims, 45 Drawing Sheets
Specification includes a Sequence Listing.

CANCER-SPECIFIC TRANS-SPLICING RIBOZYMES AND USE THEREOF

CROSS-REFERENCE TO RELATED APPLICATION

This application claims priority to and the benefit of Korean Patent Application No. 2019-0021191, filed on Feb. 22, 2019, and Korean Patent Application No. 2020-0021014, filed on Feb. 20, 2020, each of which is incorporated herein by way of reference in its entirety.

FIELD OF THE INVENTION

An embodiment of the invention relates to a cancer-specific trans-splicing ribozyme and a use thereof.

DISCUSSION OF RELATED ART

Telomerase is a ribonucleoprotein, which enables immortal proliferation of cells by reversing a shortening region of telomere during DNA replication by repeatedly adding a TTAGGG sequence to the end of a telomere present at the 3' end of a chromosome. Telomerase is one of the most important enzymes among those regulating the immortalization and proliferation ability of cancer cells. While hematopoietic cells and about 80 to 90% of cancer cells possess telomerase activity, normal cells neighboring cancer cells do not exhibit the activity. Moreover, telomerase reactivation has a major effect on immortal growths of advanced metastatic cancer.

Human telomerase consists of two components including human telomerase RNA (hTR), which acts as substrate RNA and human telomerase reverse transcriptase (hTERT) which serves as a catalyst. hTERT genes are expressed in proportion to telomerase activity, and there is a strong correlation between an intracellular hTERT level and cellular telomerase activity. Particularly, TERT activity can be observed in about 90% or more of cancer patients.

Recently, trans-splicing ribozymes targeting the hTERT has been reported, and its possible use as a cancer therapeutic agent has been investigated. However, while a combination of a trans-splicing ribozyme and a tissue-specific promoter shows a high tissue specificity, their expression efficiency is very low, making its use for therapeutic purpose as unsatisfactory. In addition, since telomerase is also active in certain normal cells such as stem cells, hematopoietic stem cells, germ cells, and regenerating normal hepatocytes, hTERT-targeting treatment can have toxic effects towards these normal cells. It is reported that about 5% of normal hepatocytes possess weak telomerase activity, and the telomerase activity increases in regenerating liver. Particularly, a majority of hepatocellular carcinoma (HCC) is accompanied by liver cirrhosis, and non-tumorous hepatocytes in a regenerative nodule in the liver cirrhosis region exhibit TERT expression at a low level.

Korean Patent Application Publication No. 10-2016-0038674 A, describes a recombinant vector which includes (i) a ribozyme-target gene expression cassette that includes a tissue-specific promoter, a trans-splicing ribozyme targeting a cancer-specific gene, and a target gene connected to the 3' exon of the ribozyme, and (ii) additionally a nucleic acid sequence recognizing microRNA-122 (miR-122). It also describes a use of the ribozyme expressed therefrom for preventing or treating liver cancer. MiR-122 is microRNA known to be very highly expressed in a normal liver, but less expressed in advanced liver cancer cells. According to prior art, based on the above-mentioned phenomenon, as a miR-122 targeting region is introduced to the 3' UTR region of a ribozyme expression vector, a ribozyme delivered to the liver is not expressed in a normal liver due to overexpressed miR-122 but is expressed in liver cancer cells having a decreased miR-122 level.

However, the above-discussed conventional approach has a drawback that a high count of vector-introduced viruses is needed to exhibit a therapeutic effect. In addition, it has been reported that an increased expression of miR-122 was found frequently in a liver tissue with cancer caused by hepatitis C virus (HCV) infection, compared to a normal liver tissue. For this reason, effectiveness of the above discussed conventional approach to treat liver cancer where the expression of miR-122 increases or other cancers is questionable.

SUMMARY OF THE INVENTION

To solve the above-described problem, an embodiment of the invention is directed to providing a cancer-specific trans-splicing ribozyme possessing an excellent safety and expression efficiency, suitable for treating cancer.

An embodiment of the invention provides a nucleic acid construct comprising, in this order from 5' end to 3' end:

(i) a cytomegalovirus (CMV) promoter;

(ii) a ribozyme-desired gene expression cassette, which includes (a) a sequence encoding a trans-splicing ribozyme targeting a cancer-specific gene and (b) a desired gene connected to a 3' exon of the ribozyme-encoding sequence, in which the expression cassette has a splicing donor/splicing acceptor sequence (SD/SA sequence) connected to the 5' end of the ribozyme-desired gene expression cassette, and a Woodchuck hepatitis virus posttranscriptional regulatory element (WPRE) connected to the 3' end of the ribozyme-desired gene expression cassette; and (iii) a nucleic acid sequence recognizing microRNA-122 (miR-122), which is connected to the 3' end of the WPRE.

In addition, an embodiment of the invention provides a gene delivery system, which includes the nucleic acid construct.

Moreover, an embodiment of the invention provides a ribozyme expressed from the nucleic acid construct.

Furthermore, an embodiment of the invention provides a pharmaceutical composition for preventing or treating cancer, which includes the nucleic acid construct, a gene delivery system or a ribozyme as an active ingredient.

BRIEF DESCRIPTION OF THE DRAWINGS

The above disclosure and other objects, features and advantages of an embodiment of the invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
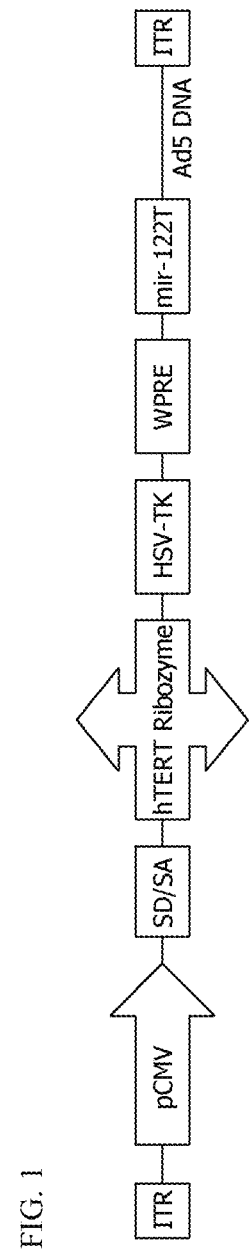
FIG. 1 is a schematic diagram of the configuration of an expression cassette for a CMV promoter-based hTERT-targeting trans-splicing ribozyme and a target gene according to an embodiment of the invention.

Hereinafter, an embodiment of the invention will be described in further detail.

In an embodiment of the invention, when a part "includes" one component, it means that, unless particularly stated otherwise, another component may be further included, not excluding the relevant component.

Nucleic Acid Construct

One aspect of the invention provides a nucleic acid construct, comprising, in this order from 5' end to 3' end:

(i) a cytomegalovirus (CMV) promoter;

(ii) a ribozyme-desired gene expression cassette, which includes a trans-splicing ribozyme encoding sequence and a desired gene connected to a 3' exon of the ribozyme, said ribozyme targeting a cancer specific gene, in which the expression cassette has a SD/SA sequence connected to the 5' end of the ribozyme-desired gene expression cassette, and WPRE connected to the 3' end of the ribozyme-desired gene expression cassette; and (iii) an additional nucleic acid sequence recognizing microRNA-122 (miR-122), which is connected to the 3' end of the WPRE.

Based on the findings that a nucleic acid construct has an excellent cancer treating effect in vivo when including a cytomegalovirus (CMV) promoter, a ribozyme encoding sequence, a SD/SA sequence and WPRE, which is connected at both ends of a desired gene, as constituents, and as the nucleic acid construct employs a CMV promoter, a SD/SA sequence and WPRE at the same time and further includes a nucleic acid sequence recognizing miR-122, various cancer cells as well as liver cancer cells can be killed.

The term "vector" used herein is an expression vector capable of expressing a target gene within suitable host cells and a gene construct including an essential regulatory element operably linked in order to express a gene insert included in the vector.

The term "operably linked" used herein refers to a functional linkage between a nucleic acid expression regulating sequence performing a general function and a nucleic acid sequence encoding a target gene.

For example, when a ribozyme-encoding sequence is operably linked to a promoter, the expression of the ribozyme-encoding sequence will be under the influence or control of the promoter. Two nucleic acid sequences (the ribozyme-encoding sequence and a promoter region sequence at the 5' end of the ribozyme-encoding sequence) are operably linked when promoter activity is induced and the ribozyme-encoding sequence is then transcribed, and it may be considered that the two nucleic acid sequences are operably linked when the linkage properties between the two sequences do not induce a frame shift mutation, and the expression regulating sequence does not inhibit ribozyme expression. The operable linkage to the nucleic acid construct may be formed using a gene recombination technique well known in the art, and site-specific DNA cleavage and linkage may use an enzyme generally known in the art.

The vector according to an embodiment of the invention may include a signal sequence or leader sequence for membrane targeting or secretion as well as expression regulatory factors such as a promoter, an operator, an initiation codon, a termination codon, a polyadenylation signal and an enhancer, and may be manufactured in various ways according to an intended purpose. A promoter of the vector may be a constitutive or inducible promoter. In addition, the expression vector may include a selectable marker for selecting host cells containing a vector, and in the case of a replicable expression vector, an origin of replication may be included. The vector may be self-replicated or integrated into host DNA.

The vector according to an embodiment of the invention is preferably a plasmid vector, a cosmid vector or a virus vector, and most preferably, a virus vector. The virus vector is preferably derived from a retrovirus, such as human immunodeficiency virus (HIV), murine leukemia virus (MLU), avian sarcoma/leucosis virus (ASLV), spleen necrosis virus (SNV), Rous sarcoma virus (RSV) or mouse mammary tumor virus (MMTV), an adenovirus, an adeno-associated virus (AAV), or a herpes simplex virus (HSV), but an embodiment of the invention is not limited thereto. The nucleic acid construct according to an embodiment of the invention is most preferably a recombinant adenovirus vector.

The term "expression cassette" used herein means a unit cassette capable of expressing a trans-splicing ribozyme-desired gene, which includes a CMV promoter, a SD/SA sequence, a WPRE sequence, a trans-splicing ribozyme-desired gene and a nucleic acid sequence recognizing miR-122. The trans-splicing ribozyme-desired gene is located between the SD/SA sequence and the WPRE sequence, and the nucleic acid sequence recognizing miR-122 is connected to the 3' end of the WPRE.

The trans-splicing ribozyme-desired gene expression cassette according to an embodiment of the invention may further include an expression regulation inducer to regulate a transcription level and a posttranscriptional level of the ribozyme-desired gene. In an embodiment of the invention, particularly, a SD/SA sequence and/or WPRE is(are) linked, and a sequence recognizing miR-122 is further linked to the 3' end of the WPRE, but an embodiment of the invention is not limited thereto. Due to the SD/SA sequence, the WPRE and the sequence recognizing miR-122, an expression level of the ribozyme-desired gene may be regulated, and the ribozyme is expressed only when miR-122 is expressed at a certain level or less, such that the influence on normal hepatocytes may be minimized.

In the ribozyme-desired gene expression cassette according to an embodiment of the invention, preferably, a SD/SA sequence (SD/SA) is linked to the 5' end of the ribozyme encoding sequence, WPRE is linked to the 3' end of the desired gene, and a sequence recognizing miR-122 is linked to the 3' end of the WPRE.

The SD/SA sequence according to an embodiment of the invention may increase transcription initiation, processing of RNA polymerase II and the nucleocytoplasmic export of mRNA, and the WPRE according to an embodiment of the invention may increase processing and nucleocytoplasmic export of mRNA, and thus the pre-mRNA level may increase. Due to the configuration described above, the RNA level of a ribozyme in cells is significantly increased to allow the death of cancer cells in vivo to increase and allow cancer cell-specific expression, resulting in the reduction in toxicity towards normal cells.

The SD/SA sequence according to an embodiment of the invention is a sequence corresponding to the starting region/ending region of an intron cleaved by splicing to remove an intron of a RNA transcript, and generally, the SD sequence may be a GU sequence at the 5' end of the intron, and the SA sequence may be an AG sequence at the 3' end of the intron.

The WPRE according to an embodiment of the invention refers to a sequence increasing gene expression as a result of inducing a tertiary structure that promotes transcription in DNA.

In an embodiment of the invention, the SD/SA sequence and WPRE sequence may include sequences of SEQ ID NO: 6 and SEQ ID NO: 7, respectively, but are not limited as long as they are present in the desired gene expression cassette and promote the expression of a desired gene.

The nucleic acid sequence recognizing miR-122 according to an embodiment of the invention is called a microRNA-122 target site (miR-122T) in the specification. The miR-122T may include one or more, for example, 1 to 10, preferably, 1 to 5, and more preferably, 1 to 3 sequences of SEQ ID NO: 5. The miR-122 is normally expressed in normal hepatocytes, but an expression level thereof is reduced in liver cancer cells. A therapeutic agent with increased sensitivity and specificity towards liver cancer cells may be developed using the miR-122T, and in an embodiment of the invention, a liver cancer cell-specific ribozyme may be expressed by including a nucleic acid sequence recognizing miR-122 to the ribozyme-encoding gene-desired gene expression cassette.

In one embodiment of the invention, when SD/SA and WPRE are included in the expression cassette, ribozyme expression increases and thus an effect of inducing cell death further increases. In addition, miR-122T targeting miR-122 induces cell death only in liver cancer cells in which miR-122 expression decreases and minimizes inducing cell death in normal hepatocytes in which the miR-122 expression is normally performed, and thus it was confirmed that liver cancer cell-specific treatment is possible (FIG. 2).

The term "cancer-specific gene" used herein refers to a gene specifically expressed or significantly over-expressed only in cancer cells. The cancer-specific gene may impart a characteristic by which the ribozyme according to an embodiment of the invention may act cancer-specifically. Such a cancer-specific gene has preferably a telomerase reverse transcriptase (TERT) mRNA sequence, an alphafetoprotein (AFP) mRNA sequence, a carcinoembryonic antigen (CEA) mRNA sequence, a prostate-specific antigen (PSA) mRNA sequence, a cytoskeleton-associated protein 2 (CKAP2) mRNA sequence or a mutant rat sarcoma (RAS) mRNA sequence, more preferably, a telomerase reverse transcriptase (TERT) mRNA sequence, and most preferably, a human telomerase reverse transcriptase (hTERT) mRNA sequence.

The term "TERT" used herein is one of important enzymes regulating immortality and a proliferation of cancer cells, and it refers to an enzyme serving to protect a chromosomal end by forming a telomere structure on a chromosome, thereby inhibiting cell aging. In normal cells, the telomere length gradually decreases every time the cells divide, resulting in the loss of genetic material and cell death. However, in cancer cells, since such an enzyme allows the telomere to extend continuously, the cells do not die, and the enzyme directly contributes to the immortality of cancer cells and thus is known as a critical obstacle in treating cancer. In an embodiment of the invention, hTERT mRNA including a sequence of SEQ ID NO: 2 may be used as a cancer-specific gene, but an embodiment of the invention is not limited thereto.

The term "promoter" used herein is a part of DNA, which is involved in binding of an RNA polymerase in order to initiate transcription. Generally, the promoter is located adjacent to a desired gene as well as at an upper region thereof, and as a site to which a transcription factor which is an RNA polymerase or a protein inducing an RNA polymerase binds, the enzyme or protein can be induced to be located at a proper transcription start region. That is, the promoter includes a specific gene sequence which is located at the 5' region of a gene to be transcribed in a sense strand and induces the initiation of mRNA synthesis for a desired gene when an RNA polymerase binds to a corresponding site directly or via a transcription factor.

The promoter according to an embodiment of the invention includes preferably a CMV promoter including a sequence of SEQ ID NO: 1 to increase the expression of a gene.

Figure 3A:
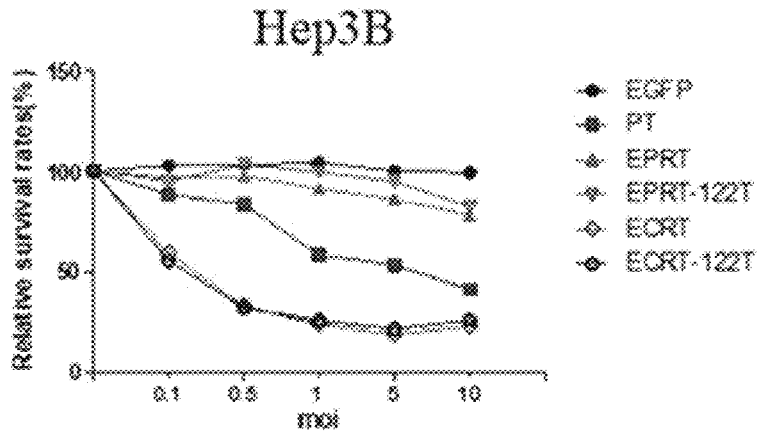
FIG. 3(a) is a graph showing cell survival rates according to the MOI of ECRT-122T adenovirus transduced into a Hep3B cell line not expressing miR-122.
Figure 3B:
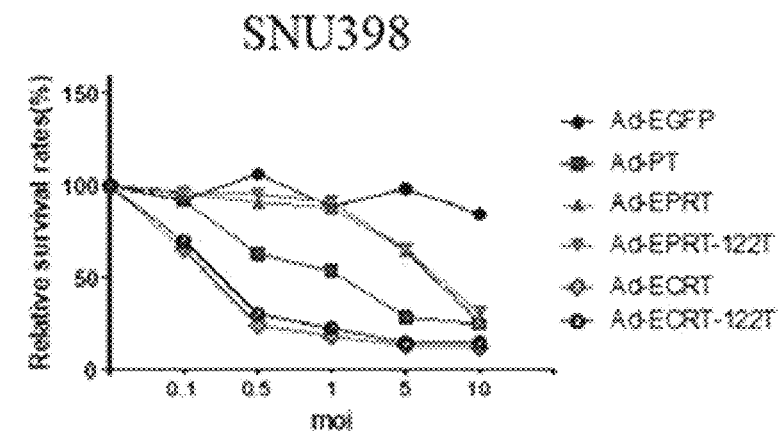
FIG. 3(b) is a graph showing cell survival rates according to the MOI of ECRT-122T adenovirus transduced into a SNU398 cell line not expressing miR-122.
Figure 3C:
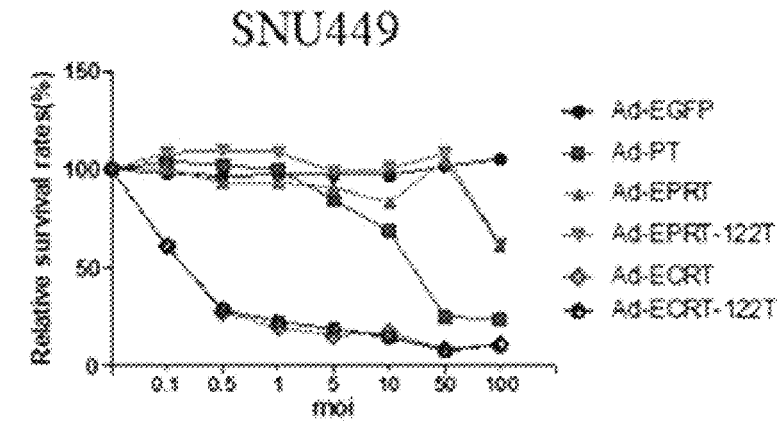
FIG. 3(c) is a graph showing cell survival rates according to the MOI of ECRT-122T adenovirus transduced into a SNU449 cell line not expressing miR-122.

In one embodiment of the invention, it was confirmed that when a CMV promoter is introduced into the nucleic acid construct according to an embodiment of the invention, excellent ribozyme expression efficiency is achieved, and despite of existence of regulation by miR-122 due to the miR-122T contained in the nucleic acid construct, the high expression of ribozyme induces cell death and exhibits an anticancer effect (FIGS. 3 and 4).

The term "ribozyme" used herein is an RNA molecule acting as an enzyme or a complex molecule comprising the RNA molecule, and it is also called an RNA enzyme or catalytic RNA. The ribozyme is an RNA molecule having a three-dimensional structure, which performs a chemical reaction and has a property of self-clearing or cleaving a target RNA. It is known that some ribozymes cleave themselves or a target RNA molecule to inhibit activity of the target RNA and that other ribozymes catalyze the aminotransferase activity of a ribosome. Such ribozymes may include a hammerhead ribozyme, a VS ribozyme and a hairpin ribozyme.

The ribozyme according to an embodiment of the invention may not only exhibit a selective anticancer effect by inhibiting the activity of a cancer-specific gene through a trans-splicing reaction, but also activate an anti-cancer therapeutic gene which can be target-specifically co-expressed. Accordingly, any type of ribozyme can be used as long as it can inactivate a cancer-specific gene and activate an anti-cancer therapeutic gene.

The ribozyme according to an embodiment of the invention is preferably a ribozyme targeting the hTERT mRNA described above, and may inhibit expression of hTERT by specifically cleaving hTERT mRNA in a cancer cell overexpressing hTERT and may specifically serve to express a therapeutic gene.

The term "trans-splicing" used herein refers to linking RNAs derived from different genes to each other. Preferably, an hTERT-targeting trans-splicing group I ribozyme whose trans-splicing ability is verified as a result of recognizing mRNA of cancer-specific hTERT may be used.

The term "desired gene" used herein refers to a gene to be linked to an mRNA of a cancer-specific gene by a trans-ligation action of the ribozyme and be induced to be expressed.

The desired gene according to an embodiment of the invention is preferably an anti-cancer therapeutic gene or a reporter gene, and most preferably, an anti-cancer therapeutic gene.

The term "anti-cancer therapeutic gene" used herein refers to a polynucleotide sequence encoding a polypeptide exhibiting a therapeutic effect in regards to the expression in cancer cells. The anti-cancer therapeutic gene may be expressed while being conjugated with the ribozyme, or independently expressed, thereby exhibiting anticancer activity. The anti-cancer therapeutic gene is preferably one or more selected from the group consisting of a drug-sensitizing gene, a proapoptotic gene, a cytostatic gene, a cytotoxic gene, a tumor suppressor gene, an antigenic gene, a cytokine gene and an anti-angiogenic gene, and most preferably, a drug-sensitizing gene.

In an embodiment of the invention, one or more anti-cancer therapeutic genes may be used individually or in combination.

The drug-sensitizing gene according to an embodiment of the invention is a gene encoding an enzyme that converts a non-toxic prodrug into a toxic material, and since cells into which the gene is introduced die, it is also called a suicide gene. That is, when a non-toxic prodrug is systemically administered to normal cells, the prodrug is converted into a toxic metabolite only in cancer cells to change sensitization to a drug, resulting in the destruction of cancer cells. Such a drug-sensitizing gene is preferably a herpes simplex virus-thymidine kinase (HSVtk) gene using ganciclovir as a prodrug, or a cytosine deaminase (CD) gene of E. coli using 5-fluorocytosine (5-FC) as a prodrug, and most preferably, a HSVtk gene including a sequence of SEQ ID NO: 4.

The proapoptotic gene according to an embodiment of the invention refers to a nucleotide sequence inducing programmed apoptosis when expressed. Examples of proapoptotic genes known to those of ordinary skill in the art may include a p53 gene, an adenovirus E3-11.6K gene (derived from Ad2 and Ad5), an adenovirus E3-10.5K gene (derived from Ad), an adenovirus E4 gene, a p53 pathway gene and a gene encoding a caspase.

The cytostatic gene according to an embodiment of the invention refers to a nucleotide sequence expressed in cells to suspend a cell cycle during the cell cycle. Examples of the cytostatic genes include a p21 gene, a retinoblastoma gene, an E2F-Rb fusion protein gene, genes encoding a cyclin-dependent kinase inhibitor (e.g., p16, p15, p18 and p19) and a growth arrest specific homeobox (GAX) gene, but an embodiment of the invention is not limited thereto.

The cytotoxic gene according to an embodiment of the invention refers to a nucleotide sequence expressed in cells to exhibit toxicity. For example, the cytotoxic gene includes a nucleotide sequence encoding a *Pseudomonas* exotoxin, a lysine toxin or a Diphtheriae toxin, but an embodiment of the invention is not limited thereto.

The tumor suppressor gene according to an embodiment of the invention refers to a nucleotide sequence which may be expressed in target cells to suppress a tumor phenotype or induce cell death. As a representative example, the tumor suppressor gene may be a tumor necrosis factor-α (TNF-α) gene, a p53 gene, an APC gene, a DPC-4/Smad4 gene, a BRCA-1 gene, a BRCA-2 gene, a WT-1 gene, a retinoblastoma gene, an MMAC-1 gene, an adenomatous polyposis coil protein, a deleted colon carcinoma (DCC) gene, an MMSC-2 gene, an NF-1 gene, a nasopharyngeal tumor suppressor gene located on chromosome 3p21.3, an MTS1 gene, a CDK4 gene, an NF-1 gene, an NF-2 gene, a VHL gene or a programmed death-1 (sPD-1) gene.

The antigenic gene according to an embodiment of the invention refers to a nucleotide sequence that is expressed in target cells to produce a cell surface antigenic protein recognized by the immune system. As examples of the antigenic gene known to those of ordinary skill in the art, the antigenic gene may include a carcinoembryonic antigen (CEA) and p53.

The cytokine gene according to an embodiment of the invention refers to a nucleotide sequence that is expressed in cells to produce a cytokine. Representative examples of the cytokine genes may include GMCSF, interleukins (IL-1, IL-2, IL-4, IL-12, IL-10, IL-19, and IL-20), interferons α, β and γ (interferon α-2b) and fusions such as interferon α-2α-1.

The anti-angiogenic gene according to an embodiment of the invention refers to a nucleotide sequence that is expressed to release an anti-angiogenic factor out of cells. Examples of the anti-angiogenic genes may include angiostatin, a vascular endothelial growth factor (VEGF) suppressor, and endostatin.

The term "herpes simplex virus-thymidine kinase (HSV-tk)" used herein refers to a thymidine kinase derived from a herpes simplex virus. This enzyme is a representative example of a drug-sensitizing gene that converts a non-toxic prodrug into a toxic material, leading to death of the gene-inserted cells. In an embodiment of the invention, the HSV-tk gene may be used as an anti-cancer therapeutic gene that is expressed as a conjugate with the ribozyme according to an embodiment of the invention and exhibits anticancer activity. The HSVtk gene may be exemplified by GenBank Accession No. AAP13943, P03176, AAA45811, P04407, Q9QNF7, KIBET3, P17402, P06478, P06479, AAB30917, P08333, BAB84107, AAP13885, AAL73990, AAG40842, BAB11942, NP 044624, NP 044492, or CAB06747.

The term "reporter gene" used herein is a gene used to monitor whether a nucleic acid construct according to an example of an embodiment of the invention is introduced or to monitor expression efficiency of a ribozyme, and may be any gene that enables monitoring without damage to infected cells or tissue without limitation. Preferably, the reporter gene is luciferase, a green fluorescent protein (GFP), a modified green fluorescent protein (mGFP), an enhanced green fluorescent protein (EGFP), a red fluorescent protein (RFP), a modified red fluorescent protein (mRFP), an enhanced red fluorescent protein (ERFP), a blue fluorescent protein (BFP), an enhanced blue fluorescent protein (EBFP), a yellow fluorescent protein (YFP), an enhanced yellow fluorescent protein (EYFP), a cyan fluorescent protein (CFP) or an enhanced cyan fluorescent protein (ECFP).

The expression of a cancer cell-specific ribozyme may be observed by using a reporter gene as a desired gene. The ribozyme-expression vector of an embodiment of the invention includes a promoter and a miRNA target site, and therefore may specifically expressed in cancer cells, but not in normal cells. It will be apparent to those of ordinary skill in the art that the above-described method can be applied to diagnose whether cancer occurs in specific tissue.

Gene Delivery System

Another aspect of the invention provides a gene delivery system including the nucleic acid construct according to an embodiment of the invention.

The term "gene delivery system" used herein refers to a system that can increase expression efficiency by increasing intracellular delivery efficiency for a target gene and/or nucleic acid sequence, and may be classified into a virus-mediated system and a non-viral system.

The virus-mediated system uses a viral vector such as a retrovirus vector or an adenovirus vector, and is known to have relatively higher intracellular gene delivery efficiency than a non-viral system since it uses a virus's inherent cellular invasion mechanism that infects human cells. In addition, after entering cells, a non-viral vector has a drawback of gene degradations in an endolysosome after the endosome is fused with a lysosome, whereas a viral vector has an advantage of high gene delivery efficiency because of less gene loss thanks to a mechanism of delivering a gene into a nucleus without passing through a lysosome.

The viral vector that can be used in an embodiment of the invention may be a vector derived from a retrovirus, an adenovirus or an adeno-associated virus as described in the disclosure on the nucleic acid construct. The viral vector may be introduced into cells by a transduction method, such as infection, after assembly into a viral particle.

In one embodiment of the invention, a recombinant adenovirus including the above-described nucleic acid construct was designed as a gene delivery system. That is, the recombinant adenovirus serves to deliver a nucleic acid construct expressing a trans-splicing ribozyme specific to a cancer-specific gene to target cells (e.g., cancer cells), and the nucleic acid construct delivered into the cells is expressed by an intracellular transcription system. The expressed trans-splicing ribozyme may insert a desired gene-encoding RNA that is linked to the ribozyme into the cleaved transcript of the cancer-specific gene that is abundant in cancer cells.

The non-viral system is a method of using a cationic lipid delivery system or cationic polymer delivery system as a delivery vehicle for a nucleic acid and/or a gene, or a method of using electroporation.

A cationic lipid delivery system is a method of forming a complex using a positive charge of a nanometer-sized liposome mainly consisting of a cationic lipid or nanoparticles made of a lipid with a negatively charges gene, and an expression vector or nucleic acid containing the gene, and then delivering the complex into cells by endocytosis. The complex delivered into cells is first delivered to a lysosome from an endosome, exported through the cytoplasm and then expressed. A cationic polymer delivery system delivers a gene in a manner similar to the cationic lipid delivery system, except that a polymer is used instead of a lipid, and representative cationic polymers include polyethyleneimine, poly-L-lysine and chitosan.

Accordingly, the nucleic acid construct of an embodiment of the invention may be combined with a cationic lipid delivery system or cationic polymer delivery system, thereby forming a complex, and the resulting complex may be used as a gene delivery system.

In an embodiment of the invention, the gene delivery system may include the above-described nucleic acid construct, and may be one of a virus-mediated system and a non-viral system, and preferably, a virus-mediated system.

Ribozyme

Another aspect of the invention provides a ribozyme expressed from a nucleic acid construct according to an embodiment of the invention.

Descriptions of a nucleic acid construct or ribozyme according to an embodiment of the invention are as described above.

Pharmaceutical Composition

Yet another aspect of the invention provides a pharmaceutical composition for preventing or treating cancer, which includes a nucleic acid construct according to an embodiment of the invention, a gene delivery system including the nucleic acid construct, or a ribozyme as an active ingredient.

Descriptions of the nucleic acid construct, gene delivery system, or ribozyme according to an embodiment of the invention are as described above.

The term "cancer" used herein refers to a condition in which cells are abnormally over-proliferated due to problems occurring in the regulation of normal cell division, differentiation and death and infiltrate into surrounding tissue and organs, thereby forming lumps, and thus the original structures of the tissue or organ is destroyed or deformed.

The cancer according to an embodiment of the invention is preferably liver cancer, glioblastoma, bile duct cancer, lung cancer, pancreatic cancer, melanoma, bone cancer, breast cancer, colon cancer, stomach cancer, prostate cancer, leukemia, uterine cancer, ovarian cancer, lymphoma, or brain cancer, more preferably, liver cancer, glioblastoma, or bile duct cancer, and most preferably, liver cancer.

In addition, according to an embodiment of the invention, cancers preferably show the copy number (expression level) of miR-122 expressed therein less than 100 times the copy number of ribozymes expressed by the pharmaceutical composition in the cancer tissue.

Figure 8A:
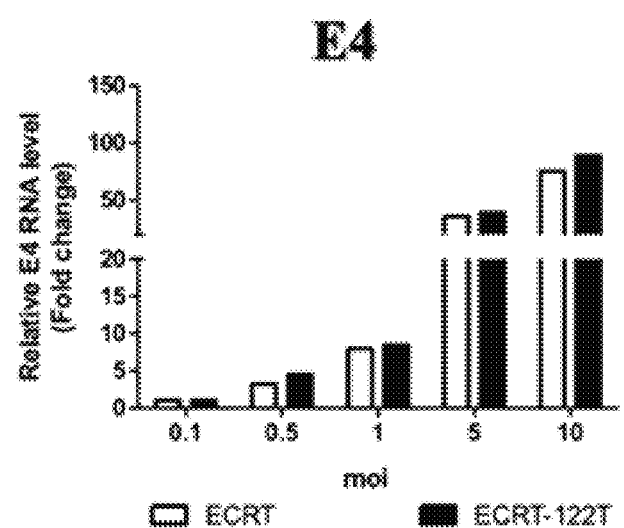
FIG. 8(a) is a graph showing RNA expression level of E4 according to the MOI of an ECRT-122T adenovirus transduced into Huh-7 cell lines expressing miR-122.
Figure 8B:
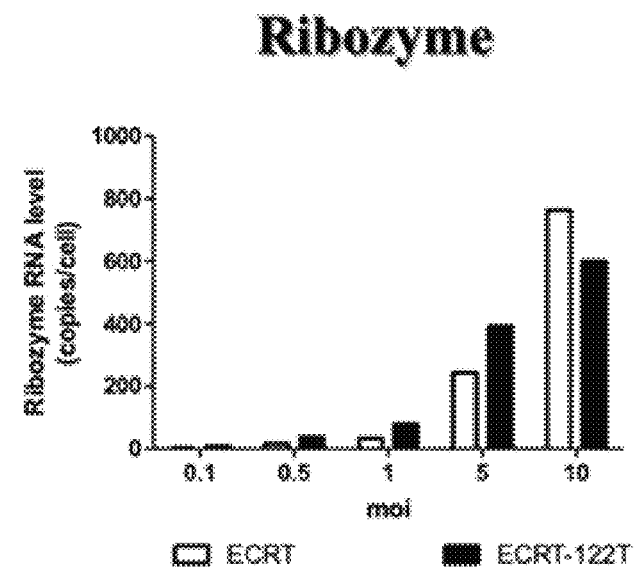
FIG. 8(b) is a graph showing RNA expression level of ribozyme according to the MOI of an ECRT-122T adenovirus transduced into Huh-7 cell lines expressing miR-122.
Figure 8C:
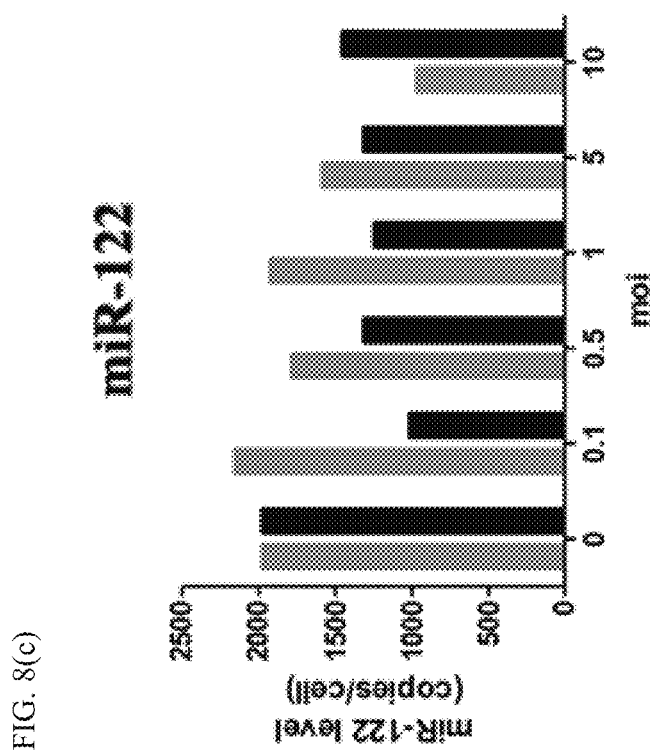
FIG. 8(c) is a graph showing RNA expression level of miR-122 according to the MOI of an ECRT-122T adenovirus transduced into Huh-7 cell lines expressing miR-122.
Figure 9A:
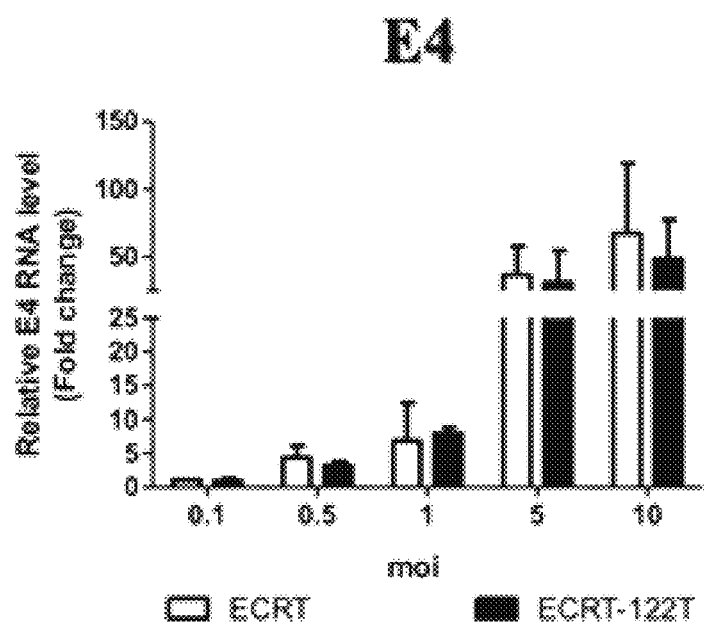
FIG. 9(a) is a graph showing RNA expression level of E4 according to the MOI of an ECRT-122T adenovirus transduced into Huh-7.5 cell lines expressing miR-122.
Figure 9B:
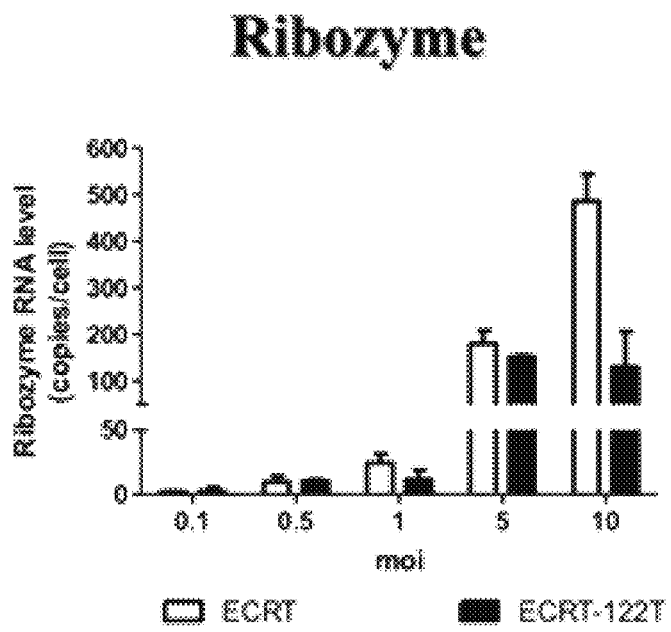
FIG. 9(b) is a graph showing RNA expression level of ribozyme according to the MOI of an ECRT-122T adenovirus transduced into Huh-7.5 cell lines expressing miR-122.

In an embodiment of the invention, as a result of observing the expression level of an hTERT-targeting ribozyme by the vector including miR-122T sequence in comparison with the expression level of miR-122 in cells, as the ratio of the miR-122 expression to the ribozyme expression increased, the ribozyme expression decreased and consequently a cell death-inducing effect also decreased (FIGS. 4, 8 and 9). Accordingly, the injection amount of a vector expressing a ribozyme may be determined by estimating the amount of the ribozyme that exhibits an anticancer effect according to the expression level of miR-122 in cancer tissue. Specifically, when the minimum copy number of miR-122 is approximately 100 times or higher the copy number of the ribozyme, the function (expression) of the ribozyme having a miR-122 target site is weakened, and when the copy number of miR-122 expressed in cancer tissue is less than 100 times the copy number of ribozymes expressed due to the pharmaceutical composition according to an embodiment of the invention in the cancer tissue, high anticancer efficacy can be achieved (FIG. 10).

In addition, the cancer according to an embodiment of the invention is preferably a cancer in which miR-122 is substantially not expressed in cancer tissue. The "cancer in which miR-122 is substantially not expressed in cancer tissue" refers to a cancer where miR-122 is expressed in a small copy number so that the miR-122 in cancer tissue does not exhibit a substantial effect on the function of a ribozyme having a miR-122 target site.

Figure 13:
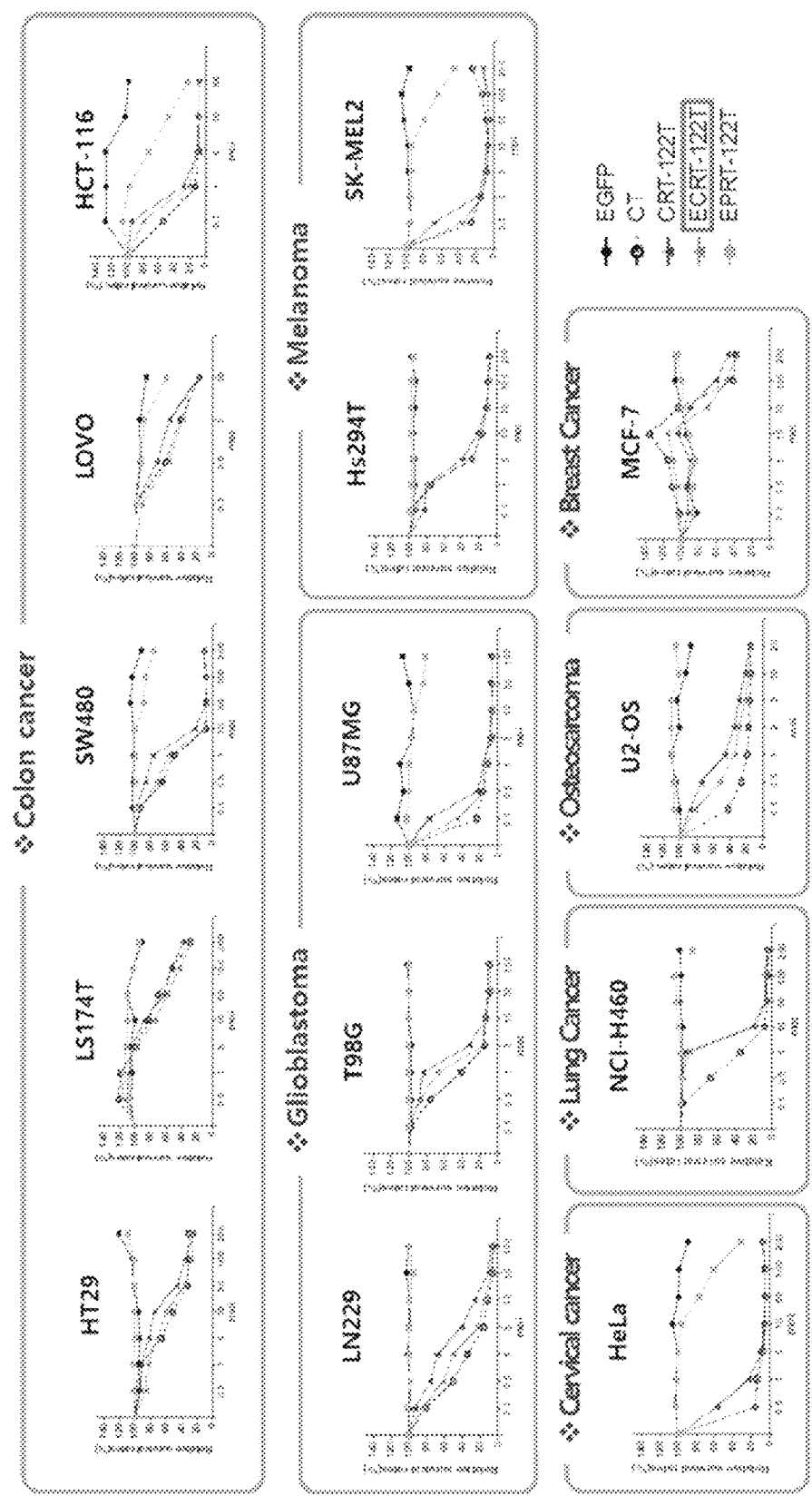
FIG. 13 is a set of graphs showing cell survival rates according to the MOI of ECRT-122T adenovirus transduced into a colon cancer cell line, a glioblastoma cell line, a melanoma cell line, a cervical cancer cell line, a lung cancer cell line, an osteosarcoma cell line and a breast cancer cell line.
Figure 14A:
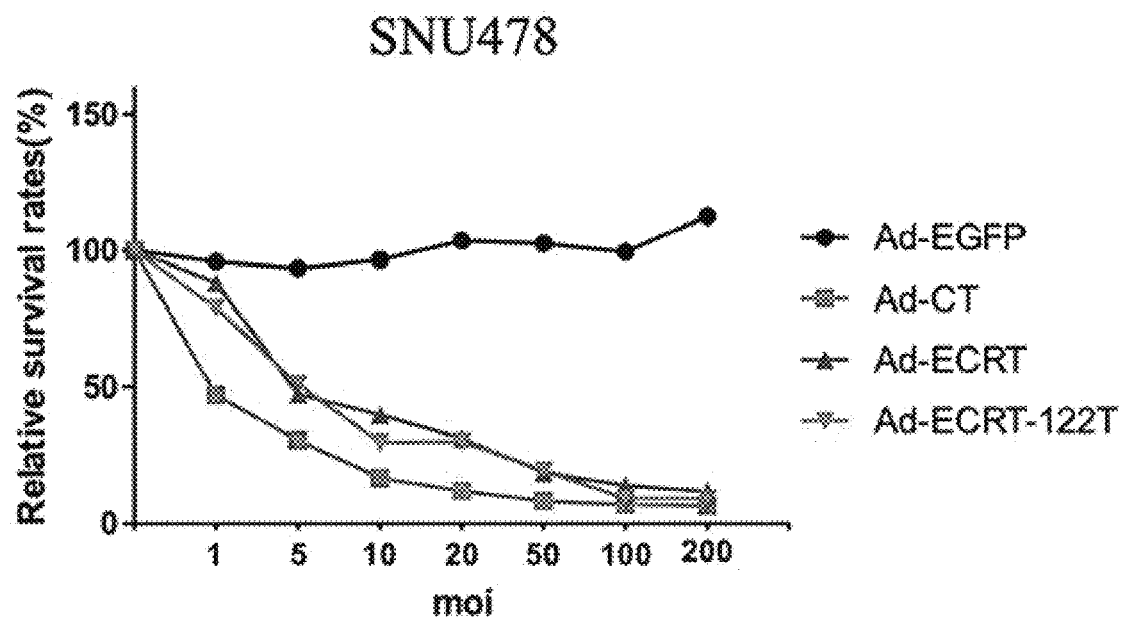
FIG. 14(a) is a graph showing cell survival rate according to the MOI of ECRT-122T adenovirus transduced into a SNU478 bile duct cancer cell line.
Figure 14B:
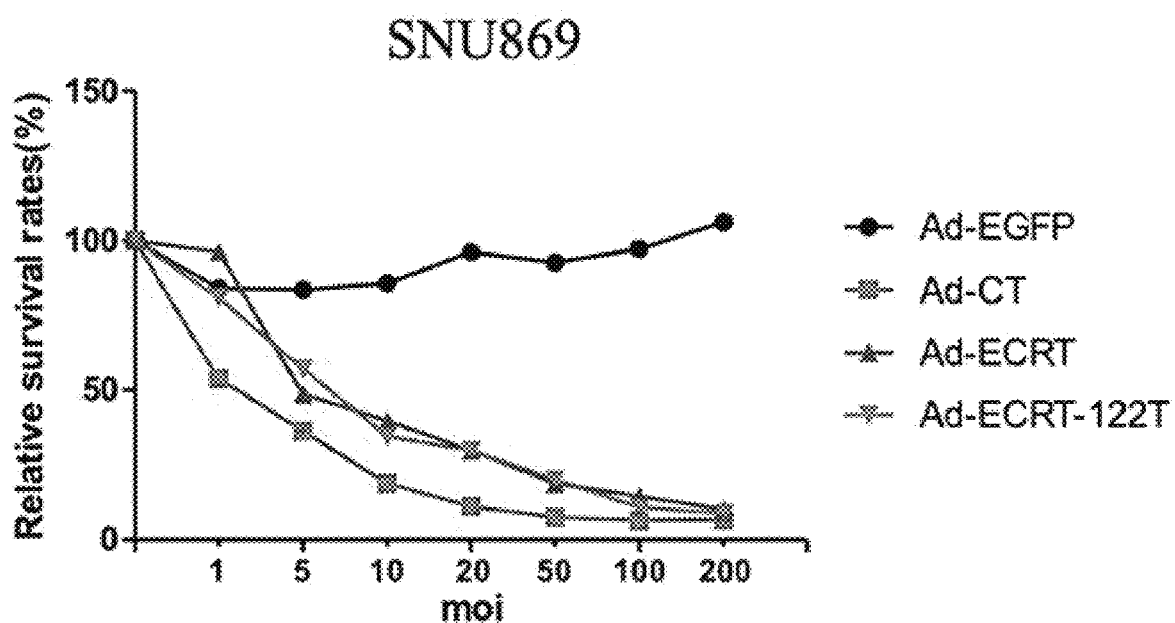
FIG. 14(b) is a graph showing cell survival rate according to the MOI of ECRT-122T adenovirus transduced into a SNU869 bile duct cancer cell line.

In one embodiment of an embodiment of the invention, in colon cancer, glioblastoma, melanoma, cervical cancer, lung cancer, osteosarcoma, breast cancer and bile duct cancer cell lines in which miR-122 is not substantially expressed in the cancer tissue, the anticancer efficacy of a ribozyme according to an embodiment of the invention was confirmed (FIGS. 13 and 14).

In addition, liver cancer according to an embodiment of the invention is preferably caused by any one or more selected from the group consisting of the hepatitis B virus, the hepatitis C virus decreasing miR-122 expression in liver cancer tissue, alcohol, chronic hepatitis, liver cirrhosis, non-alcoholic fatty acid disease, aflatoxin, and family history.

In an embodiment of the invention, the expression levels of miR-122 in liver cancer caused by various etiological factors were analyzed. As a result, for some liver cancer caused by HCV and liver cancer caused by other factors, the miR-122 expression level in normal liver tissue was higher than the miR-122 expression level in liver cancer tissue. Therefore, it was confirmed that the activity of the ribozyme according to an embodiment of the invention would be decreased in normal liver tissue due to high miR-122 expression level, while its high activity could be maintained in liver cancer tissue where miR-122 expression level is low (FIG. 11).

Figure 6A:
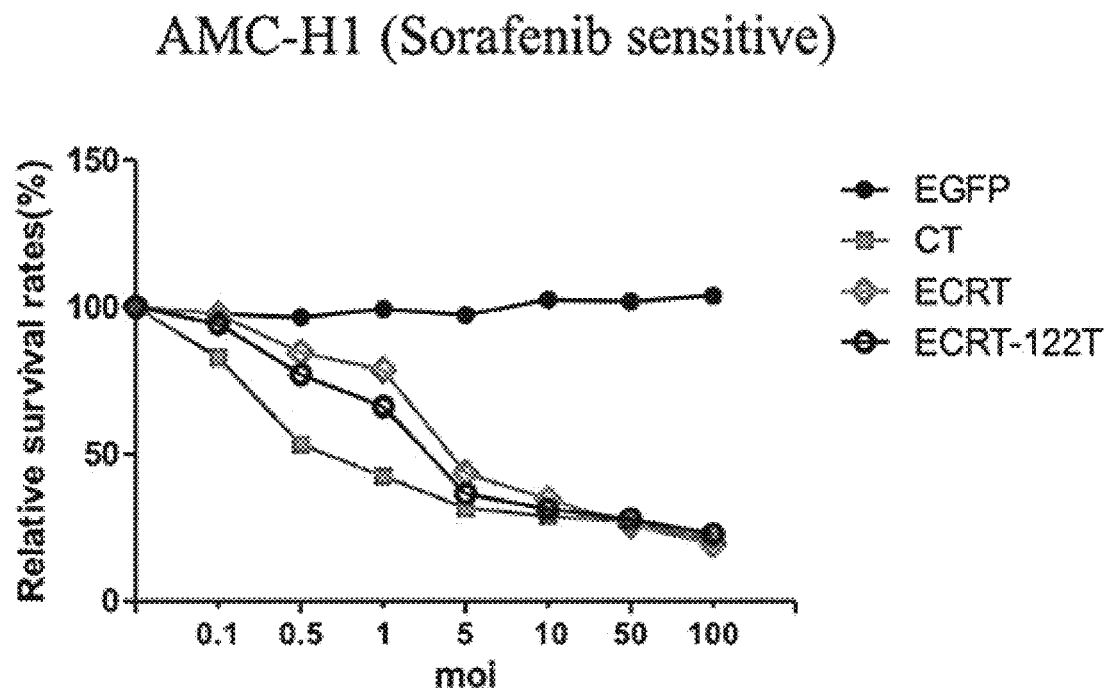
FIG. 6(a) is a graph showing cell survival rates according to the MOI of ECRT-122T adenovirus transduced into cell lines derived from liver cancer patients sensitized to sorafenib.
Figure 6B:
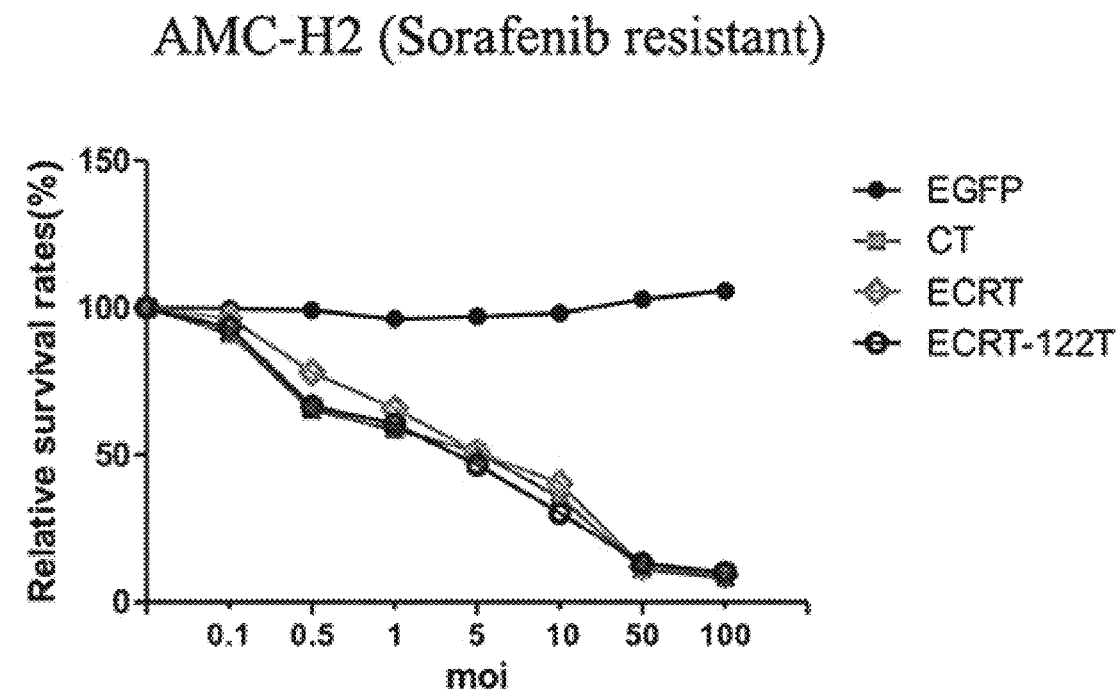
FIG. 6(b) is a graph showing cell survival rates according to the MOI of ECRT-122T adenovirus transduced into cell lines derived from liver cancer patients not sensitized to sorafenib.

In addition, the liver cancer according to an embodiment of the invention may be resistant to sorafenib. Sorafenib is a primary therapeutic agent used against advanced liver cancer, and in one embodiment of the invention, since the ribozyme according to an embodiment of the invention induces cell death in both a sorafenib-sensitizing cell line and a non-sorafenib-sensitizing cell line, it was confirmed that the ribozyme can also be applied to a sorafenib-resistant liver cancer patient group which cannot be treated by sorafenib (FIG. 6).

The term "prevention" used herein refers to all actions of inhibiting cancer or delaying the onset thereof as a result of administration of the composition including the nucleic acid construct according to an embodiment of the invention.

The term "treatment" used herein refers to all actions involved in alleviating or beneficially changing symptoms of cancer or stopping the growth of cancer cells or reducing the size/volume of cancer cells by administration of the composition including the vector according to an embodiment of the invention.

The pharmaceutical composition according to an embodiment of the invention may further include a pharmaceutically acceptable carrier, excipient or diluent. Examples of a pharmaceutically acceptable carrier, excipient or diluent that can be used in the pharmaceutical composition according to an embodiment of the invention may include lactose, dextrose, sucrose, sorbitol, mannitol, xylitol, erythritol, maltitol, starch, acacia gum, alginate, gelatin, calcium phosphate, calcium silicate, calcium carbonate, cellulose, methyl cellulose, polyvinylpyrrolidone, water, methylhydroxy benzoate, propylhydroxy benzoate, talc, magnesium stearate, and mineral oil.

The pharmaceutical composition of an embodiment of the invention may be administered orally or parenterally, and preferably, parenterally according to a desired method.

According to one embodiment of the invention, the pharmaceutical composition according to an embodiment of the invention may be directly administered intravenously, intraarterily, intratumorally or subcutaneously, or in the form of an injection. The injection according to the present invention may be dispersed in a sterilized medium to be used without modification when being administered to a patient, and may be administered after being dispersed at a suitable concentration using distilled water for injections. In addition, when the pharmaceutical composition is prepared as an injection, it may be mixed with a buffer, a preservative, an analgesic, a solubilizer, an isotonic agent, a stabilizer or the like to be formed in a unit dose ampoule or multiple-dose form.

The dose of the pharmaceutical composition of an embodiment of the invention may vary depending on the condition and body weight of a patient, the severity of a disease, a drug type, an administration route and time, and may be suitably selected by one of ordinary skill in the art. Meanwhile, the pharmaceutical composition according to an embodiment of the invention may be used alone, or in combination with adjuvant therapy such as a surgical method.

Hereinafter, an embodiment of the invention will be described in detail with reference to the following examples. However, examples according to an embodiment of the invention may be modified into a variety of different forms, and it should not be construed that the scope of an embodiment of the invention is limited to the following examples. The examples of an embodiment of the invention are provided to more completely describe an embodiment of the invention to those of ordinary skill in the art.

EXAMPLE 1

Construction of an hTERT-Targeting Trans-Splicing Ribozyme Recombinant Vector

To construct an hTERT-targeting trans-splicing ribozyme having miR-122T as a miR-122 target site and exhibiting a high expression level, a recombinant vector was designed.

Specifically, the recombinant vector includes a trans-splicing ribozyme encoding gene, HSV-tk as a therapeutic gene and a CMA promoter. The trans-splicing ribozyme encoding gene targets the +21 residue of hTERT mRNA and has an antisense sequence (SEQ ID NO: 8) of 326 nucleotides in length. Transcription efficiency was enhanced by inserting a SV40 intron splicing donor/acceptor (SD/SA) sequence between the CMV promoter and the ribozyme-encoding gene. The protein expression efficiency of a therapeutic gene was improved by inserting WPRE, a posttranscriptional regulatory element of the Woodchuck hepatitis virus, at the 3' end region of the therapeutic gene HSV-tk, and regulated by miR-122 as a result of inserting three copies of miR-122T at the 3' end of the construct.

The entire vector structure of the trans-splicing ribozyme as designed is shown in FIG. 1, and was named ECRT-122T.

EXAMPLE 2

Construction of Hep3B Stable Cell Line Expressing miR-122

$2 \times 10^5$ Hep3B cells were seeded in a 35 mm culture dish, and cultured at 37° C. in a 5% $CO_2$ incubator. 1 μg of a Tet-repressor (TetR) miR-122 expressing vector and 100 μL of Opti-MEM were put into a 1.5 mL tube, and 5 μL of Lipofectamine 2000 and 100 μL of a serum-free medium were put into another 1.5 mL tube, and the tubes were mixed independently and then stored at room temperature for 5 minutes. Afterward, the contents in the two tubes were mixed together, and then stored at room temperature for 20 minutes to form a liposome-type composite. Twenty minutes later, the tube was centrifuged for 10 seconds, diffused on each cell for transfection, and 4 hours later, the medium was replaced with a fresh medium. After incubation for 24 hours at 37° C. in a 5% $CO_2$ incubator, the cells were washed with 1×PBS and treated with trypsin to detach the cells, and then the detached cells were transferred to a 100-mm culture dish and cultured. The medium was replaced with a medium containing 5 μg/mL of an antibiotic blasticidin once every 2 to 3 days. After cell clones were selected and grown, the expression of TetR by RT-PCR was confirmed.

EXPERIMENTAL EXAMPLE 1

Confirmation of Anticancer Efficacy of ECRT-122T (In Vitro)

1-1. Comparison of Anticancer Efficacy of ECRT-122T According to miR-122 Expression It was confirmed that the anticancer efficacy of ECRT-122T constructed in Example 1 varies according to whether or not miR-122 is expressed in cancer cells.

A Hep3B cell line which expresses hTERT but does not express miR-122 and a Huh-7.5 liver cancer cell line which expresses both hTERT and miR-122 were prepared, and then $1 \times 10^4$ cells derived from each cell line were seeded in a 96-well plate. The next day, according to the multiplicity of infection (MOI) to be treated to the cells, adenoviruses (type 5) were diluted by steps in a cell culture medium to reach a total volume of 100 μL, and then the resultant material was added to each well. Vectors used herein are as follows: ECRT-122T having miR-122T; ECRT not having miR-122T; and CRT consisting of a CMV promoter, an hTERT-targeting trans-splicing ribozyme and HSVtk. Twenty-four hours after the adenovirus treatment, ganciclovir (GCV) was diluted in a cell culture medium and mixed to reach a final volume of 200 μM, followed by treatment to each well. GCV was treated three times every 2 days, and 24 hours after the final GCV treatment, an MTS assay reagent was added, followed by measurement of absorbance at a wavelength of 450 nm in order to confirm living cells.

Figure 2A:
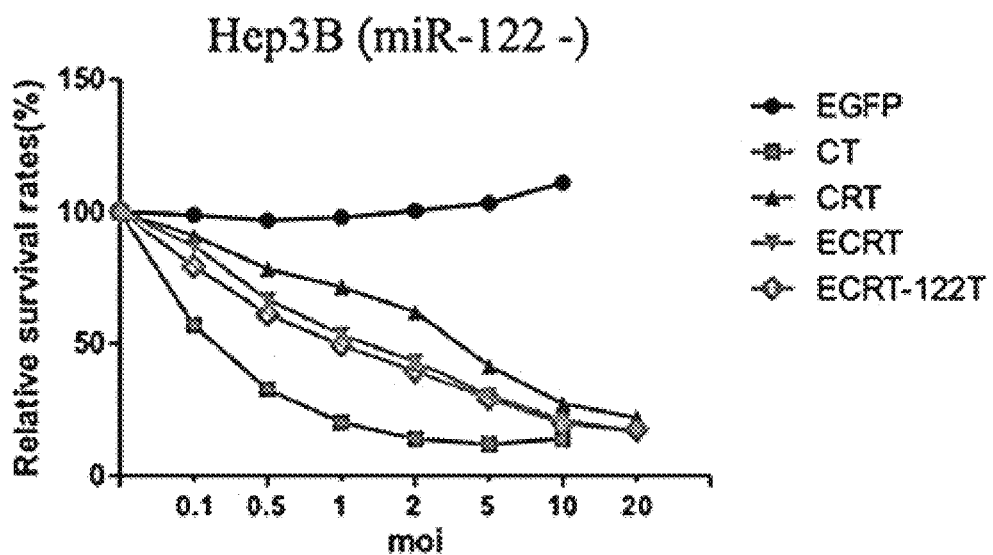
FIG. 2(a) is a graph showing cell survival rates according to the MOI of ECRT-122T adenovirus transduced into a Hep3B cell line not expressing miR-122.

As a result, as shown in FIG. 2(a), in the Hep3B cell line not expressing miR-122, regardless of the presence or absence of a miR-122 target site (ECRT or ECRT-122T), the same degree of cell death was induced. The CRTs not having SD/SA, WPRE and miR-122T induced cell death, but was less effective than those of the ECRT and ECRT-122T, indicating that the efficiency of a ribozyme increases due to an element introduced into the ECRT and ECRT-122T.

Figure 2B:
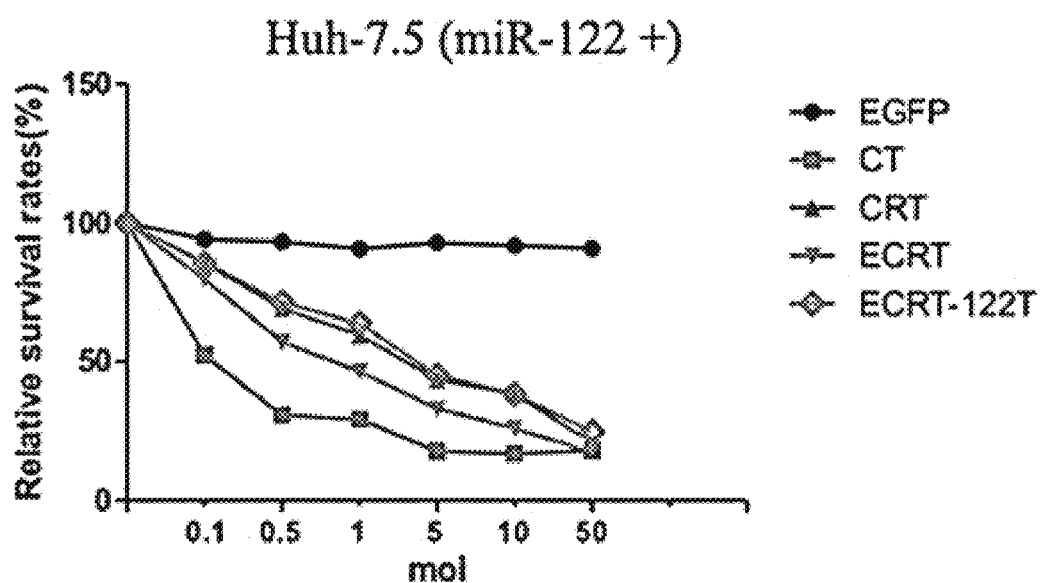
FIG. 2(b) is a graph showing cell survival rates according to the MOI of ECRT-122T adenovirus transduced into a Huh-7.5 cell line expressing miR-122

However, as shown in FIG. 2(b), in the Huh-7.5 cell line expressing miR-122, an effect of inducing cell death by ECRT-122T was reduced, indicating that miR-122 acted on a miR-122 target site introduced into ECRT-122T by interrupting the ribozyme action. However, ECRT-122T still induced cell death at a similar degree to the level by the CRT-treated group, indicating that although being regulated by miR-122 due to miR-122T, ECRT-122T can exhibit an anticancer effect because of high expression of ribozyme, despite miR-122 expression in the cells.

1-2. Comparison of Anticancer Efficacy of ECRT-122T According to Promoter

The anticancer effect of ECRT-122T constructed in Example 1 was compared in vectors with different configurations.

Specifically, Hep3B, SNU398 and SNU449 cell lines expressing hTERT but not expressing miR-122, and Huh-7 and Huh-7.5 liver cancer cell lines expressing both hTERT and miR-122 were prepared. Relative cell survival rates were compared after each of the cell lines were treated with ECRT-122T, ECRT, EPRT-122T in which a liver-specific promoter, that is, a PEPCK promoter, SD/SA, WPRE and miR-122T were introduced into an hTERT-targeting trans-splicing ribozyme encoding gene and HSVtk, or EPRT not having miR-122T. Cell proliferation analysis was performed by the same method as described in Experimental Example 1-1.

As a result, as shown in FIG. 3, in the cell line not expressing miR-122, regardless of the presence or absence of a miR-122 target site (ECRT or ECRT-122T), the same degree of cell death was induced. ECRT-122T induced a higher rate of cell death even in a sample treated with a viral MOI lower than EPRT-122T, indicating that high anticancer efficacy can be exhibited even in a sample treated with a small amount of a virus as a result of more highly increasing the expression of a ribozyme by a CMV promoter compared to a tissue-specific promoter, that is, PEPCK. In addition, ECRT-122T exhibited the same anticancer efficacy as that of the miR-122T-free ECRT, indicating that no decrease in ribozyme activity is caused by the introduction of miR-122T.

Meanwhile, as shown in FIG. 4, cell death caused by EPRT-122T was not observed in a cell line expressing miR-122, indicating that ribozyme expression is reduced by miR-122 acting on miR-122T. However, ECRT-122T induced cell death despite the expression of miR-122, indicating that the CMV promoter can increase ribozyme expression more powerfully than PEPCK. However, unlike a cell line not expressing miR-122, a degree of cell death caused by ECRT-122T was lower than that related to ECRT, indicating that the ribozyme expression was lowered by regulating miR-122T of ECRT-122T by miR-122.

Figure 5:
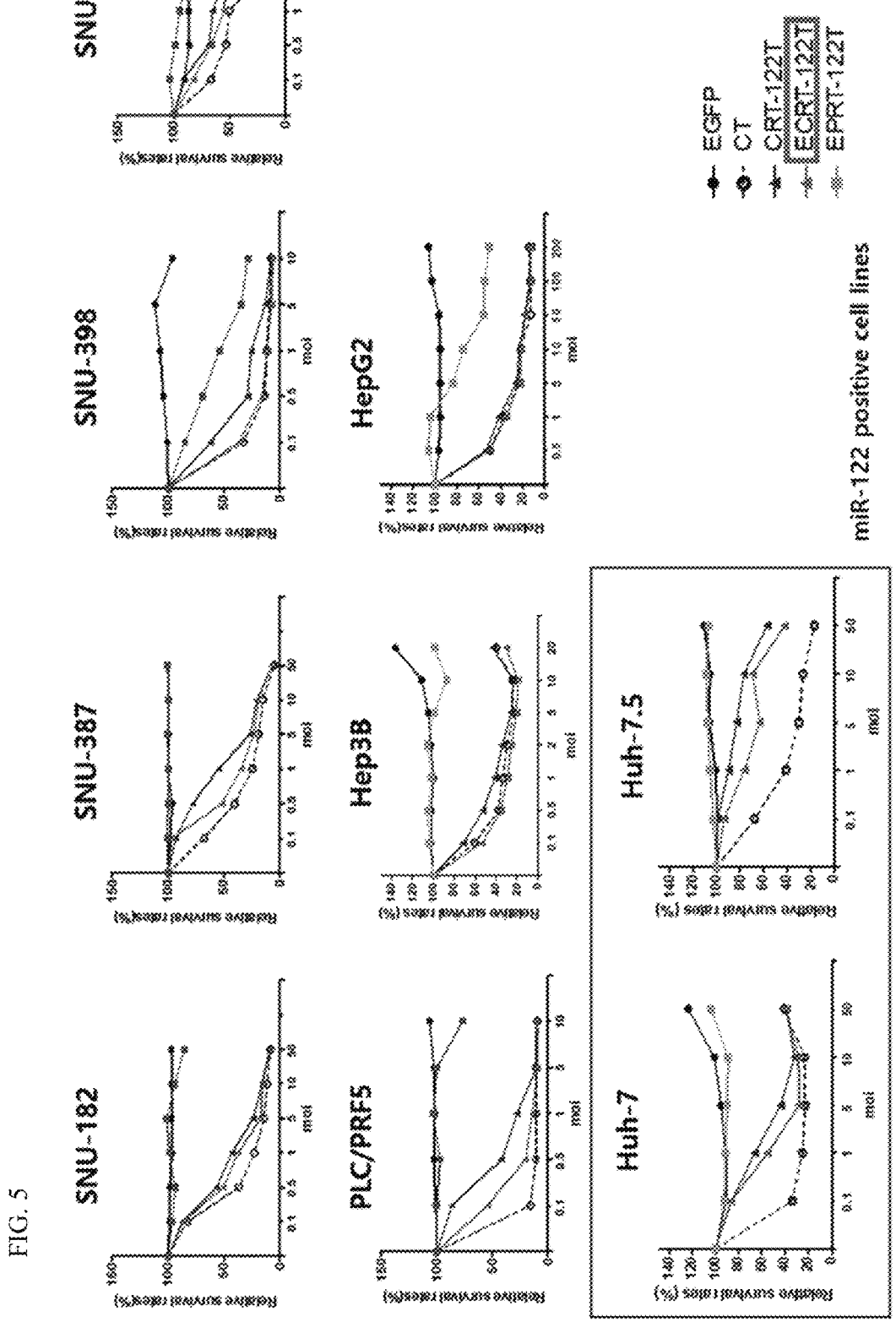
FIG. 5 is a set of graphs showing cell survival rates according to the MOI of ECRT-122T adenovirus transduced into various types of liver cancer cell lines expressing or not expressing miR-122.

In addition, the anticancer effect of CRT-122T, ECRT-122T and EPRT-122T was compared in various liver cancer cell lines. As a result, as shown in FIG. 5, cell death increased by increasing the MOI of ECRT-122T in almost all liver cancer cell lines, and the anticancer effect of ECRT-122T was higher than that of the Comparative Groups (CRT-122T and EPRT-122T).

From the results of Experimental Examples, it can be seen that since anticancer efficacy is increased by increasing ribozyme expression as a result of introducing a CMV promoter, SD/SA and WPRE into a ribozyme-expression vector, and ribozyme activity caused by miR-122 is regulated by the introduction of miR-122T, ECRT-122T is considered as an excellent anticancer agent with enhanced efficacy as well as safety in regards to the treatment of liver cancer.

1-3. Application of ECRT-122T to Sorafenib-Resistant Liver Cancer

The anticancer efficacy of ECRT-122T against liver cancer sensitized to sorafenib, which was used as a primary therapeutic agent against advanced liver cancer, was confirmed.

Specifically, a cell line derived from a liver cancer patient having sorafenib sensitivity or a liver cancer patient without sorafenib sensitivity (resistance) was prepared, and following treatment with ECRT-122T or ECRT, cell survival rates were compared. Cell proliferation analysis was performed by the same method as that described in Experimental Example 1-1.

As a result, as shown in FIG. 6, cell death was observed in all cell lines with and without sorafenib sensitivity. It can be seen that ECRT-122T can also be applied to a sorafenib-resistant liver cancer patient group which shows resistance to sorafenib treatment.

EXPERIMENTAL EXAMPLE 2

Confirmation of Anticancer Efficacy of ECRT-122T (In Vivo)

Anticancer efficacy and hepatotoxicity caused by ECRT-122T in animal models towards liver cancer were confirmed.

Anticancer efficacy was confirmed as a result of inducing orthotopic multifocal liver cancer by injecting a Hep3B cell line not expressing miR-122 into the spleen of a mouse model with metastasized liver cancer in the spleen, and systemically administering the adenovirus expressing ECRT or ECRT-122T by tail-vein injection and injecting GCV.

Figure 7A:
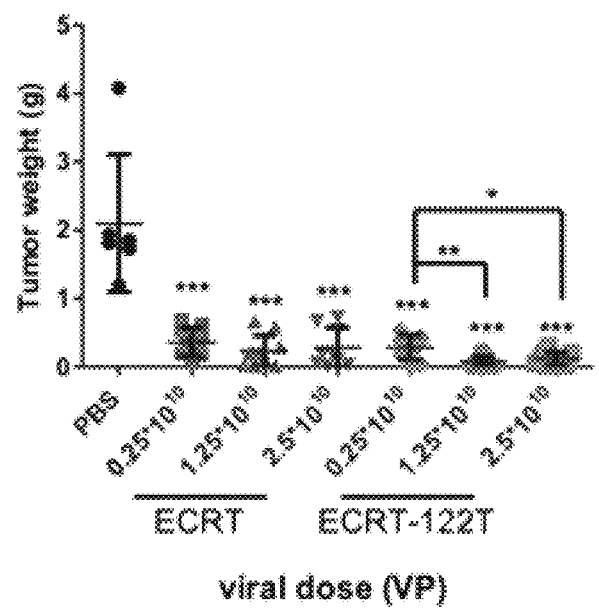
FIG. 7(a) shows the result of identification of a tumor weight according to an injection dose of an adenovirus expressing ECRT or ECRT-122T in animal liver cancer models.
Figure 7B:
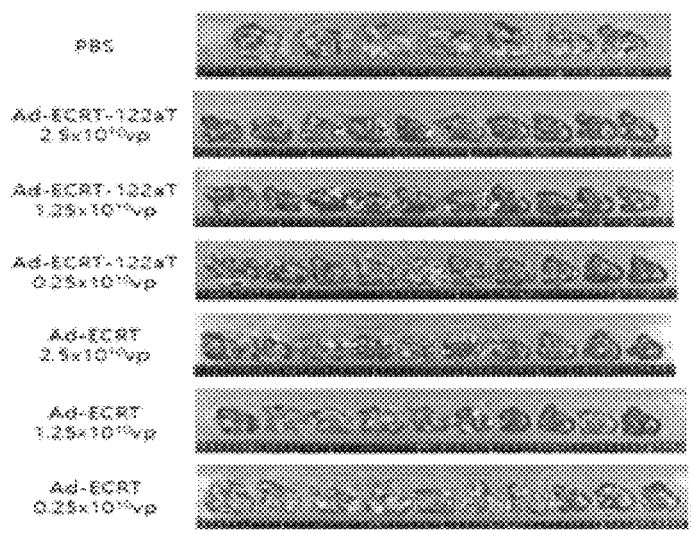
FIG. 7(b) shows the result of identification of tumor tissue according to an injection dose of an adenovirus expressing ECRT or ECRT-122T in animal liver cancer models.
Figure 7C:
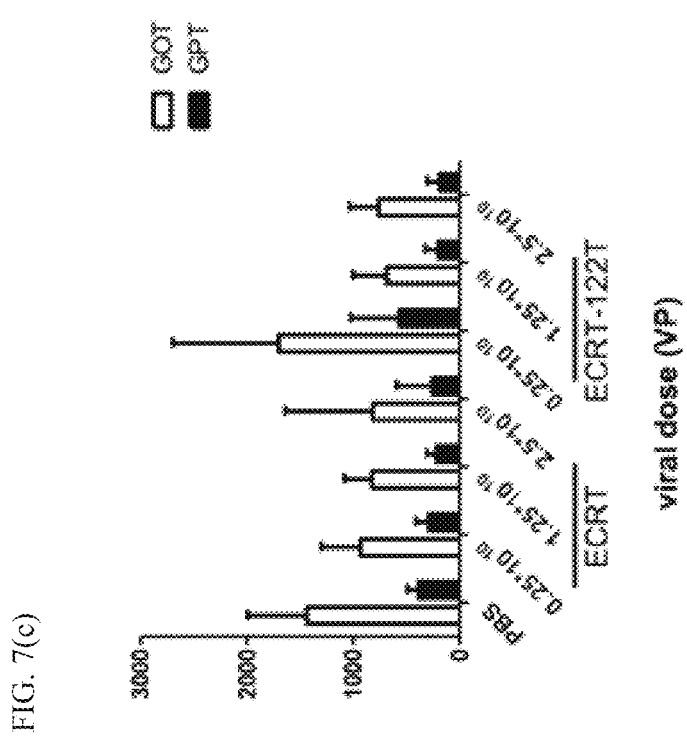
FIG. 7(c) shows the results of identification of liver enzyme levels (glutamic oxaloacetic transaminase (GOT) and glutamic pyruvic transaminase (GPT)) according to an injection dose of an adenovirus expressing ECRT or ECRT-122T in animal liver cancer models.

Consequently, as shown in FIGS. 7(a) and 7(b), most types of cancer cells were killed in an ECRT-122T-injected experimental group, compared with a control group (injected with PBS). Here, ECRT-122T exhibited more excellent anticancer efficacy than ECRT not having miR-122T in the experimental groups injected with the same dose of viruses. From the result, it can be seen that since ribozyme expression is inhibited in normal liver tissue due to the introduction of miR-122T, safety can be ensured within a normal liver, and high anticancer efficacy can be exhibited in cancer tissue. In addition, as shown in FIG. 7(c), compared with the control group (injected with PBS), an ECRT-122T-injected experimental group showed a similar hepatotoxicity level, indicating that in vivo delivery of ECRT-122T using an adenovirus is appropriate.

EXPERIMENTAL EXAMPLE 3

Correlation Between miR-122 Expression Level and Ribozyme Expression Level

To analyze the action of a ribozyme according to the expression level of miR-122, the correlation between the miR-122 expression level and the ribozyme expression level was analyzed.

Huh-7 and Huh-7.5 liver cancer cell lines expressing both hTERT and miR-122 were prepared and treated with adenoviruses expressing ECRT, ECRT-122T, EPRT or EPRT-122T, followed by extracting 5 μg of total RNA with a TRI Reagent.

cDNA was synthesized by reverse transcription performed on the extracted total RNA with a random primer (5'-NNNNNN-3'), and a 10× PCR buffer, 10 mM of dNTP, 10 pmole of each primer, 2.5 units of a Taq polymerase and 1 μL of 10× SYBR Green were added to 2 μL of the synthesized cDNA and diluted with dH$_2$O to reach a final volume of 70 μL. 20 uL of the resulting mixture was dispensed in each well, and subjected to 40 cycles of real-time PCR under conditions of 95° C. for 30 seconds, 58° C. for 30 seconds and 72° C. for 30 seconds to confirm the expression level of a ribozyme. Primer sequences used in the PCR for a ribozyme are shown in Table 1 below.

TABLE 1

| Primer sequence (5'-3') | Sequence (5'-3') |
| --- | --- |
| Ribozyme_forward primer | TTCCGGAGGACAGACACATCGA (SEQ ID NO: 10) |
| Ribozyme_reverse primer | GCAGATACCGCACCGTATTGGC (SEQ ID NO: 11) |

Subsequently, cDNA was synthesized from the extracted total RNA using a mature miR-122 probe (ABI), and 3.5 μL of 20× TaqMan small RNA assay and 35 μL of 2× TaqMan Universal PCR Master Mix II (ABI) were added to 2 μL of the synthesized cDNA and then diluted with dH$_2$O to reach a final volume of 70 μL. 20 uL of the resulting mixture was dispensed in each well, and subjected to 40 cycles of real-time PCR under conditions of 95° C. for 15 seconds and 60° C. for 60 seconds to confirm the expression level of miR-122. PCR of miR-122 was performed using a TaqMan probe provided by ABI (Assay ID: 002245).

As a result, as shown in FIG. 8(c), it was confirmed that approximately 1000 to 2000 copies of miR-122 were expressed in the Huh-7 cell line, and as shown in FIG. 8(b), it can be seen that the expression level of a ribozyme increases according to an increase of MOI in each of the ECRT-122T and ECRT-treated groups. In addition, the ribozyme is expressed more greatly at an infection concentration of 5 MOI or less in the ECRT-122T-treated group, compared with the ECRT-treated group, but when 10 MOI was treated, the ribozyme expression level was lowered in the ECRT-122T-treated group, compared with the ECRT-treated group. From the result, it can be seen that Huh-7-expressing miR-122 acted on miR-122T to reduce ribozyme expression.

Figure 4A:
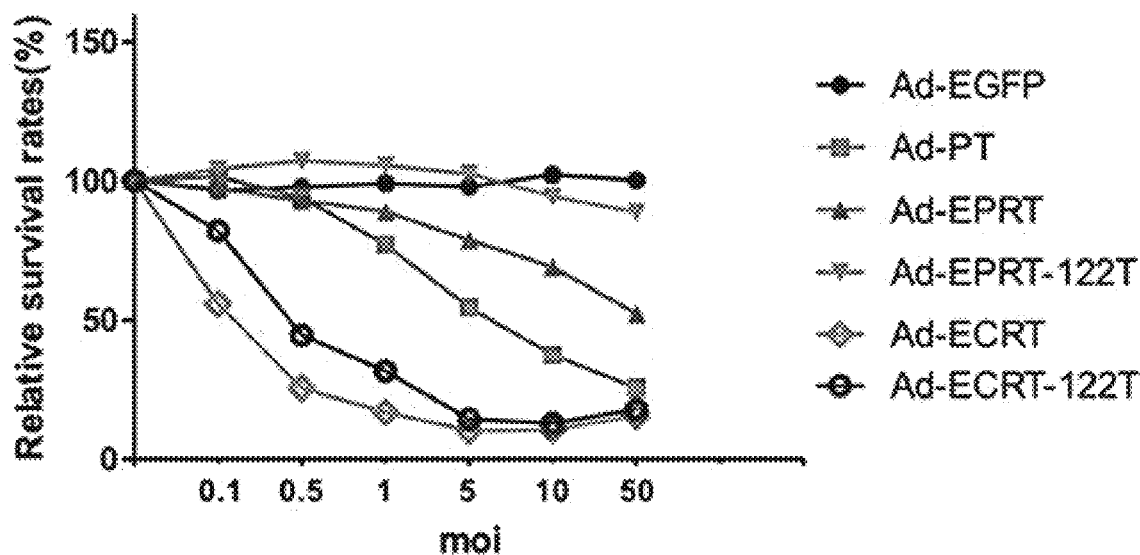
FIG. 4(a) is a graph showing cell survival rates according to the MOI of ECRT-122T adenovirus transduced into a Huh-7 cell line expressing miR-122.

Meanwhile, when ECRT-122T was treated at 10 MOI, a ratio of the copy numbers of the ribozyme and miR-122 was approximately 1:2.5 (600 copies: 1500 copies). In FIG. 4(a) confirming a cell death rate according to MOI, it can be seen that the induction of cell death by ECRT-122T even at 10 MOI was caused by the ribozyme expression due to miR-122 not being sufficiently inhibited as a result of a low ratio of miR-122 to the ribozyme.

Figure 4B:
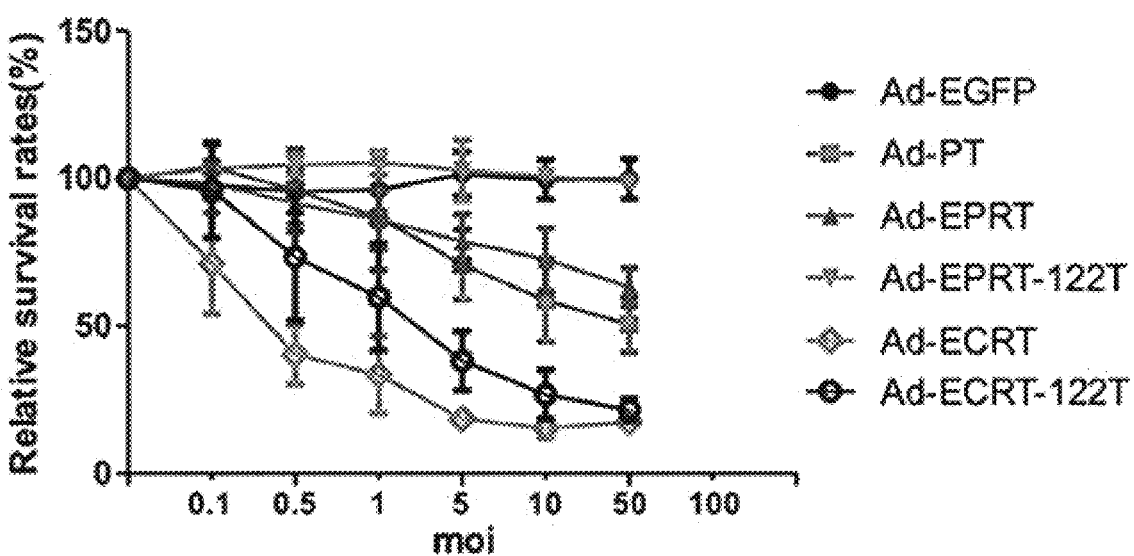
FIG. 4(b) is a graph showing cell survival rates according to the MOI of ECRT-122T adenovirus transduced into a Huh-7.5 cell line expressing miR-122.
Figure 9C:
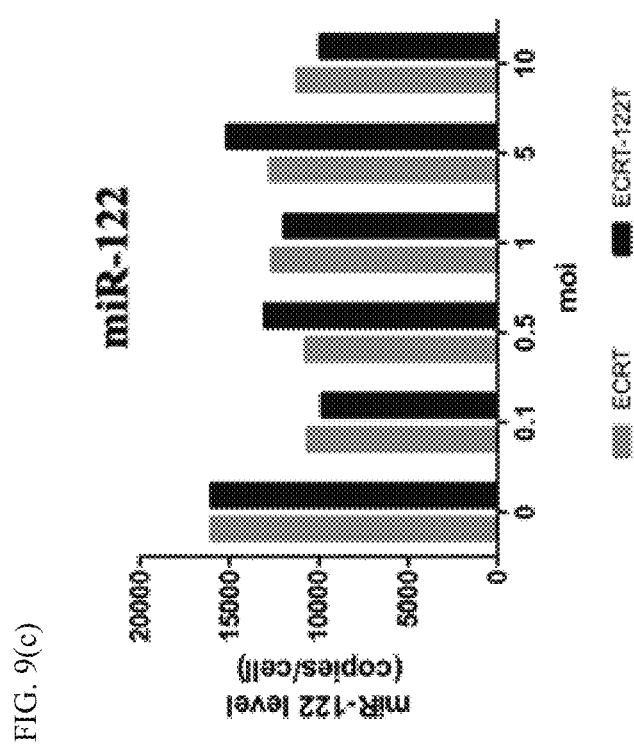
FIG. 9(c) is a graph showing RNA expression level of miR-122 according to the MOI of an ECRT-122T adenovirus transduced into Huh-7.5 cell lines expressing miR-122.
Figure 10A:
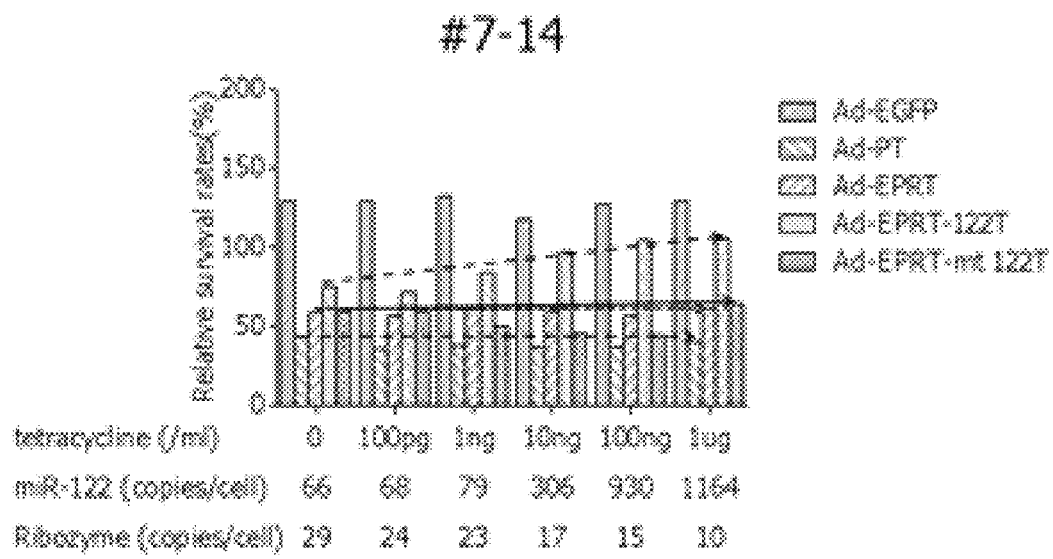
FIG. 10(a) is a graph showing cell survival rate, miR-122 expression level and ribozyme expression level according to the level of concentration of tetracycline and MOI of ECRT-122T adenovirus transduced into Hep3B-stabilized cell line clone #7-14 having an miR-122 tetracycline-on system.
Figure 10B:
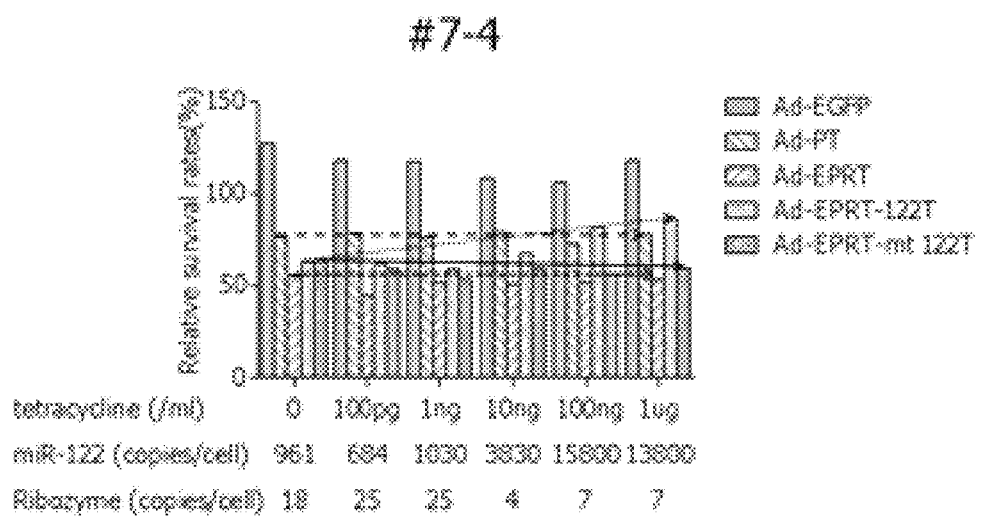
FIG. 10(b) is a graph showing cell survival rate, miR-122 expression level and ribozyme expression level according to the level of concentration of tetracycline and MOI of ECRT-122T adenovirus transduced into Hep3B-stabilized cell line clone #7-4 having an miR-122 tetracycline-on system.
Figure 10C:
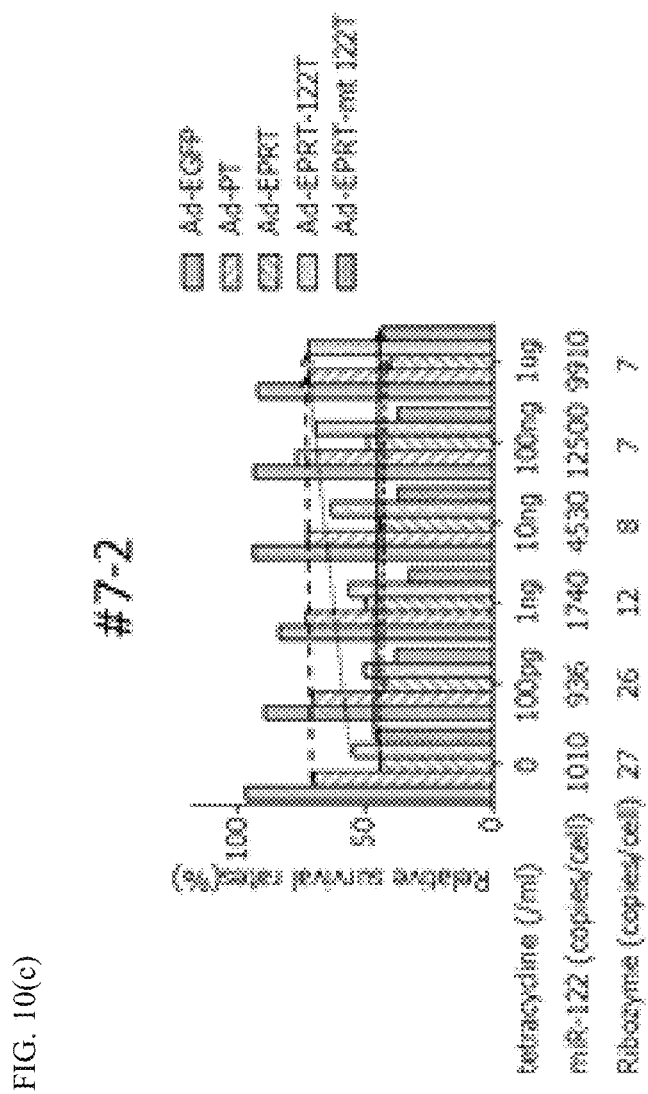
FIG. 10(c) is a graph showing cell survival rate, miR-122 expression level and ribozyme expression level according to the level of concentration of tetracycline and MOI of ECRT-122T adenovirus transduced into Hep3B-stabilized cell line clone #7-2 having an miR-122 tetracycline-on system.

Meanwhile, as shown in FIG. 9(c), approximately 10000 to 15000 copies of miR-122 were expressed in a Huh-7.5 cell line, which was a higher level than that of Huh-7, and it can be seen that a degree of inducing cell death by a ribozyme was lower than that of Huh-7. In addition, as shown in FIG. 9(b), as opposed to Huh-7, under the same infection condition, the ribozyme expression level in the ECRT-treated group was the same or higher than that in the ECRT-122T-treated group, and when 10 MOI was treated, the copy number of the expressed ribozyme was lower (approximately 120 copies) than that in Huh-7 (approximately 600 copies). From the above-mentioned results and the result of FIG. 4(b) showing a cell death rate according to MOI, it can be seen that as the ratio of a ribozyme and miR-122 increased, the ribozyme expression decreased, and thus an effect of inducing cell death was reduced.

EXPERIMENTAL EXAMPLE 4

Action of Ribozyme According to Expression Level of miR-122

To further analyze the interaction between the expression level of miR-122 and a ribozyme, the action of the ribozyme according to the expression level of miR-122 was analyzed.

After a stable cell line (Hep3B) having the miR-122 tetracycline-on system, which was constructed in Example 2, was treated with an adenovirus containing EPRT, EPRT-122T, or EPRT-mt 122T vector having three copies of mutant miR-122 target site in which the sequence was randomly changed to prevent miR-122 binding, cell survival rates were compared. There was in increase in miR-122 expression in the cell line constructed in Example 2 based on a tetracycline treatment concentration, and an experiment was performed using a stable cell line of three clones with different expression levels. Cell proliferation analysis was performed by the same method as described in Experimental Example 1-1.

As a result, as shown in FIG. 10, in the EPRT-122T-treated group, as the tetracycline treatment concentration increased, the miR-122 copy number increased, and thus cell death caused by EPRT-122T was reduced. However, in the case of the EPRT or EPRT-mt 122T treated group, or a positive control PT group, the cell death-inducing effect was maintained regardless of the miR-122 expression level. In addition, as the tetracycline treatment concentration increased, the miR-122 copy number increased, and thus the ribozyme copy number decreased in the EPRT-122T-treated group. The above-mentioned effect was the same with respect to all of the three independent clones used in the experiment.

The correlation between the miR-122 copy number and the ribozyme copy number, confirmed in the experiment, was quantified. As a result, as shown in Table 2 below, while the ratio varies according to cell line, when the minimum copy number of miR-122 is approximately 100 times or higher compared to the ribozyme copy number, the activity of a ribozyme having an miR-122 target site was significantly degraded. From the above-mentioned result, it can be seen that since the expression of a trans-splicing ribozyme having an miR-122 target site can be regulated by miR-122, an injection amount of adenoviruses expressing a ribozyme can be determined by estimating an amount of the ribozymes needed to exhibit an anticancer effect according to the expression level of miR-122.

TABLE 2

| Cell | miR-122 copies/cell | | Ribozyme copies/cell | | Cell death rate (%) | | miR-122/ ribozyme (fold) | |
|---|---|---|---|---|---|---|---|---|
| | Tetracycline | | Tetracycline | | Tetracycline | | Tetracycline | |
| | − | + | − | + | − | + | − | + |
| Hep3B miR-122 stable cell line #7-2 | 1,010 | 9,910 | 27 | 7 | 46 | 29 | 37 | 1,416 |
| Hep3B miR-122 stable cell line #7-4 | 961 | 13,800 | 18 | 7 | 40 | 14 | 53 | 1,971 |
| Hep3B miR-122 stable cell line #7-14 | 66 | 1164 | 29 | 10 | 25 | 0 | 2.6 | 116 |
| Huh-7 | 11,600 | | 29 | | 0 | | 400 | |
| Huh-7.5 | 66,300 | | 111 | | 0 | | 597 | |

EXPERIMENTAL EXAMPLE 5

Analysis of miR-122 Expression in Liver Cancer Patient Tissue

The miR-122 expressions in normal liver tissue and liver cancer tissue of a liver cancer patient were analyzed by real-time PCR.

Specifically, miR-122 expression was analyzed by receiving samples of tissue from 70 liver cancer patients in Korea. Each of a normal liver tissue and a liver cancer tissue of a liver cancer patient was immersed in 1 mL of a TRIzol solution, homogenized, and left for 5 minutes at room temperature. Afterward, 0.2 mL of chloroform was added, left alone for 3 minutes at room temperature, and centrifuged for 30 minutes at 4° C. and 12,000 rpm to only separate a supernatant. 0.5 mL of isopropanol was added to the separated supernatant and reacted at −20° C., and the resulting mixture was centrifuged again for 20 minutes at 4° C. and 14,000 rpm to obtain an RNA pellet, which was then dissolved in 100 μL of RNase-free water. cDNA was synthesized by reverse transcription from 50 ng of extracted RNA using a TaqMan miRNA Reverse Transcription kit, and 1 μL of the synthesized cDNA was mixed with a TaqMan 2X Universal PCR Master Mix and subjected to PCR using an ABI StepOne Plus instrument. PCR was performed using a TaqMan probe provided by ABI (Assay ID: 002245).

Figure 11A:
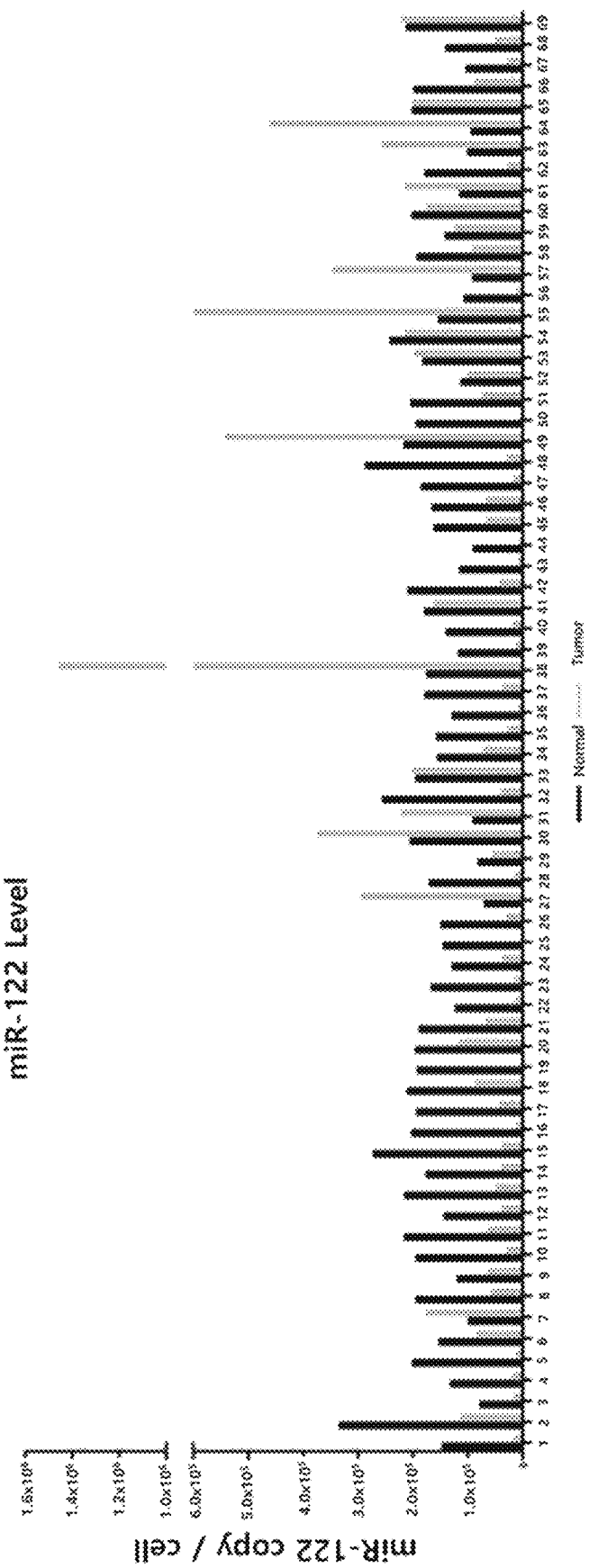
FIG. 11(a) is a graph comparing miR-122 expression levels in normal liver tissue and liver cancer tissue of the entire liver cancer patient group.
Figure 11B:
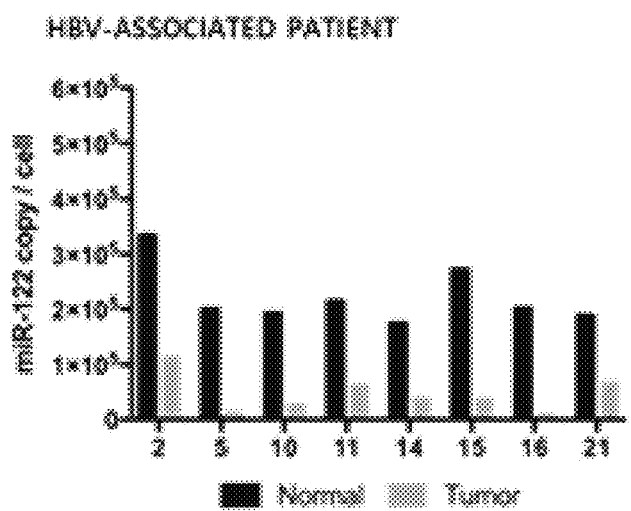
FIG. 11(b) is a graph comparing miR-122 expression levels in normal liver tissue and liver cancer tissue of the HBV-associated liver cancer patient group.
Figure 11C:
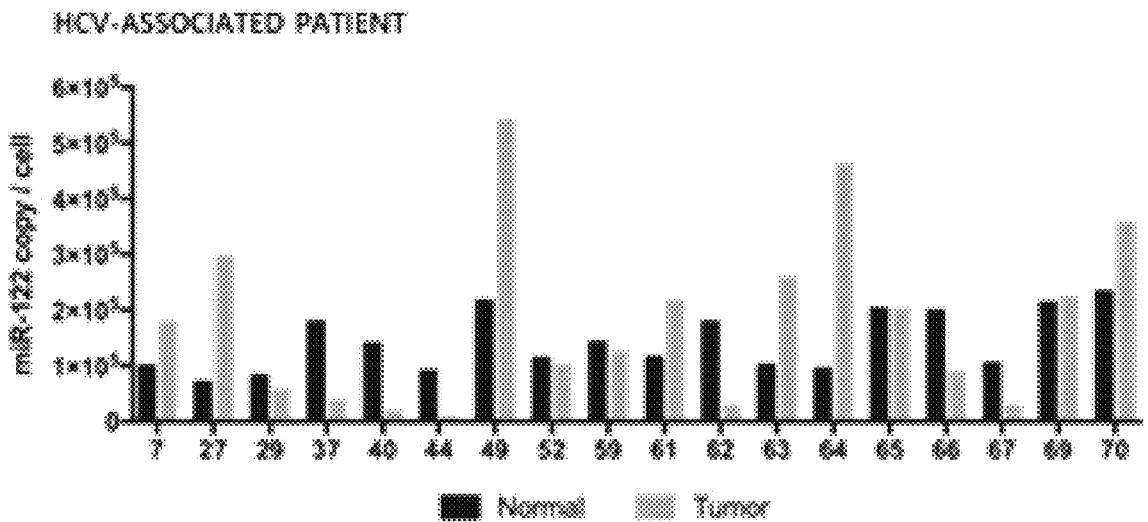
FIG. 11(c) is a graph comparing miR-122 expression levels in normal liver tissue and liver cancer tissue of the HCV-associated liver cancer patient group.
Figure 11D:
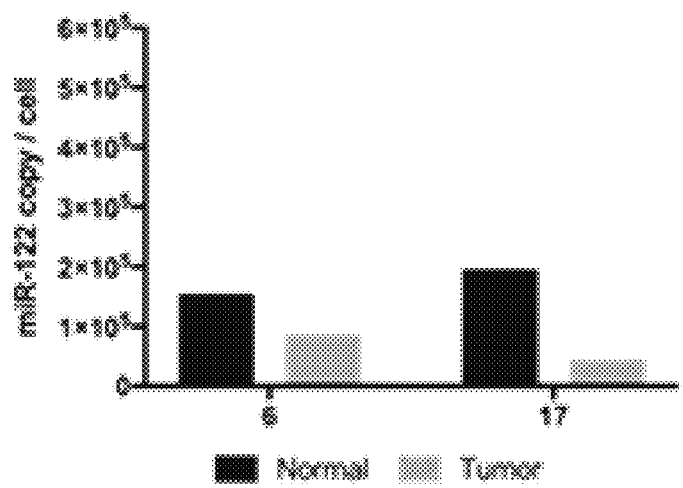
FIG. 11(d) is a graph comparing miR-122 expression levels in normal liver tissue and liver cancer tissue of the alcohol-associated liver cancer patient group.
Figure 11E:
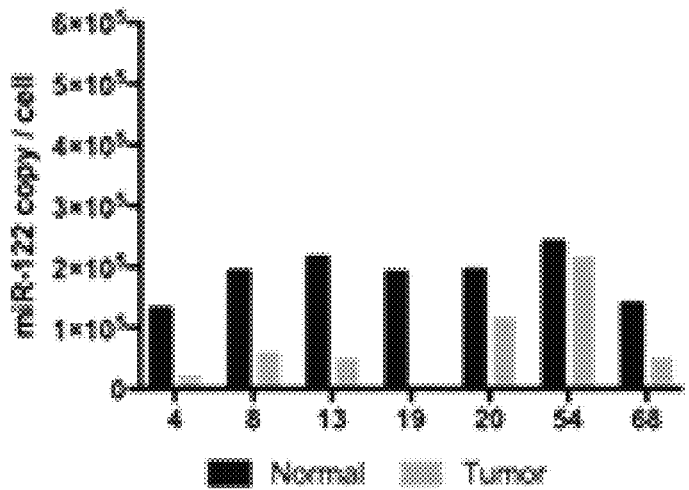
FIG. 11(e) is a graph comparing miR-122 expression levels in normal liver tissue and liver cancer tissue of the chronic hepatitis-associated liver cancer patient group excluding HBV and HCV-associated patient groups.
Figure 11F:
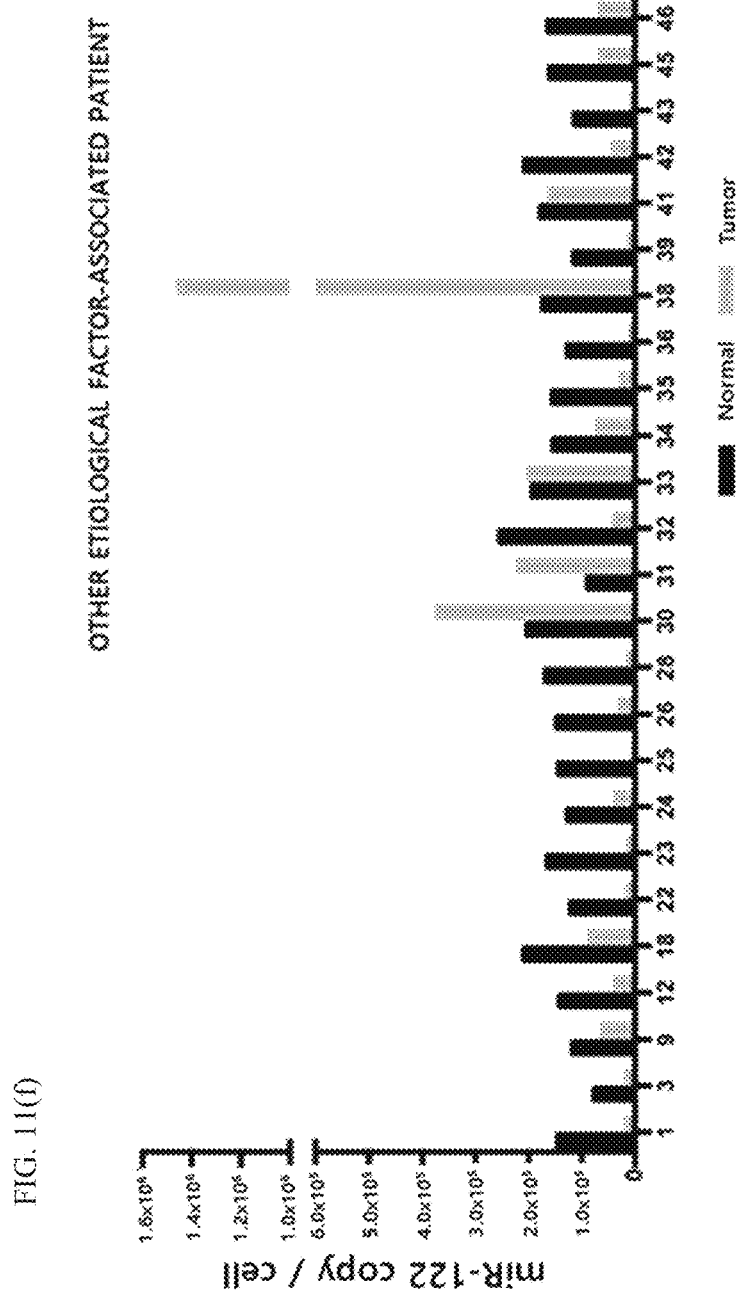
FIG. 11(f) is a graph comparing miR-122 expression levels in normal liver tissue and liver cancer tissue of the liver cancer patient group associated with other etiological factors.

As a result, as shown in FIG. 11(a), the miR-122 expression level in the liver cancer tissue was lower than that in the normal liver tissue in 48 (68.6%) of the 70 patients. According to etiological analysis, as shown in FIGS. 11(b) and 11(d) to 11(f), miR-122 was expressed at a low level in liver cancer tissue, compared with normal liver tissue, in 8 of 8 HBV-associated patients, 2 of 2 alcohol-associated patients, 6 of 7 chronic hepatitis-associated patients, and 26 of 36 liver cancer patients with a cause based on other etiological factors. However, as shown in FIG. 11(c), miR-122 was expressed at a low level in liver cancer tissue in only 6 of 18 HCV-associated patients. From this result, it can be seen that in patients with advanced liver cancer caused by HCV, as opposed to those caused by other etiological factors, miR-122 expression increased or was maintained.

In addition, according to statistical analysis, as shown in Table 3 below, in the case of HCV-associated patients, a phenomenon in which the miR-122 expression is highly observed in liver cancer tissue, compared with normal liver tissue, was shown to be statistically significant, and in the case of another hepatitis virus HBV, a phenomenon in which miR-122 expression decreases in all types of liver cancer tissue is shown to be statistically significant. From this result, it can be seen that the maintenance or increase in miR-122 expression in liver cancer tissue of a HCV-associated patient was statistically significant, and is a HCV-specific phenomenon, not a general phenomenon caused by a hepatitis virus.

TABLE 3

| Etiological factor | Patient Number (n = 70) | miR-122 level normal > cancer | miR-122 level normal <= cancer | P value |
|---|---|---|---|---|
| | | Group 1 | | 0.0021 |
| HBV | 8 (11.4%) | 8 (100%) | 0 (0%) | |
| HCV | 18 (25.7%) | 6 (33.3%) | 12 (66.7%) | |
| Alcohol | 2 (2.9%) | 2 (100%) | 0 (0%) | |
| Chronic hepatitis | 7 (10%) | 6 (85.7%) | 1 (14.3%) | |
| Other | 35 (50%) | 26 (74.3%) | 9 (25.7%) | |
| | | Group 2 | | 0.0498 |
| Non-HBV | 62 (88.6%) | 40 (64.5%) | 22 (35.5%) | |
| HBV | 8 (11.4%) | 8 (100%) | 0 (0%) | |
| | | Group 3 | | 0.0007 |
| Non-HCV | 52 (74.3%) | 42 (80.8%) | 10 (19.2%) | |
| HCV | 18 (25.7%) | 6 (33.3%) | 12 (66.7%) | |

From this result, it can be seen that when ECRT-122T was applied to patients with various types of liver cancer, excluding those caused by HCV with an increase in miR-122 expression in liver cancer tissue compared to normal liver tissue, because the ribozyme does not act on the normal liver tissue due to miR-122 but acts on liver cancer tissue having decreased miR-122 expression, a cancer-specific anticancer action may be exhibited.

In addition, the mRNA and protein levels of hTERT and the miR-122 level of a liver cancer cell line derived from liver cancer cells of a patient were analyzed. A liver cancer cell line was incubated to isolate RNA and protein by a method known in the art. The RNA was used for qRT-PCT, and the protein was subjected to electrophoresis and western blotting.

Figure 12A:
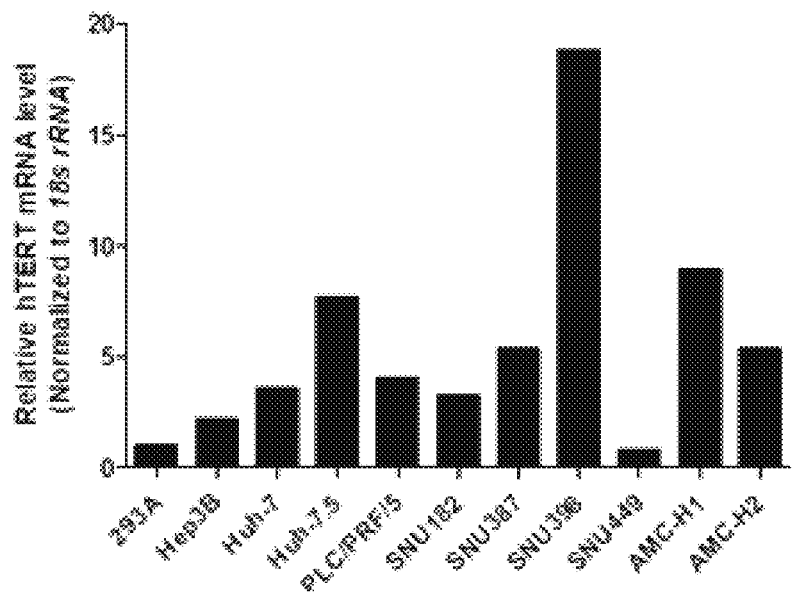
FIG. 12(a) is a graph showing analysis of mRNA levels of hTERT in an established liver cancer cell line derived from the liver cancer cells of patients.
Figure 12B:
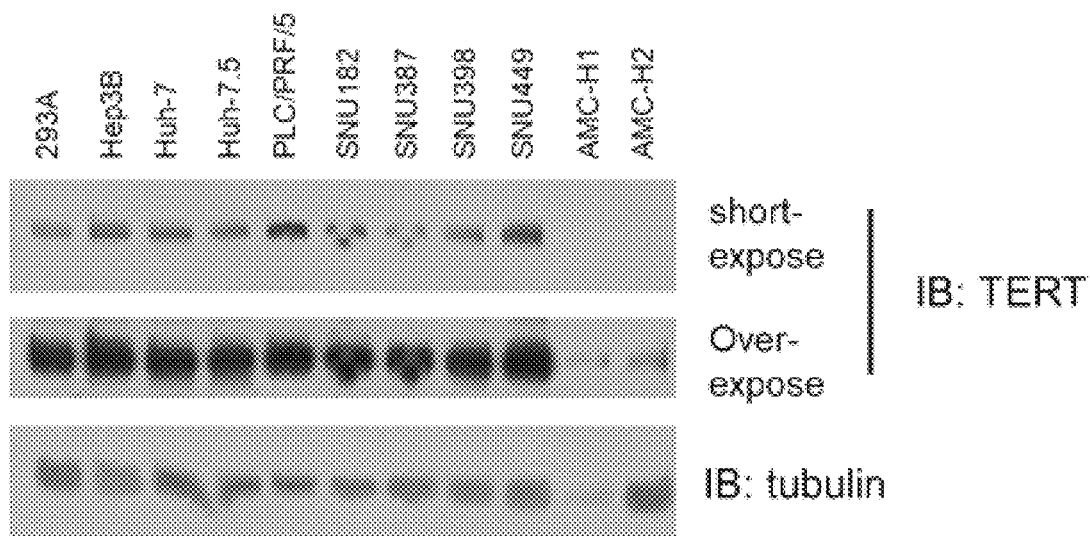
FIG. 12(b) is a graph showing analysis of protein levels of hTERT in an established liver cancer cell line derived from the liver cancer cells of patients.
Figure 12C:
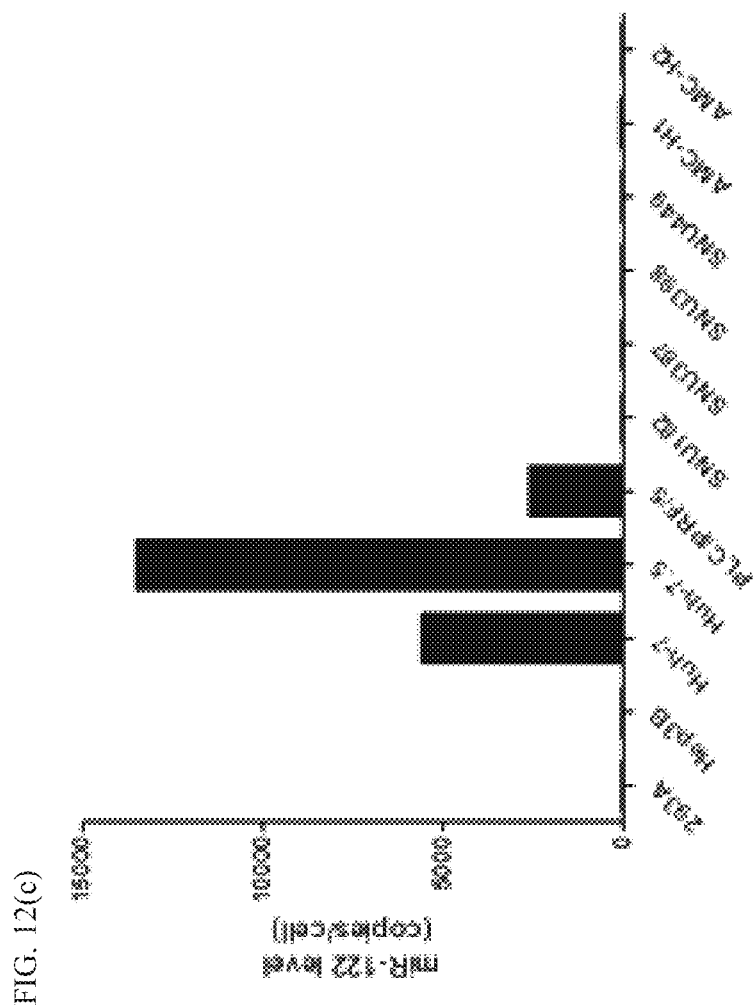
FIG. 12(c) is a graph showing analysis of miR-122 levels in an established liver cancer cell line derived from the liver cancer cells of patients.

As a result, as shown in FIGS. 12(a) and 12(b), it can be confirmed that mRNA of hTERT, which is a target molecule of ECRT-122T, was expressed in most of the liver cancer cell lines, and an hTERT protein level showed a similar result. In addition, similar to results showing reduced expression in liver cancer tissue, it was confirmed that miR-122 was hardly expressed in each of the liver cancer cells line (FIG. 12(c)).

EXPERIMENTAL EXAMPLE 6

Application to Tumors not Expressing miR-122, Other than Liver Cancer 6-1. Cell Experiment (In Vitro)

The anticancer efficacy of ECRT-122T was confirmed in a cancer cell line of tissue not substantially expressing miR-122.

Specifically, a glioblastoma cell line, a colon cancer cell line, a melanoma cell line, a cervical cancer cell line, a lung cancer cell line, an osteosarcoma cell line, a breast cancer cell line and a bile duct cancer cell line, which express hTERT, were treated with an ECRT-122T-expressing adenoviruses, and cell survival rates were compared. Cell proliferation analysis was performed by the same method as that described in Experimental Example 1-1.

As a result, as shown in FIG. 13, as the MOI increased in almost all cancer cell lines, cell death increased, and the anticancer effect of ECRT-122T was superior to that in the Comparative Groups (CRT-122T and EPRT-122T). Specifically, EPRT-122T including a liver tissue-specific promoter often failed to induce cell death, and CRT-122T induced cell death but had lower efficiency than ECRT-122T.

In glioblastoma cell lines T98G and U87MG, approximately 90% cell death was shown at approximately 1 MOI or less, and in a LN229 cell line, approximately 90% cell death was shown at 5 MOI or more. In addition, in a cervical cancer cell line HeLa, 90% or more cell death was shown at 0.5 MOI or less, and in a melanoma cell line SK-MEL2, approximately 90% cell death was confirmed at approximately 1 MOI or less.

In addition, as shown in FIG. 14, in bile duct cancer cell lines SNU478 and SNU869, as the MOI increased, cell death increased.

6-2. Animal Experiment (In Vivo)

$1 \times 10^7$ (100 μL) cells of a glioblastoma cell line LN229 or $5 \times 10^6$ (100 μL) cells of a U87MG cell line were subcutaneously injected into 6-week-old male Balb/c-nunu mice to induce tumorigenesis. When tumors had grown to a certain size, ECRT-122T adenoviruses were injected at a dose of $1.0 \times 10^9$ VP (100 μL) three times every 2 days. Twenty-four hours after the first virus injection, GCV was administered at a dose of 50 mg/kg twice a day for 10 days (a total of 20 times).

Figure 15A:
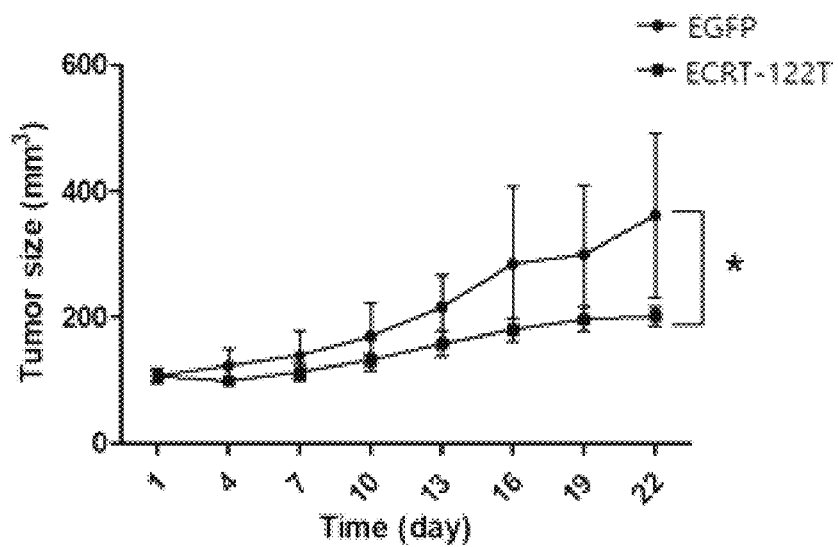
FIG. 15(a) is a graph identifying a tumor size as a result of injecting glioblastoma cells, that is, a LN229 cell line, into a nude mouse to induce tumorigenesis, and then administering ECRT-122T adenovirus.
Figure 15B:
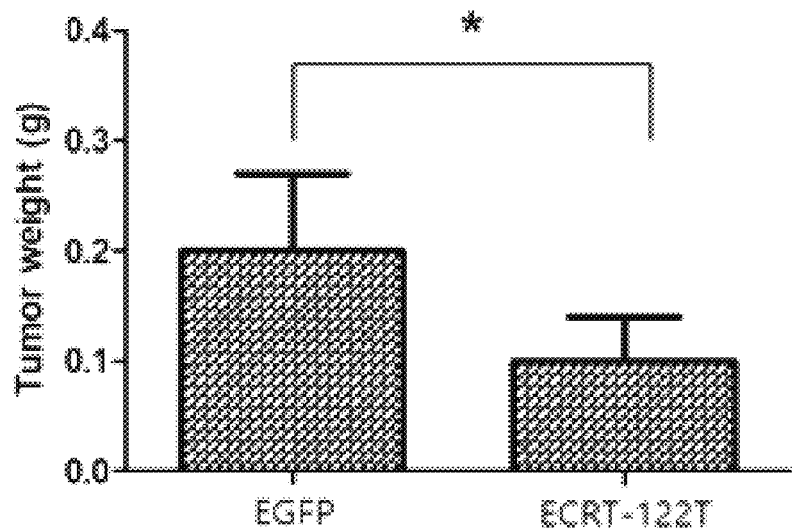
FIG. 15(b) is a graph identifying a tumor weight as a result of injecting glioblastoma cells, that is, a LN229 cell line, into a nude mouse to induce tumorigenesis, and then administering ECRT-122T adenovirus.
Figure 16:
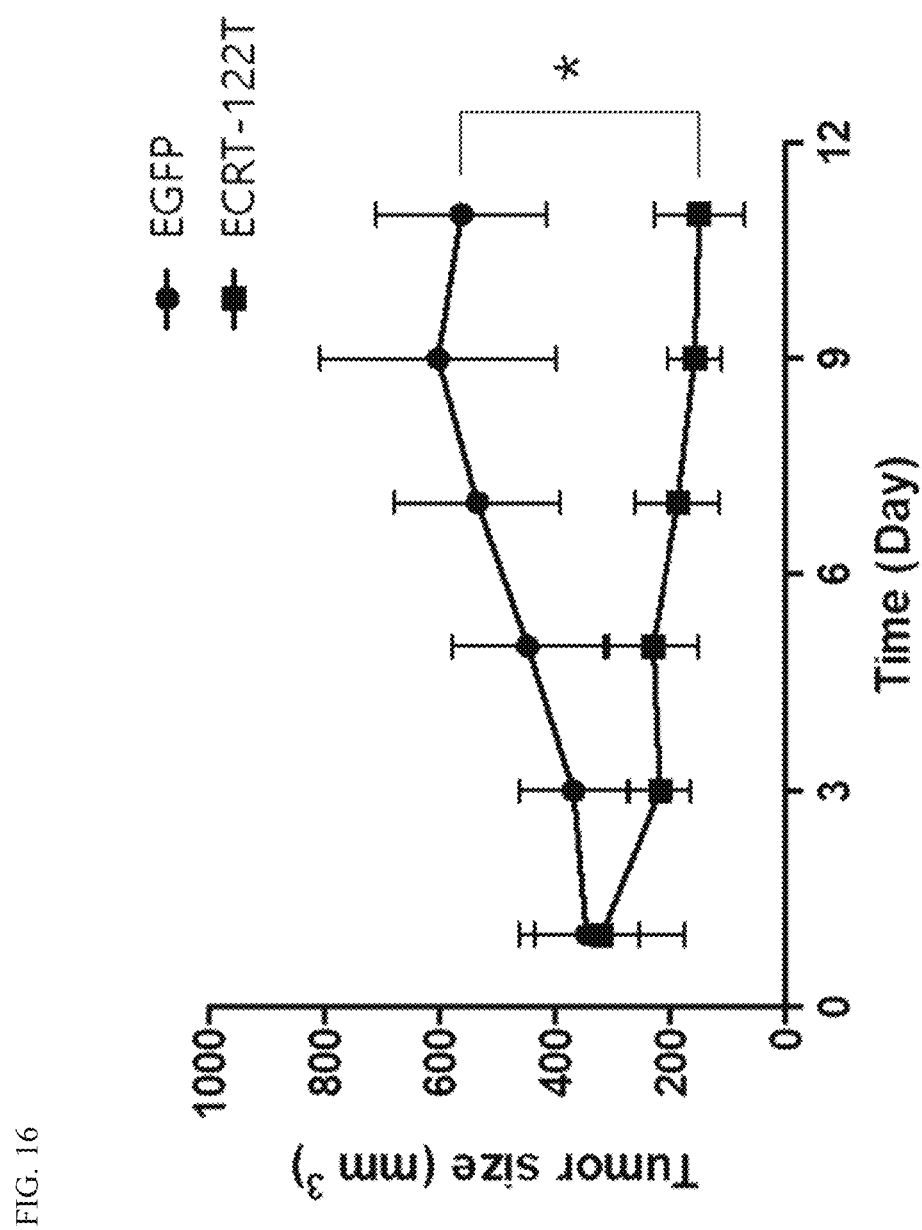
FIG. 16 is a graph identifying a tumor size as a result of injecting glioblastoma cells, that is, a U87MG cell line, into a nude mouse to induce tumorigenesis, and then administering ECRT-122T adenovirus.

As a result of the experiment, as shown in FIG. 15, it can be seen that a tumor size gradually increased in a control group (injected with Ad-EGFP), but the tumor hardly grew in an ECRT-122T-injected experimental group, and a tumor weight was lower in the ECRT-122T-injected experimental group in all cases. In addition, as shown in FIG. 16, the tumor growth inhibitory effect of ECRT-122T was confirmed even in the experiment using the U87MG cell line.

From the result of Experimental Example 6, it was confirmed that a ribozyme expressed from ECRT-122T can be effectively applied to various carcinomas other than liver cancer that do not express miR-122. In addition, when ECRT-122T was systemically or locally administered as an anti-cancer agent against other types of cancer other than liver cancer, it can be introduced into a normal liver, and at that time, due to the action of miR-122T, the induction of toxicity in a normal liver may be inhibited.

EXPERIMENTAL EXAMPLE 7

Confirmation of In Vivo Distribution of ECRT-122T 7-1. Intravenous Injection

ECRT-122T adenoviruses were injected into normal ICR mice at a dose of $2.5 \times 10^{10}$ VP by intravenous injection, and then, 8, 11 and 15 days later, each major organ was isolated to extract DNA. The extracted DNA was used as a template, and subjected to PCR using primer sets for detecting a ribozyme to confirm ECRT-122T distribution in major tissue.

Figure 17:
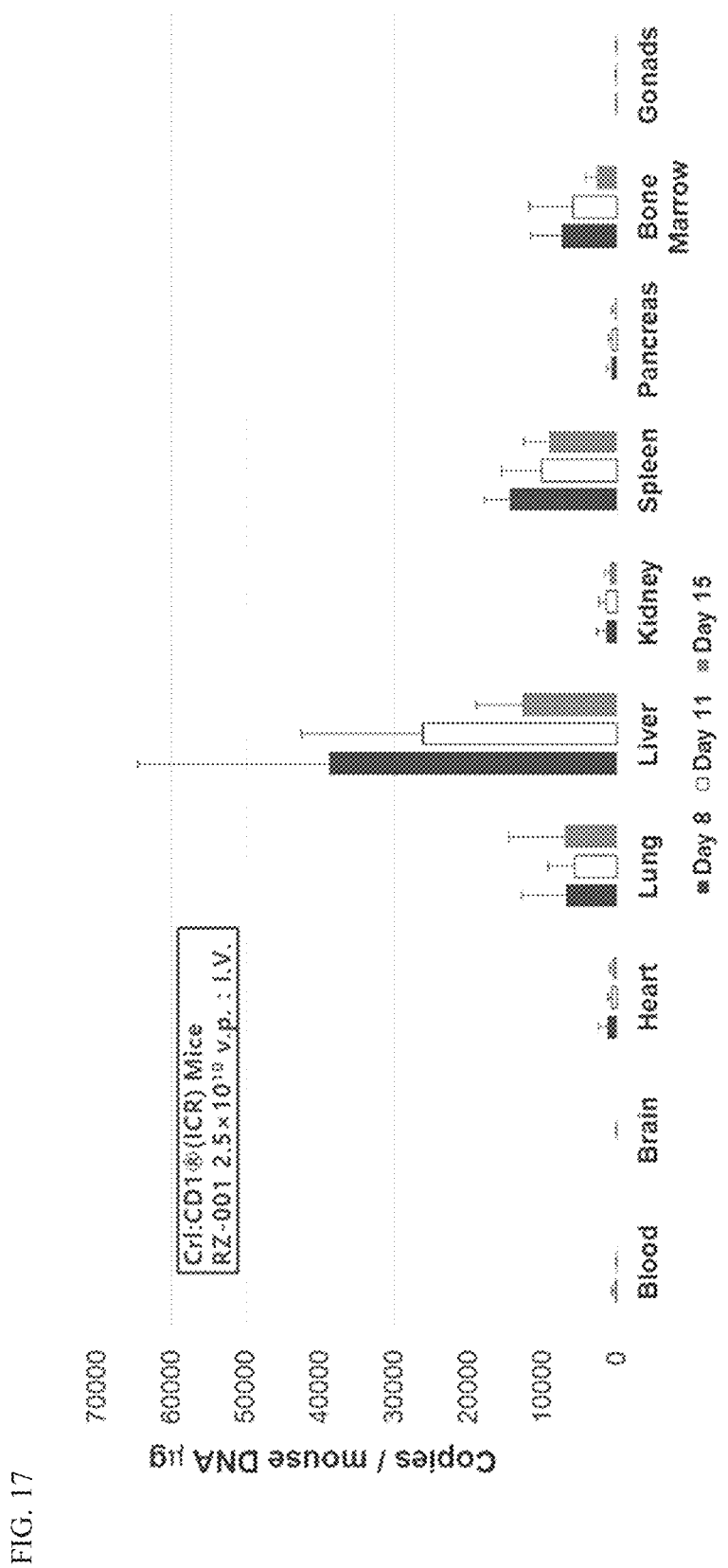
FIG. 17 is a graph showing the degree of distribution of a recombinant vector in major tissue after ECRT-122T adenovirus is injected into a normal ICR mouse through an intravenous injection.

As a result, as shown in FIG. 17, it can be confirmed that almost all injected adenoviruses were distributed in the liver, indicating that adenoviruses are appropriate for use in the delivery of ECRT-122T to the targeted liver cancer. In addition, the injected ECRT-122T had completely disappeared from the blood by day 11 after the systemic introduction, and beginning at 8 days after the systemic injection and within two weeks of the injection, 70% of viral DNA had disappeared.

7-2. Hepatic Artery Injection

ECRT-122T adenoviruses were injected into rats at a dose of $2.5 \times 10^{11}$ VP by hepatic artery injection, and ECRT-122T distribution in major tissue was confirmed by the same method as that described in 7-1.

Figure 18A:
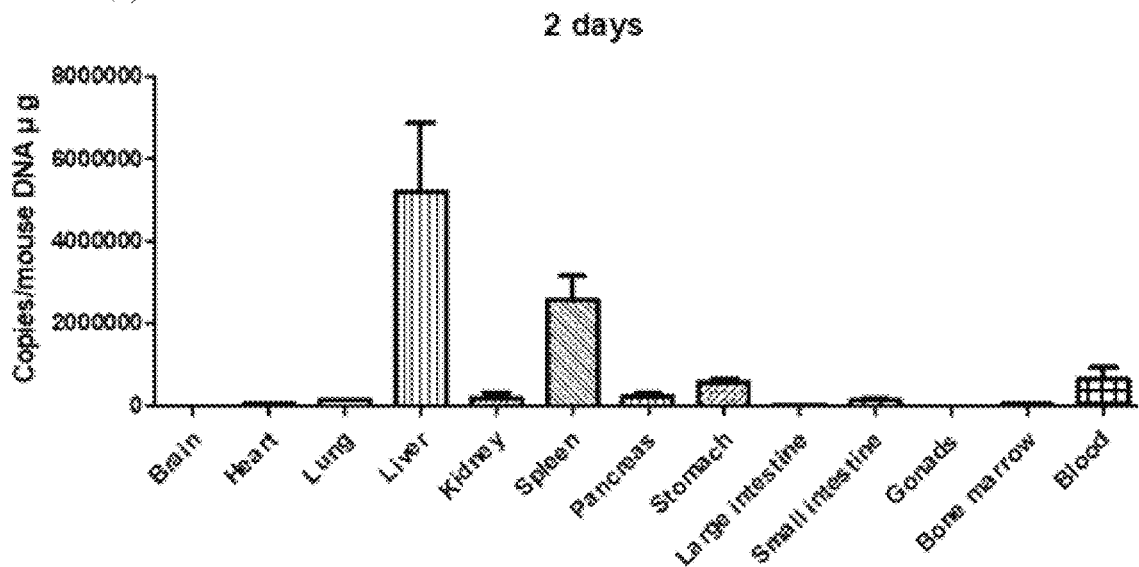
FIG. 18(a) is a graph showing the degree of distribution of a recombinant vector in major tissue 2 days after an administration of a hepatic arterial injection of ECRT-122T adenovirus into a rat.
Figure 18B:
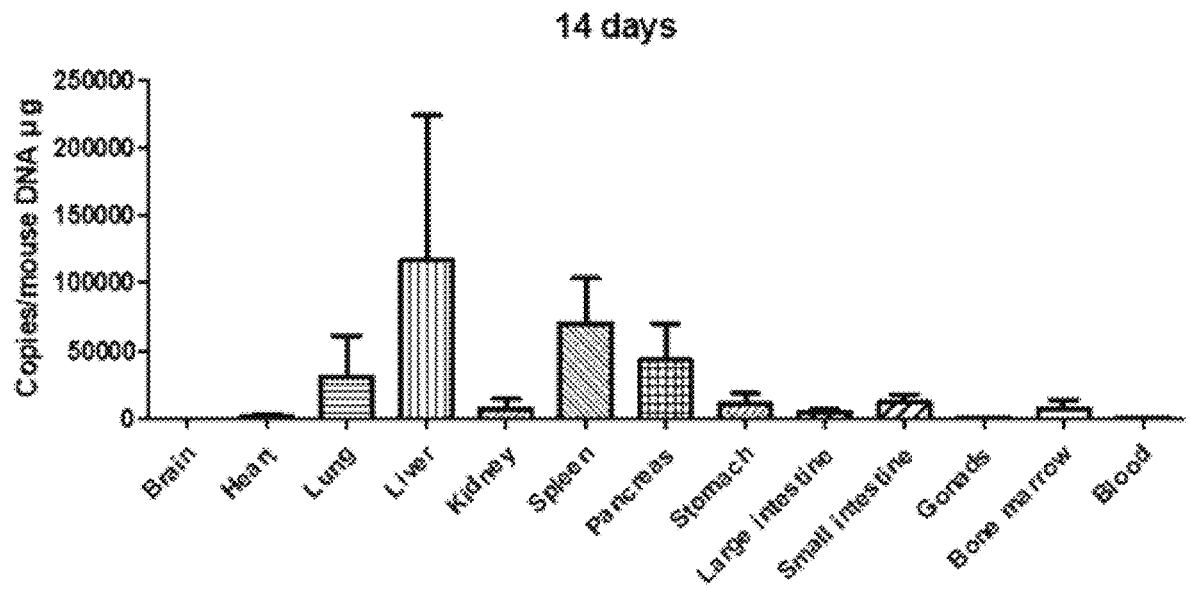
FIG. 18(b) is a graph showing the degree of distribution of a recombinant vector in major tissue 14 days after an administration of a hepatic arterial injection of ECRT-122T adenovirus into a rat.

As a result, as shown in FIG. 18, on the second day after the injection, the largest amount of ECRT-122T DNA was detected in the liver, a level which was maintained up to 14 days after injection. 98% of the viral DNA had disappeared from the liver by day 14 after the injection, and almost all of the viral DNA had also disappeared from other tissues.

Figure 19:
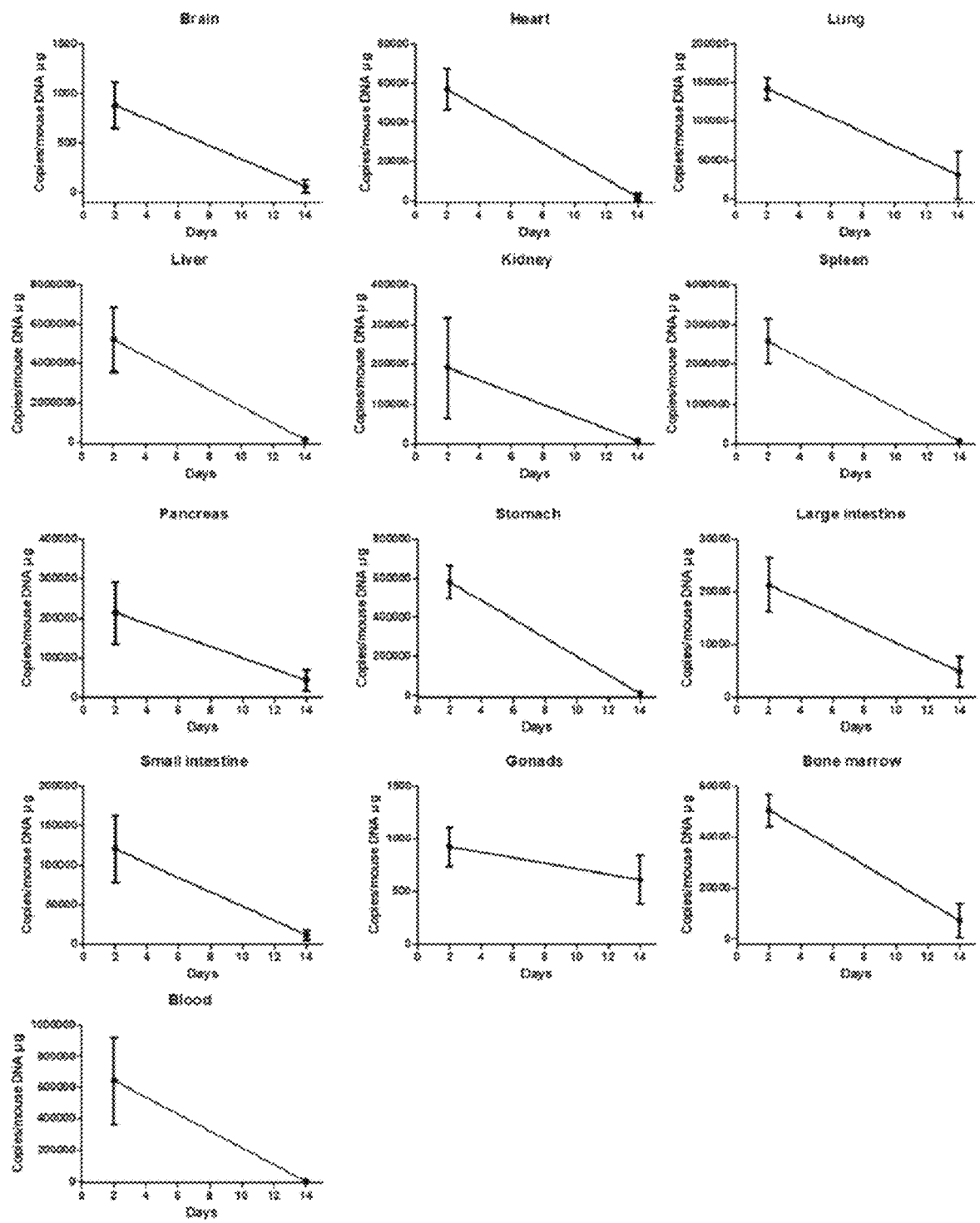
FIG. 19 is a graph showing the results of quantifying HSVtk DNA by isolating genomic DNA (gDNA) from each organ after ECRT-122T adenovirus is injected into a rat through a hepatic arterial injection.

In addition, genomic DNA (gDNA) was isolated from each organ of a rat to quantify HSVtk DNA. As a result, as shown in FIG. 19, it can be seen that HSVtk DNA had disappeared from almost all organs by day 14 after the injection.

Figure 20A:
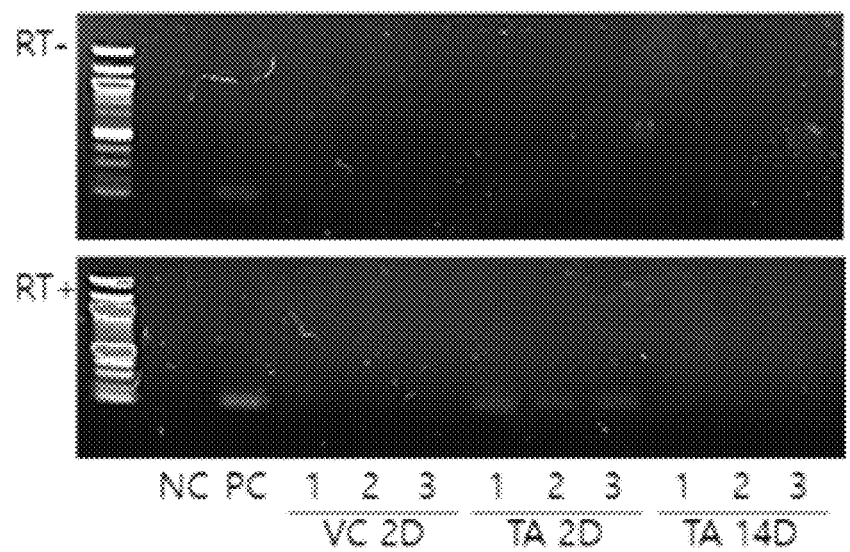
FIG. 20(a) is the results of confirming ribozyme expression levels using qRT-PCR from RNA isolated from the liver after ECRT-122T adenovirus is injected into a rat through a hepatic arterial injection.
Figure 20B:
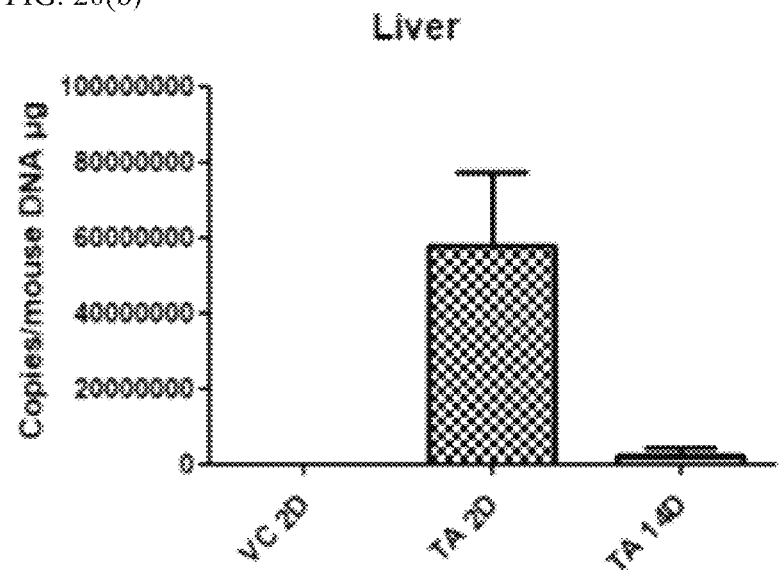
FIG. 20(b) is a graph showing the results of confirming ribozyme expression levels from RNA isolated from the liver after ECRT-122T adenovirus is injected into a rat through a hepatic arterial injection.

Total RNA was extracted from the liver of a rat, and a degree of ribozyme expression was identified by qRT-PCR. As a result, as shown in FIG. 20(*a*), it can be seen that a ribozyme was expressed starting at two days after ECRT-122T injection, and it can be confirmed that only approximately 3.85% of ribozymes were expressed on day 14 after the injection, compared with day 2 after the injection. As also confirmed from the genomic DNA, it can be seen that as shown in FIG. 20(*b*), compared with day 2 after injection, almost all gDNA of the adenovirus had disappeared, leaving approximately 2.23%, in day 14.

From the above-mentioned result, it can be seen that the in vivo distributions of the ECRT-122T adenovirus in the body show a similar pattern regardless of intravenous injection or intraarterial injection, and by day 14 after the injection, almost all of the viral DNA had disappeared.

EXPERIMENTAL EXAMPLE 8

Confirmation of ECRT-122T Toxicity According to the Performance or Nonperformance of GCV Treatment 8-1. Without GCV Treatment The ECRT-122T adenovirus was injected into normal ICR mice once, and on days 15 and 29 after the injection, AST and ALT levels were measured.

Figure 21A:
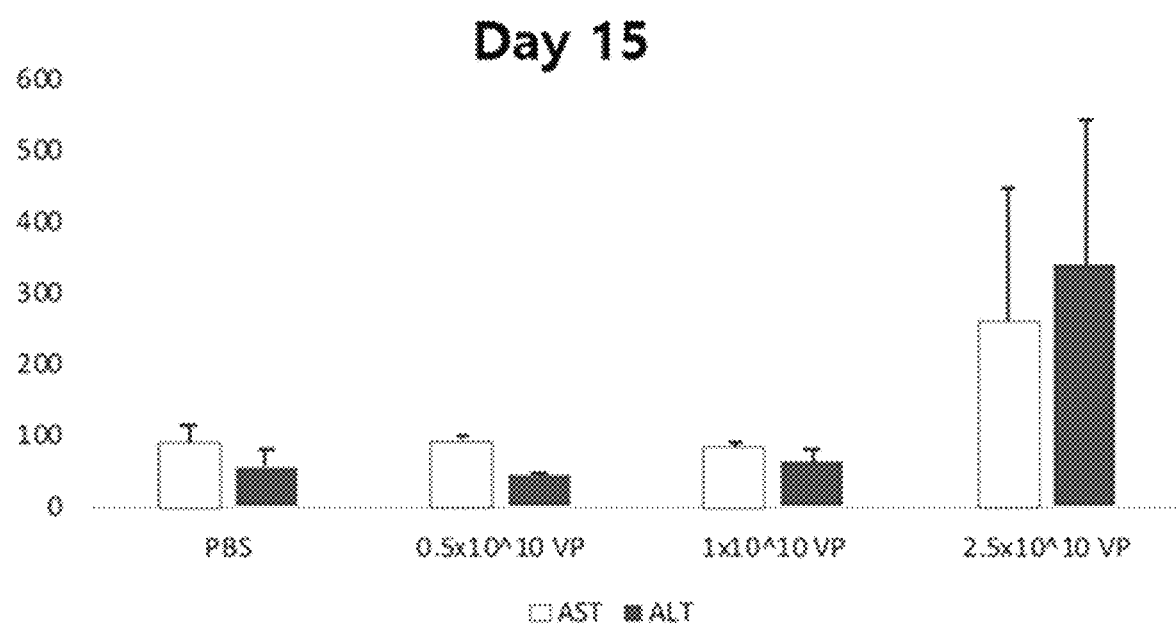
FIG. 21(a) is a graph showing the results of measuring AST and ALT levels 15 days after an injection of ECRT-122T adenovirus into a normal ICR mouse.
Figure 21B:
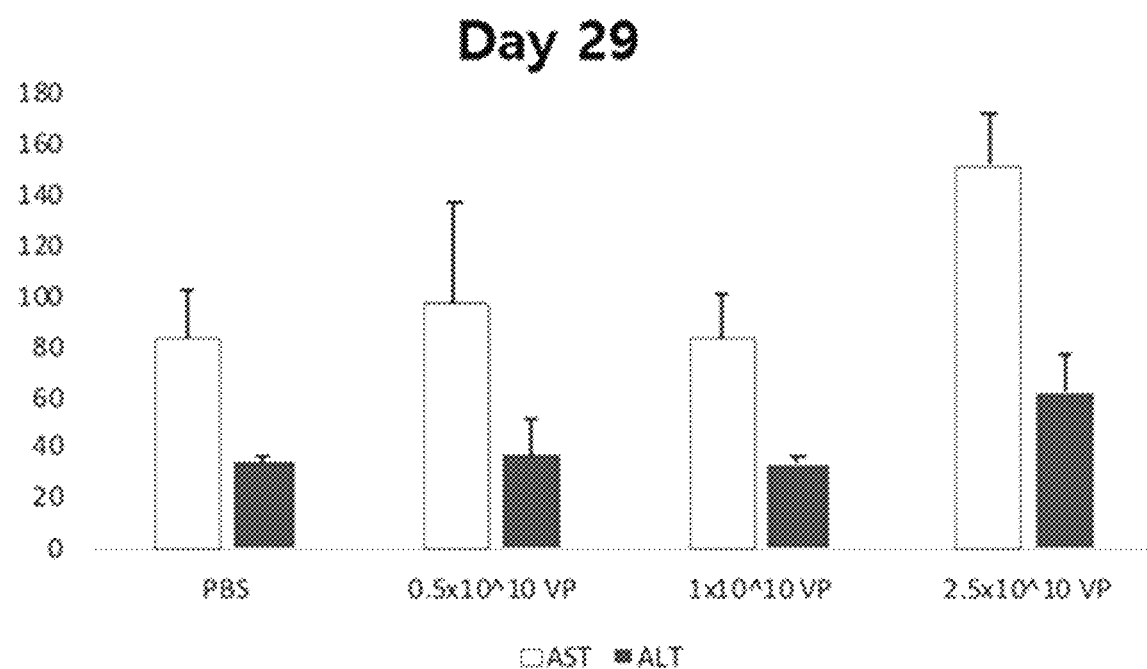
FIG. 21(b) is a graph showing the results of measuring AST and ALT levels 29 days after an injection of ECRT-122T adenovirus into a normal ICR mouse.

As a result, as shown in FIG. 21, it can be seen that weak toxicity was observed in a $2.5 \times 10^{10}$ VP-injected experimental group, and in other experimental groups injected with lower doses, AST and ALT levels were observed to be at a level similar to those of a PBS-injected group, indicating that there was almost no toxicity.

Figure 22A:
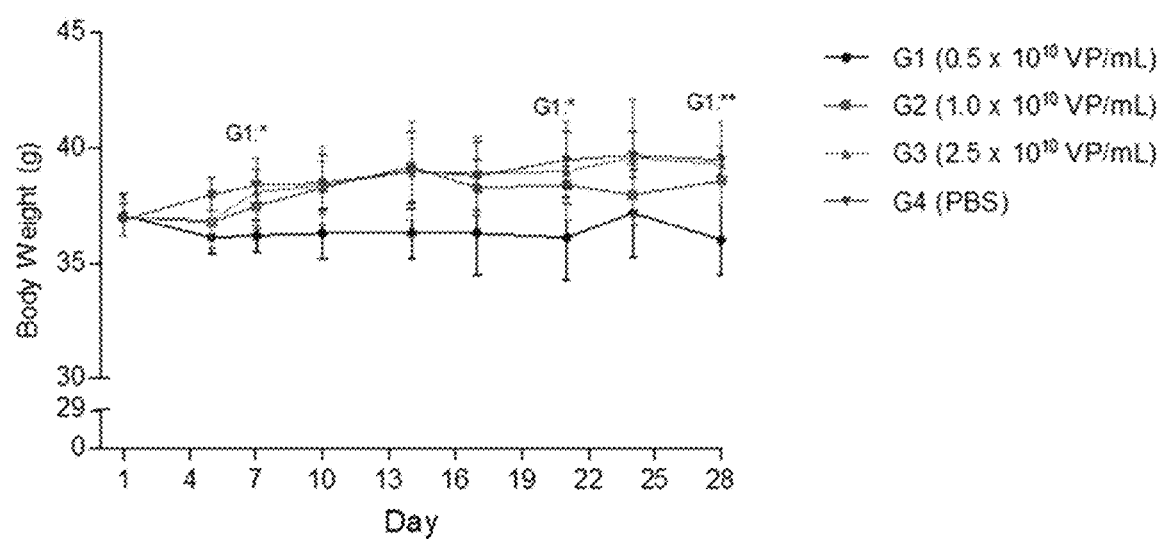
FIG. 22(a) is a graph showing the result of measuring the body weight of a mouse after ECRT-122T adenovirus is injected into a normal ICR mouse.
Figure 22B:
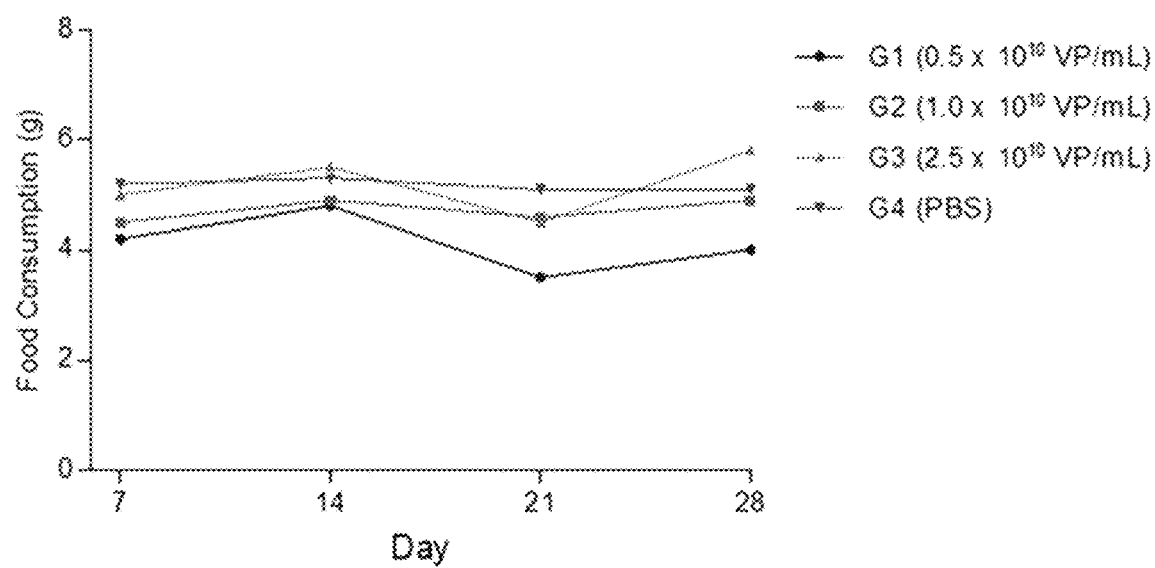
FIG. 22(b) is a graph showing the results of measuring the feed consumption of a mouse after ECRT-122T adenovirus is injected into a normal ICR mouse.
Figure 22C:
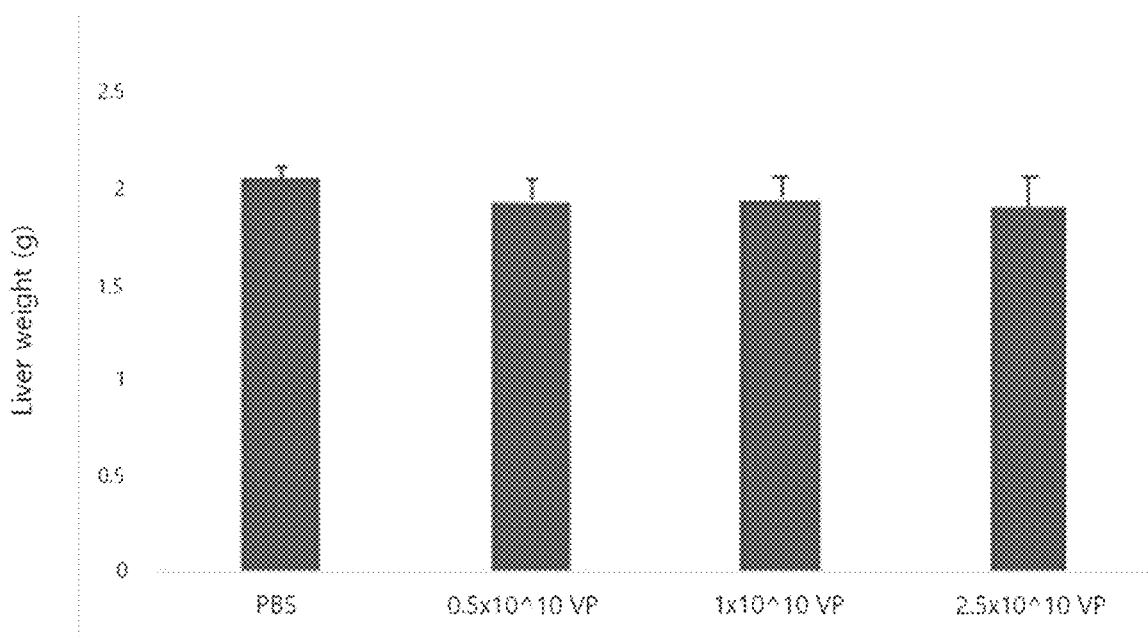
FIG. 22(c) is a graph showing the results of measuring the liver weight of a mouse after ECRT-122T adenovirus is injected into a normal ICR mouse.
Figure 23:
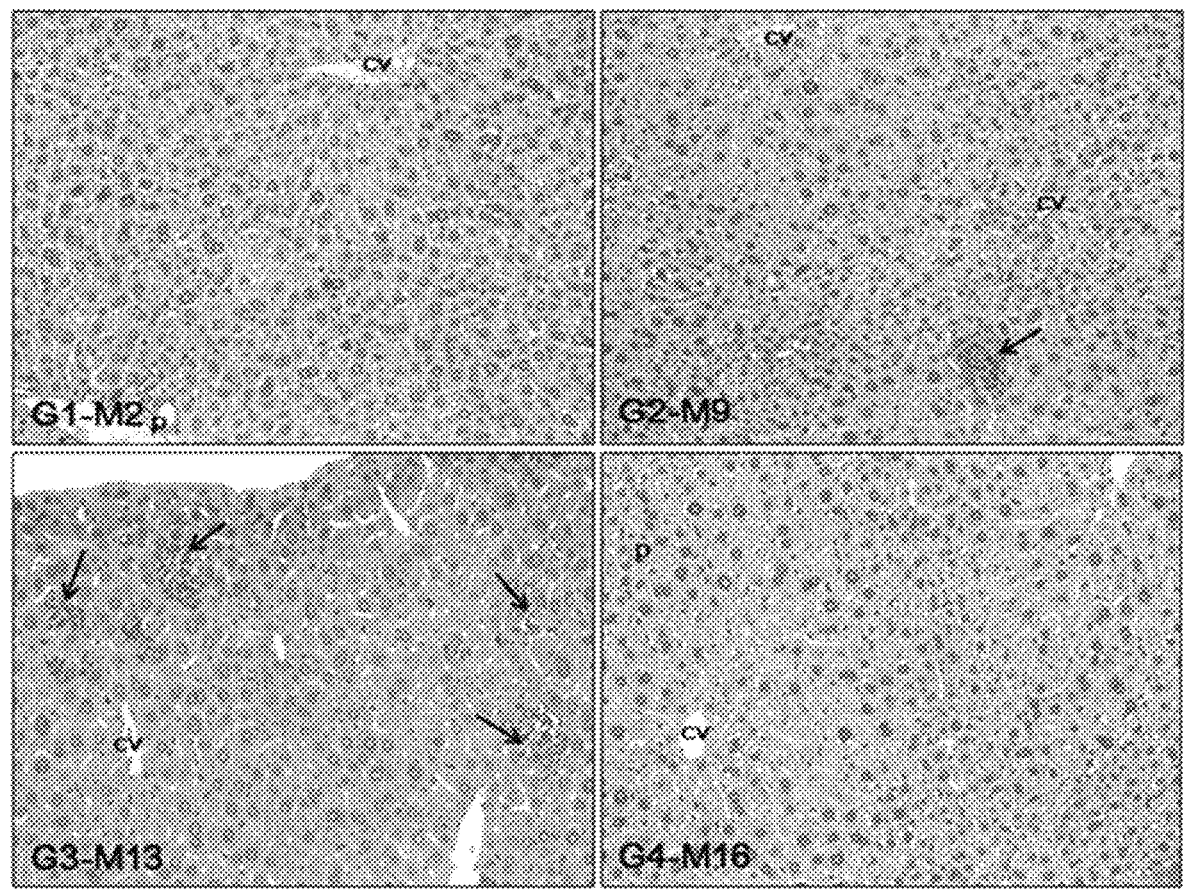
FIG. 23 shows the histopathological examination results for the liver after different doses of the ECRT-122T adenovirus are injected into a normal ICR mouse

In addition, as shown in FIG. 22, it can be confirmed that there were no abnormal findings in terms of body weight, feed consumption, and liver weight of mice during the experiment. From the result of the histopathological examination performed twenty-nine days after the adenovirus was injected intravenously at one instance, as shown in FIG. 23, in the $2.5 \times 10^{10}$ VP-injected experimental group (G3), hepatocellular necrosis (arrow) and inflammation were observed, indicating that minor liver damage occurred. In the $1.0 \times 10^{10}$ VP-injected experimental group (G2), it was confirmed that local inflammatory cell infiltration (arrow) had occurred, but liver damage did not occur. In FIG. 23, cv indicates a central vein, and p indicates a portal area.

The histopathological examination results are summarized in Table 4 below.

TABLE 4

| | Groups | | | |
|---|---|---|---|---|
| Histopathology | G1<br>$0.5 \times 10^{10}$ | G2<br>$1.0 \times 10^{10}$ | G3<br>$2.5 \times 10^{10}$ | G4<br>Vehicle<br>(PBS) |
| No. examined | 4 | 5 | 5 | 5 |
| No specific lesion | 4 (100) | 4 (80) | 0 (0.00) | 5 (100) |
| Inflammatory foci with hepatocyte necrosis | 0 (0.00) | 1 (20.0) | 4 (80.0) | 0 (0.00) |
| Grades: Minimal | 0 | 1 | 3 | 0 |
| Mild | 0 | 0 | 1 | 0 |
| Cell infiltration, mononuclear cells, periductal, focal | 0 (0.00) | 0 (0.00) | 2 (40.0) | 0 (0.00) |
| Grades: Minimal | 0 | 0 | 2 | 0 |

8-2. With GCV Treatment

The ECRT-122T adenovirus was injected into normal ICR mice, and GCV was administered twice a day for 10 days, followed by measuring AST and ALT levels.

Figure 24A:
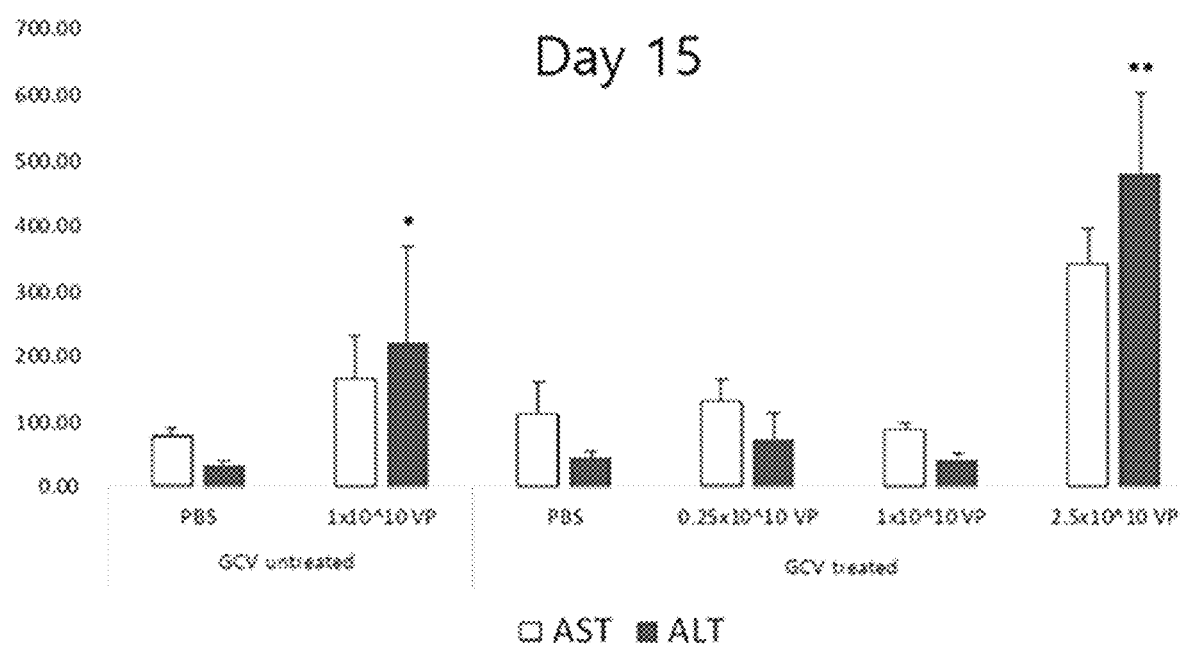
FIG. 24(a) is a graph showing the results of measuring AST and ALT levels 15 days after ECRT-122T adenovirus is injected into a normal ICR mouse and then treated with GCV.
Figure 24B:
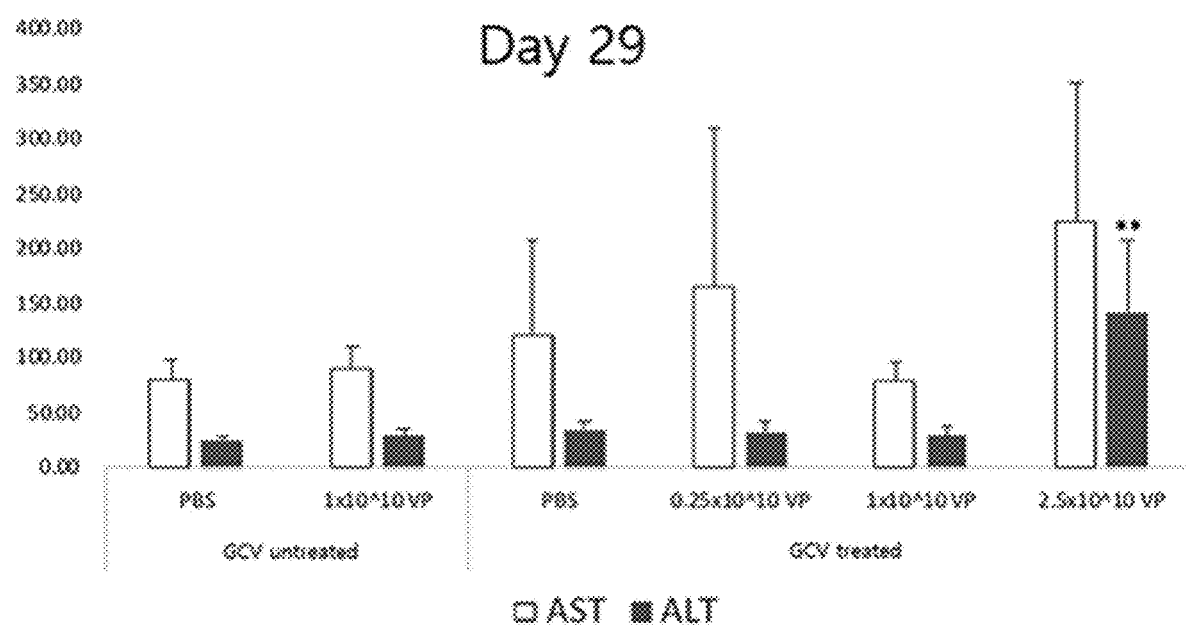
FIG. 24(b) is a graph showing the results of measuring AST and ALT levels 29 days after ECRT-122T adenovirus is injected into a normal ICR mouse and then treated with GCV.

As a result, as shown in FIG. 24, in experimental groups injected at different doses, with the exception of the $2.5 \times 10^{10}$ VP-injected experimental group, AST and ALT levels were observed to be at a level similar to those of a PBS-injected group, indicating that there was almost no toxicity.

Figure 25A:
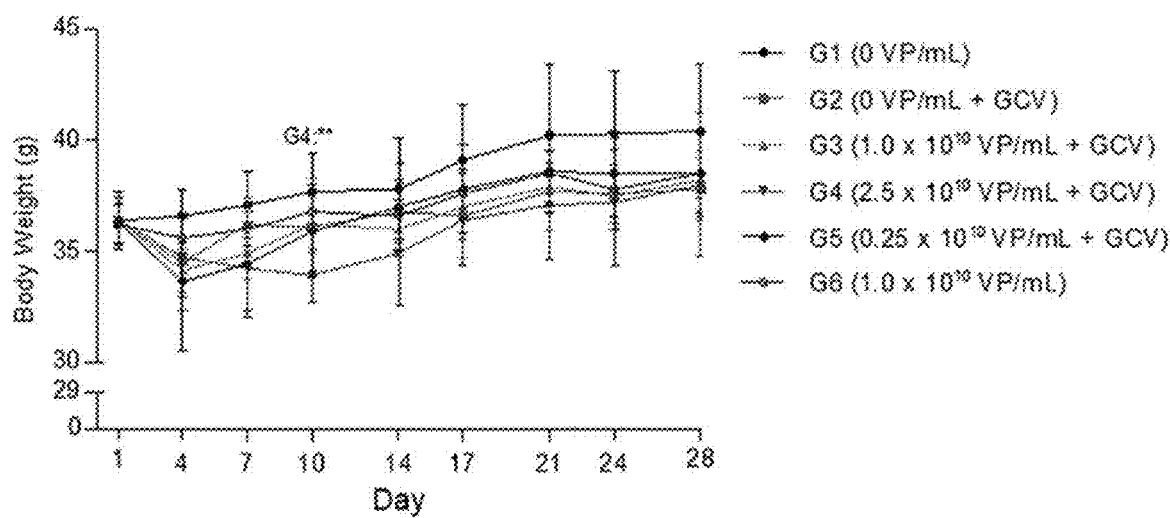
FIG. 25(a) is a graph showing the results of measuring the body weight of a mouse after ECRT-122T adenovirus is injected into a normal ICR mouse and then treated with GCV.
Figure 25B:
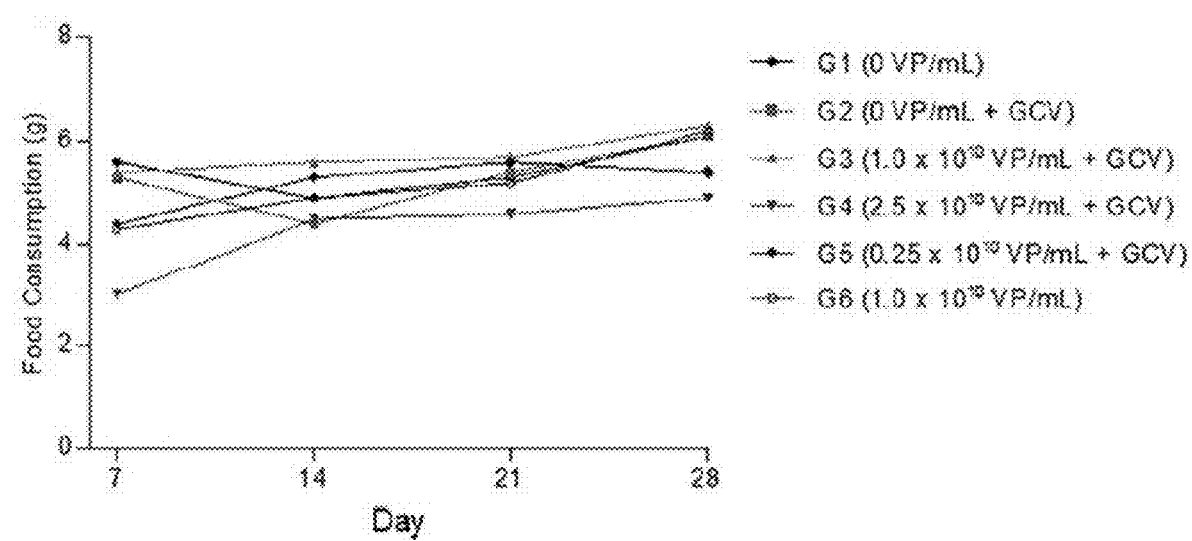
FIG. 25(b) is a graph showing the results of measuring the feed consumption of a mouse after ECRT-122T adenovirus is injected into a normal ICR mouse and then treated with GCV.
Figure 25C:
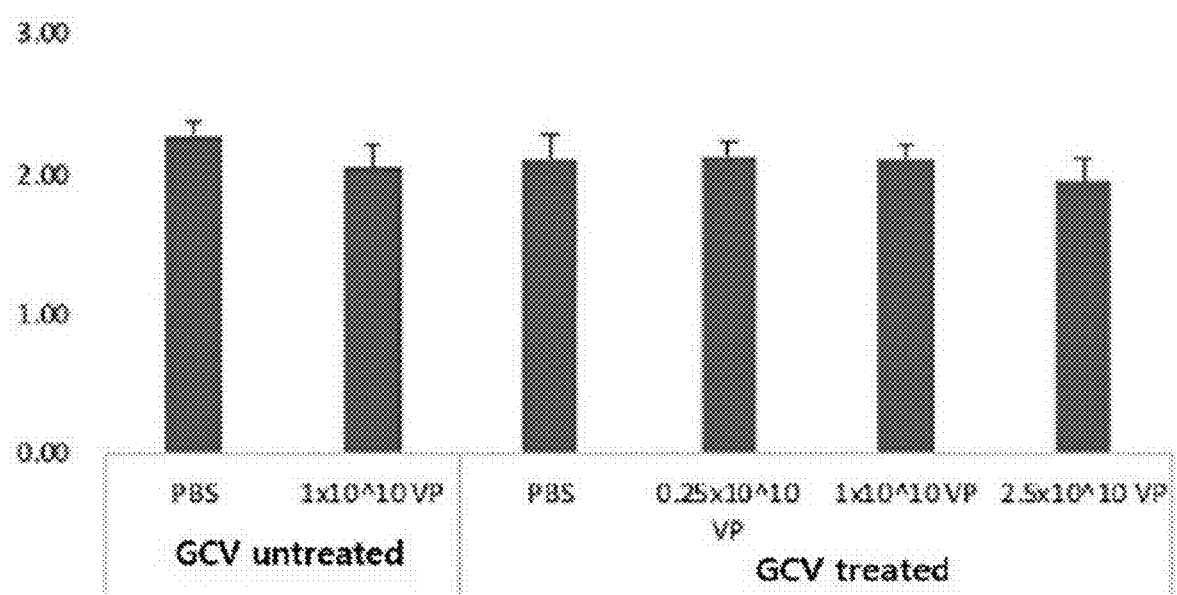
FIG. 25(c) is a graph showing the results of measuring the liver weight of a mouse after ECRT-122T adenovirus is injected into a normal ICR mouse and then treated with GCV.

In addition, as shown in FIGS. 25(*a*) and 25(*b*), it can be confirmed that there were no significant changes in body weight, feed consumption and liver weight of mice during the experiment, and as shown in FIG. 25(*c*), there was no abnormal finding related to liver weight.

Figure 26:
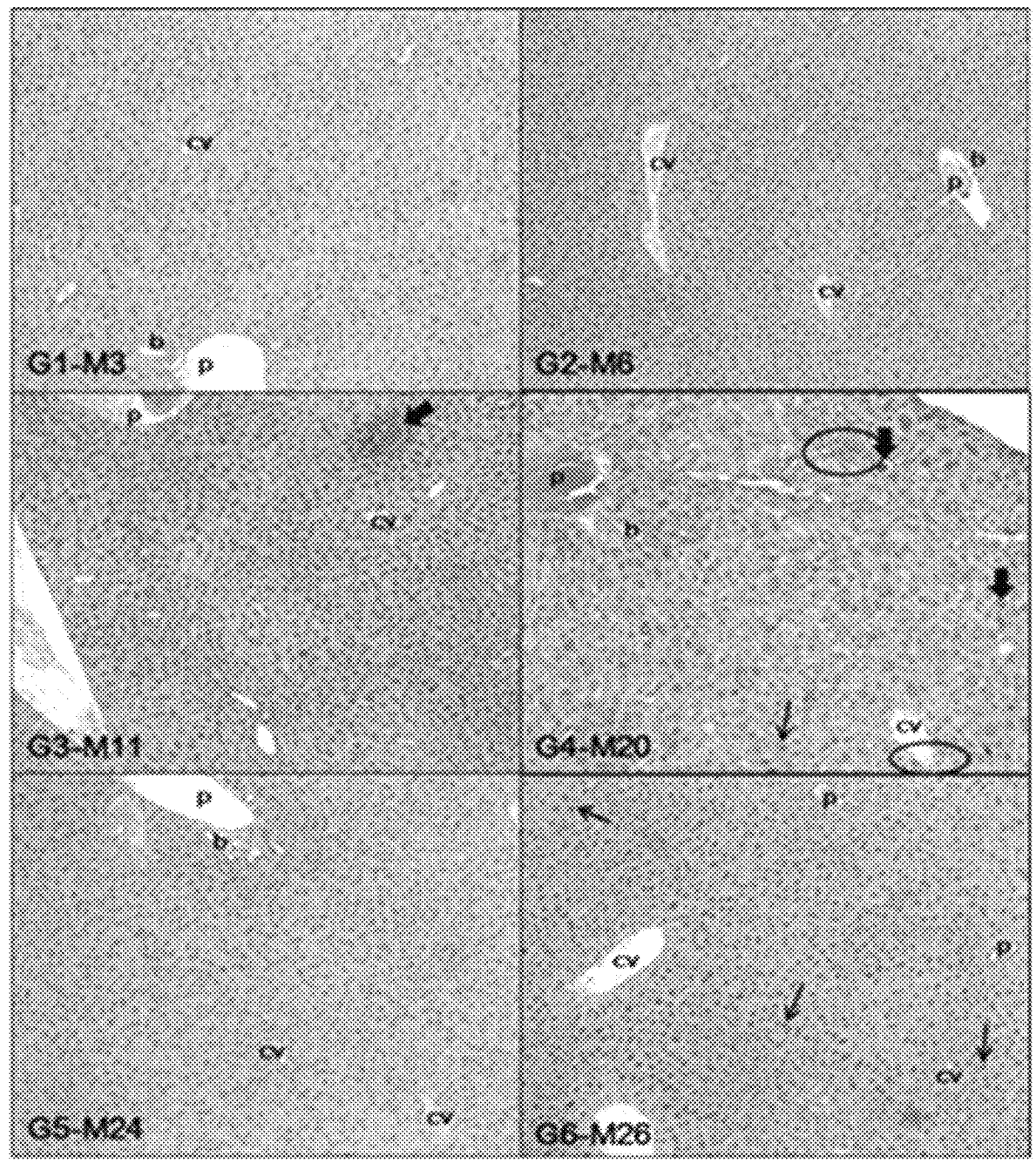
FIG. 26 shows the histopathological examination results for the liver after different doses of the ECRT-122T adenovirus were injected into a normal ICR mouse and then treated with GCV.

According to the histopathological analysis of the liver, as shown in FIG. 26, it can be confirmed that no abnormal findings were observed in the PBS-injected group (G1), the PBS+GCV-administered group (G2) and the $0.25 \times 10^{10}$ VP+GCV-administered group (G5). However, in the $1.0 \times 10^{10}$ VP+GCV-administered group (G3), a local microabscess (thick arrow) formed by neutrophil infiltration was observed, but liver damage did not occur. In the $2.5 \times 10^{10}$ VP+GCV-administered group (G4), enlarged hepatocytes having a large nucleus, necrotic hepatocytes (thick arrow), multiple inflammatory cell infiltration (circle), increased hepatotic mitosis (thick arrow) and lymphatic cell infiltration into the proximity of the bile ductile (b) were observed, indicating the occurrence of liver damage. In G6 not administered with GCV ($1.0 \times 10^{10}$ VP-injected group), the number of mitotic hepatocytes (arrow) slightly increased.

The histopathological examination results are shown in Table 5 below.

TABLE 5

| Histopathology/ Groups | G1 Vehicle (PBS) | G2 PBS + GCV | G3 $1.0 \times 10^{10}$ + GCV | G4 $2.5 \times 10^{10}$ + GCV | G5 $0.25 \times 10^{10}$ + GCV | G6 $1.0 \times 10^{10}$ |
|---|---|---|---|---|---|---|
| No. examined | 5 | 5 | 5 | 5 | 5 | 5 |
| No specific lesion | 5 (100) | 4 (80.0) | 3 (60.0) | 0 (0.00) | 5 (100) | 3 (60.0) |
| Cell infiltration, mononuclear or mixed cells, multifocal | 0 (0.00) | 1 (20.0) | 1 (20.0) | 4 (80.0) | 0 (0.00) | 0 (0.00) |
| Grades: Minimal | 0 | 1 | 1 | 0 | 0 | 0 |
| Mild | 0 | 0 | 0 | 4 | 0 | 0 |
| Microabcess, focal | 0 (0.00) | 0 (0.00) | 1 (20.0) | 0 (0.00) | 0 (0.00) | 0 (0.00) |
| Grades: Minimal | 0 | 0 | 1 | 0 | 0 | 0 |
| Hepatocytomegaly, diffuse | 0 (0.00) | 0 (0.00) | 0 (0.00) | 5 (100) | 0 (0.00) | 0 (0.00) |
| Grades: Minimal | 0 | 0 | 0 | 1 | 0 | 0 |
| Mild | 0 | 0 | 0 | 2 | 0 | 0 |
| Moderate | 0 | 0 | 0 | 2 | 0 | 0 |
| Necrotic hepatocytes | 0 (0.00) | 0 (0.00) | 0 (0.00) | 3 (60.0) | 0 (0.00) | 0 (0.00) |
| Grades: Minimal | 0 | 0 | 0 | 2 | 0 | 0 |
| Mild | 0 | 0 | 0 | 1 | 0 | 0 |
| Hepatocytic mitosis, increased, diffuse | 0 (0.00) | 0 (0.00) | 0 (0.00) | 4 (80.0) | 0 (0.00) | 1 (20.0) |
| Grades: Minimal | 0 | 0 | 0 | 2 | 0 | 1 |
| Mild | 0 | 0 | 0 | 1 | 0 | 0 |
| Moderate | 0 | 0 | 0 | 1 | 0 | 0 |
| Oval cell hyperplasia | 0 (0.00) | 0 (0.00) | 0 (0.00) | 3 (60.0) | 0 (0.00) | 0 (0.00) |
| Grades: Minimal | 0 | 0 | 0 | 3 | 0 | 0 |
| Pericholangitis, (multi)focal | 0 (0.00) | 0 (0.00) | 0 (0.00) | 3 (60.0) | 0 (0.00) | 1 (20.0) |
| Grades: Minimal | 0 | 0 | 0 | 3 | 0 | 1 |

As a result of analyzing AST and ALT levels and examining histopathological findings, when the adenovirus was administered intravenously at a dose of $2.5 \times 10^{10}$ VP/head, and then GCV was administered twice a day for 10 days, hepatocellular necrosis and inflammation occur, resulting in the induction of liver damage. However, when the adenovirus was administered alone at $0.25 \times 10^{10}$ VP/head and $1.0 \times 10^{10}$ VP/head or in combination with GCV, up to day 15 after the administration, liver damage-associated AST and ALT levels increased. However, according to the histological examination performed on day 29, a meaningful toxicological change which would be considered to be related to adenovirus administration was not observed in the liver.

COMPARATIVE EXAMPLE 1

Comparison of Efficacy of CRT-122T and ECRT-122T 1-1. Comparison of Anticancer Efficacy Anticancer efficacy was compared by inducing the generation of liver cancer by injecting $3 \times 10^6$ Hep3B cells into an international standard mouse model and administering an adenovirus including a CRT-122T or ECRT-122T vector to the mouse model. The CRT-122T vector is a type of vector in which a SD/SA sequence and WPRE are removed from the ECRT-122T vector.

Figure 27A:
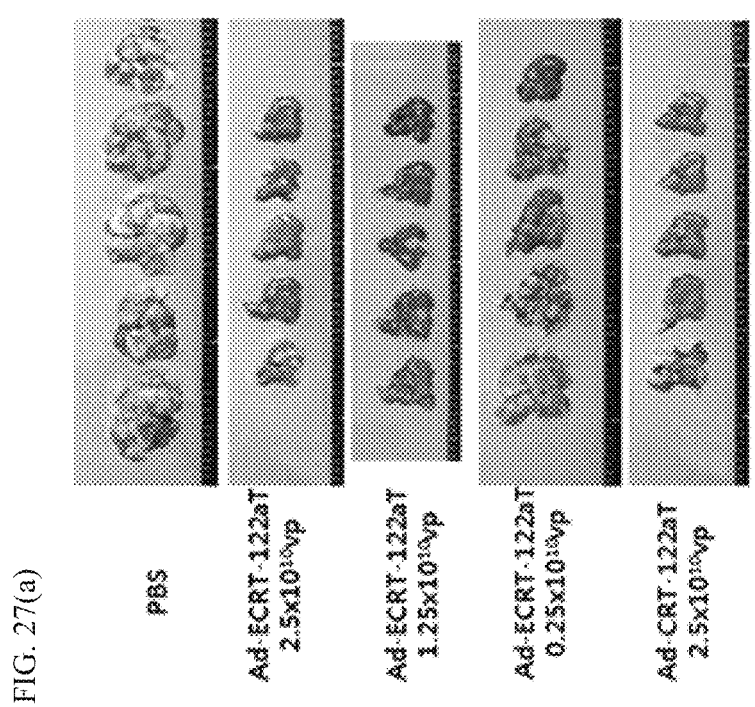
FIG. 27(a) is a photograph showing the results of comparing anticancer efficacy as a result of injecting Hep3B cells into a mouse to induce liver cancer formation, and then administering CRT-122T or ECRT-122T adenovirus.
Figure 27B:
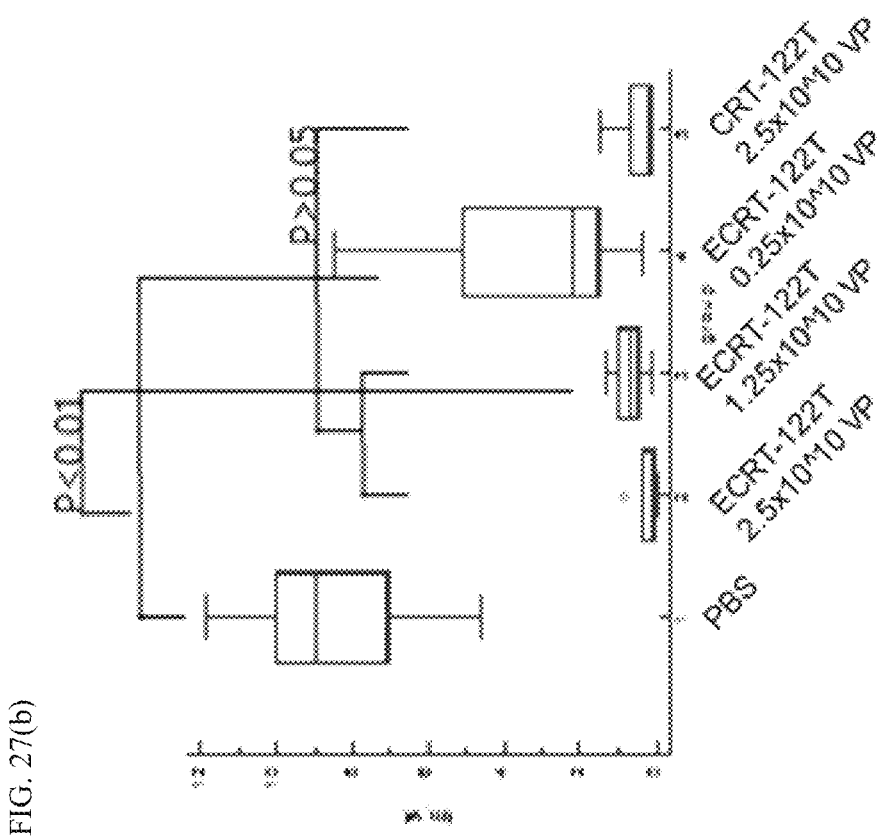
FIG. 27(b) is a graph showing the results of comparing anticancer efficacy as a result of injecting Hep3B cells into a mouse to induce liver cancer formation, and then administering CRT-122T or ECRT-122T adenovirus.

As a result, as shown in FIG. 27, it can be seen that when an adenovirus was injected at $2.5 \times 10^{10}$ VP (virus particle), when compared with CRT-122T, ECRT-122T had superior anticancer efficacy. The anticancer efficacy of CRT-122T was similar to that of ECRT-122T being administered at a dose of $1.25 \times 10^{10}$ VP.

1-2. Comparison of Anticancer Efficacy

Tumorigenesis was induced by injecting SNU398 cells into a mouse xenograft subcutaneous model, and when tumors had grown to a certain size or more, an adenovirus including a CRT-122T or ECRT-122T vector was intratumorally (I.T.) injected a total of two times at a dose of $1 \times 10^9$ VP once every 2 days. After the adenovirus injection, while the mice were being observed, a tumor size and a body weight were measured every three days, and 22 days later, the mice were sacrificed to measure a final tumor size, a liver weight, and aspartate transaminase (AST) and alanine transaminase (ALT) levels.

Figure 28A:
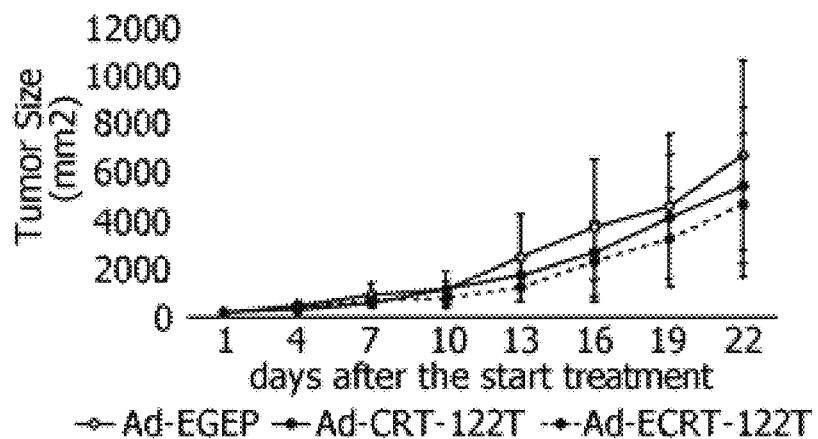
FIG. 28(a) is a graph showing the results of measuring the tumor sizes after administration of CRT-122T or ECRT-122T adenovirus into a mouse xenograft subcutaneous model in which tumorigenesis is induced.
Figure 28B:
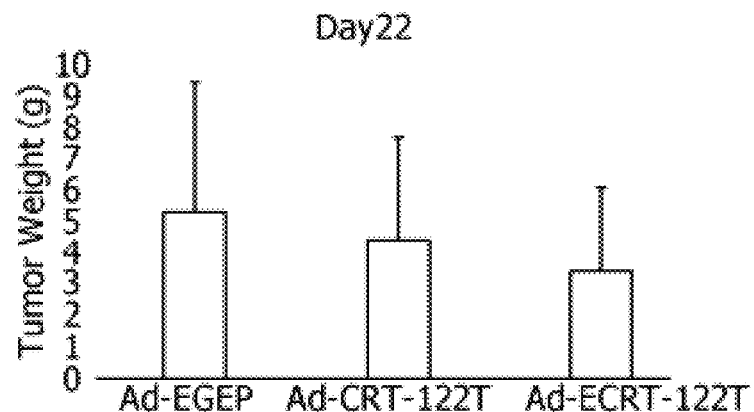
FIG. 28(b) is a graph showing the results of measuring the tumor weight after administration of CRT-122T or ECRT-122T adenovirus into a mouse xenograft subcutaneous model in which tumorigenesis is induced.
Figure 28C:
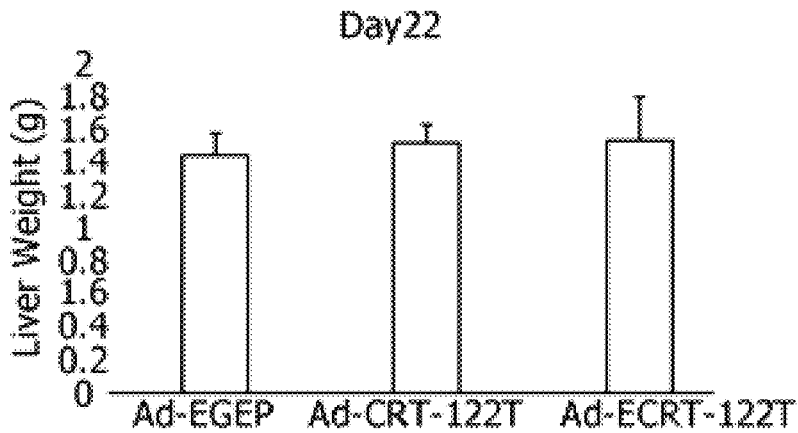
FIG. 28(c) is a graph showing the results of measuring the liver weight after administration of CRT-122T or ECRT-122T adenovirus into a mouse xenograft subcutaneous model in which tumorigenesis is induced.
Figure 28D:
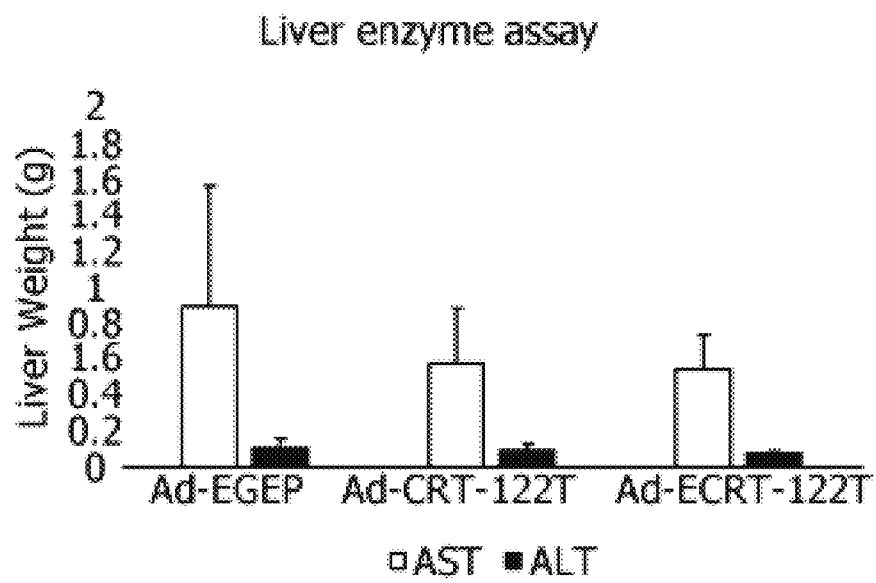
FIG. 28(d) is a graph showing the results of measuring AST and ALT levels after administration of CRT-122T or ECRT-122T adenovirus into a mouse xenograft subcutaneous model in which tumorigenesis is induced.
Figure 28E:
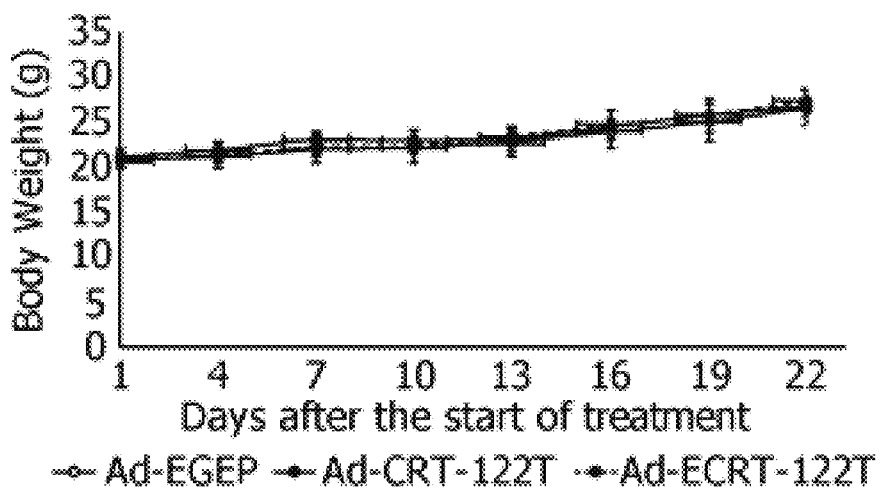
FIG. 28(e) is a graph showing the results of measuring the body weight after administration of CRT-122T or ECRT-122T adenovirus into a mouse xenograft subcutaneous model in which tumorigenesis is induced.

As a result, as shown in FIGS. 28(a) and 28(b), it can be confirmed that compared with CRT-122T, ECRT-122T had superior anticancer efficacy. There was no significant difference in the body weight and liver weight of mice between experimental groups, and the AST and ALT levels indicated that the adenovirus did not induce hepatotoxicity (FIGS. 28(c) to 28(e)).

According to the above-described result, it was confirmed that a sufficient anticancer effect can be obtained by injecting only a small dose of the adenovirus, and compared with CRT-122T, it can be seen that ECRT-122T had significantly superior anticancer efficacy.

1-3. Comparison of Toxicity

To confirm toxicity according to an injection dose of the adenovirus, the ECRT or ECRT-122T adenovirus was injected into normal ICR mice, and on days 2, 7 and 14 after injection, AST and ALT levels were measured.

Figure 29:
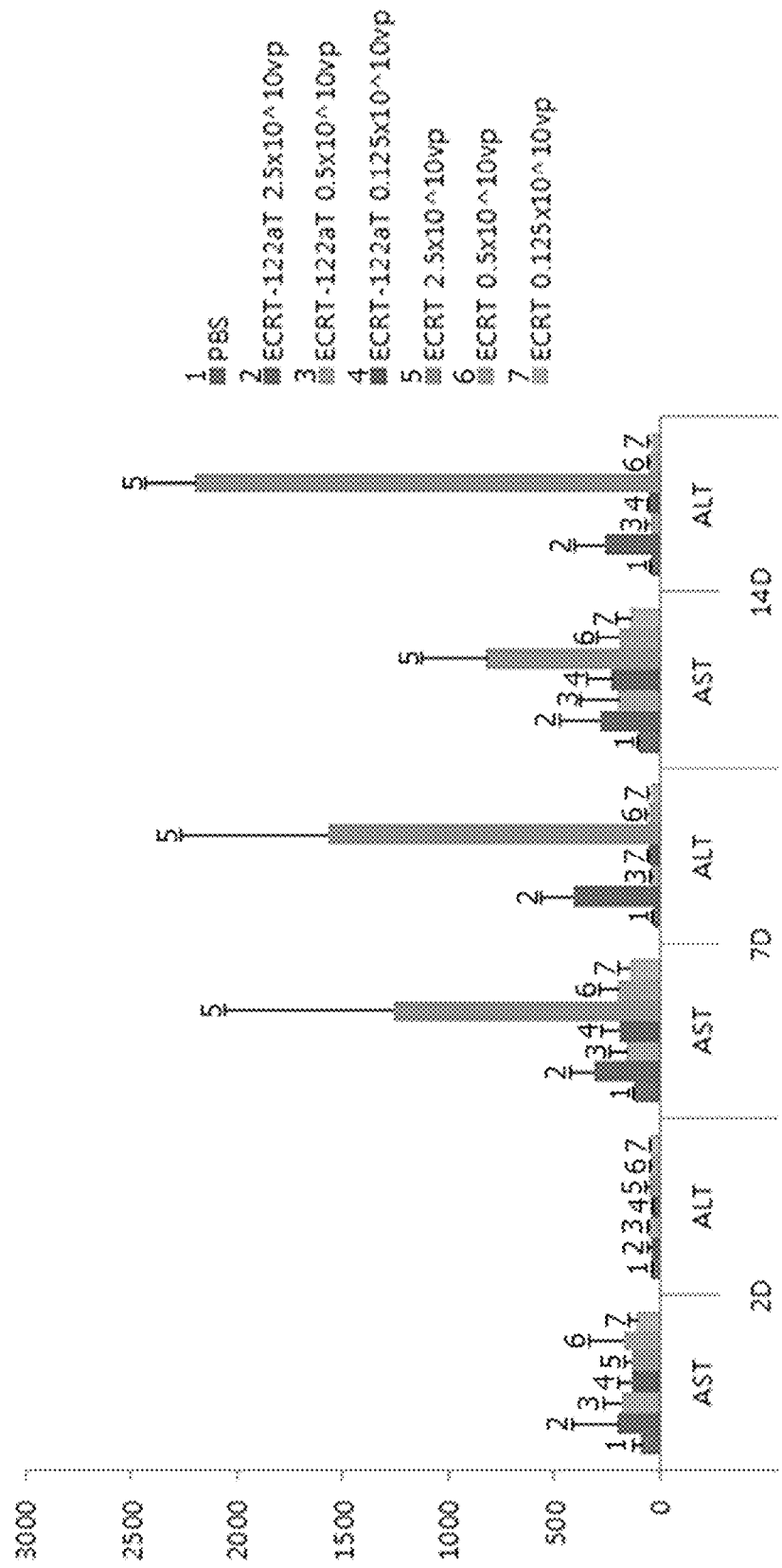
FIG. 29 is a graph showing the results of measuring AST and ALT levels after ECRT or ECRT-122T adenovirus is injected into a normal ICR mouse.

As a result, as shown in FIG. 29, in the mouse administered with ECRT at a dose of $2.5 \times 10^{10}$ VP, very high hepatotoxicity was maintained until day 14 after the injection, but in the mouse administered with ECRT-122T at a dose of 2.5×10$^{10}$ VP, hepatotoxicity was very low in comparison to the ECRT-administered mouse.

Since a trans-splicing ribozyme according to an embodiment of the invention does not act on normal tissue, but is specifically expressed in cancer tissue, it is very safe and has excellent expression efficiency at the post-transcription level, and thus can be effectively used in treatment of cancer. Specifically, due to having a CMV promoter and SD/SA and WPRE sequences, a recombinant vector of an embodiment of the invention can have high ribozyme expression efficiency, and due to miR-122T, the recombinant vector can regulate activity through miR-122 and thus have excellent safety. Therefore, the recombinant vector of an embodiment of the invention can be effectively used in treatment of all types of liver cancer, except some types caused by HCV in which miR-122 expression in cancer tissue is highly shown in comparison to normal tissue, and the recombinant vector of an embodiment of the invention also can be effectively used in treatment of other types of cancer in which miR-122 is not substantially expressed.

It will be apparent to those skilled in the art that various modifications can be made to the above-described exemplary embodiments of an embodiment of the invention without departing from the spirit or scope of the invention. Thus, it is intended that an embodiment of the invention covers all such modifications provided they come within the scope of the appended claims and their equivalents.

What is claimed is:

1. A nucleic acid construct, comprising, in the order from 5' end to 3' end:
   (i) a cytomegalovirus (CMV) promoter;
   (ii) a splicing donor/splicing acceptor sequence (SD/SA sequence);
   (iii) a ribozyme-desired gene expression cassette, which is operably linked to the CMV promoter (i), includes (a) a sequence encoding a trans-splicing ribozyme targeting a cancer-specific gene and (b) a target gene connected to a 3' exon of the ribozyme-encoding sequence;
   (iv) a Woodchuck hepatitis virus posttranscriptional regulatory element (WPRE); and
   (v) a nucleic acid sequence complementary to microRNA-122 (miR-122), said nucleic acid sequence (v) being connected to the 3' end of the WPRE and comprising one or more copies of the nucleic acid sequence of SEQ ID NO: 5,
   wherein the SD/SA sequence is connected to the 5' end of the ribozyme-desired gene expression cassette, and the WPRE is connected to the 3' end of the ribozyme-desired gene expression cassette, and
   wherein the cancer-specific gene is a telomerase reverse transcriptase (TERT) mRNA sequence.

2. The nucleic acid construct of claim 1, wherein the TERT mRNA sequence comprises the nucleic acid sequence of SEQ ID NO: 2.

3. The nucleic acid construct of claim 1, wherein the trans-splicing ribozyme comprises the nucleic acid sequence of SEQ ID NO: 3.

4. The nucleic acid construct of claim 1, wherein the desired gene is an anti-cancer therapeutic gene or a reporter gene.

5. The nucleic acid construct of claim 4, wherein the anti-cancer therapeutic gene is selected from the group consisting of a drug-sensitizing gene, a proapoptotic gene, a cytostatic gene, a cytotoxic gene, a tumor suppressor gene, an antigenic gene, a cytokine gene and an anti-angiogenic gene.

6. The nucleic acid construct of claim 5, wherein the drug-sensitizing gene is a herpes simplex virus thymidine kinase (HSVtk) gene.

7. The nucleic acid construct of claim 6, wherein the HSVtk gene comprises the nucleic acid sequence of SEQ ID NO: 4.

8. The nucleic acid construct of claim 4, wherein the reporter gene is luciferase, a green fluorescent protein (GFP), a modified green fluorescent protein (mGFP), an enhanced green fluorescent protein (EGFP), a red fluorescent protein (RFP), a modified red fluorescent protein (mRFP), an enhanced red fluorescent protein (ERFP), a blue fluorescent protein (BFP), an enhanced blue fluorescent protein (EBFP), a yellow fluorescent protein (YFP), an enhanced yellow fluorescent protein (EYFP), a cyan fluorescent protein (CFP) or an enhanced cyan fluorescent protein (ECFP).

9. A gene delivery system comprising the nucleic acid construct of claim 1.

10. A ribozyme expressed from the nucleic acid construct of claim 1.

11. A pharmaceutical composition, comprising the nucleic acid construct of claim 1, a gene delivery system comprising the nucleic acid construct, or a ribozyme expressed from the nucleic acid construct as an active ingredient.

12. The pharmaceutical composition of claim 11, wherein the pharmaceutical composition is in a formulation suitable for administration by intravenous, intraartery, intratumor, or subcutaneous route.

13. The pharmaceutical composition of claim 11, wherein the pharmaceutical composition is in a formulation suitable for injection or infusion.

14. A method for treating cancer in a subject in need thereof, comprising administering to the subject an effective amount of a pharmaceutical composition comprising the nucleic acid construct claim 1, a gene delivery system comprising the nucleic acid construct, or a ribozyme expressed from the nucleic acid construct as an active ingredient,
wherein the cancer is liver cancer or glioblastoma.

15. The method of claim 14, wherein, in cancer tissue of the subject, a copy number of miR-122 expressed in a cancer tissue is less than 100 times a copy number of ribozymes expressed from the nucleic acid construct in the cancer tissue.

16. The method of claim 14, wherein, in cancer tissue of the subject, miR-122 is substantially not expressed in cancer tissue.

17. The method of claim 14, wherein the liver cancer is caused by any one or more selected from the group consisting of hepatitis B virus, hepatitis C virus decreasing miR-122 expression in liver cancer tissue, alcohol, chronic hepatitis, liver cirrhosis, non-alcoholic fatty acid disease, aflatoxin, and family history.

\* \* \* \* \*

SEQUENCE LISTING

```
<160> NUMBER OF SEQ ID NOS: 11

<210> SEQ ID NO 1
<211> LENGTH: 255
<212> TYPE: DNA
<213> ORGANISM: Artificial Sequence
<220> FEATURE:
<223> OTHER INFORMATION: CMV promoter sequence

<400> SEQUENCE: 1
gacattgatt attgactagt tattaatagt aatcaattac ggggtcatta gttcatagcc     60
catatatgga gttccgcgtt acataactta cggtaaatgg cccgcctggc tgaccgccca    120 acgaccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgc                                                    255

<210> SEQ ID NO 2
<211> LENGTH: 4018
<212> TYPE: DNA
<213> ORGANISM: Artificial Sequence
<220> FEATURE:
<223> OTHER INFORMATION: hTERT mRNA sequence

<400> SEQUENCE: 2
caggcagcgc tgcgtcctgc tgcgcacgtg ggaagccctg gccccggcca ccccgcgat     60 gccgcgcgct ccccgctgcc gagccgtgcg ctccctgctg cgcagccact accgcgaggt    120
gctgccgctg gccacgttcg tgcggcgcct ggggcccag ggctggcggc tggtgcagcg    180
cggggacccg gcggctttcc gcgcgctggt ggcccagtgc ctggtgtgcg tgccctggga    240
cgcacggccg cccccgccg ccccctcctt ccgccaggtg tcctgcctga aggagctggt    300
ggcccgagtg ctgcagaggc tgtgcgagcg cggcgcgaag aacgtgctgg ccttcggctt    360
cgcgctgctg gacggggccc gcggggggccc cccgaggcc ttcaccacca gcgtgcgcag    420
ctacctgccc aacacggtga ccgacgcact gcgggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggccccgc cacacgctag tggaccccga aggcgtctgg gatgcgaacg    660
ggcctggaac catagcgtca gggaggccgg ggtcccctg ggcctgccag ccccgggtgc    720
gaggaggcgc gggcagtg ccagccgaag tctgccgttg cccaagaggc ccaggcgtgg    780
cgctgcccct gagccggagc ggacgcccgt tgggcagggg tcctgggccc acccgggcag    840
```

```
gacgcgtgga ccgagtgacc gtggtttctg tgtggtgtca cctgccagac ccgccgaaga      900
agccacctct ttggagggtg cgctctctgg cacgcgccac tcccacccat ccgtgggccg      960
ccagcaccac gcgggccccc catccacatc gcggccacca cgtccctggg acacgccttg     1020
tcccccggtg tacgccgaga ccaagcactt cctctactcc tcaggcgaca aggagcagct     1080
gcggccctcc ttcctactca gctctctgag gcccagcctg actggcgctc ggaggctcgt     1140
ggagaccatc tttctggggtt ccaggccctg gatgccaggg actccccgca ggttgccccg     1200
cctgccccag cgctactggc aaatgcggcc cctgtttctg gagctgcttg gaaccacgc      1260 gcagtgcccc tacggggtgc tcctcaagac gcactgcccg ctgcgagctg cggtcacccc     1320
agcagccggt gtctgtgccc gggagaagcc ccagggctct gtggcggccc ccgaggagga     1380
ggacacagac ccccgtcgcc tggtgcagct gctccgccag cacagcagcc cctggcaggt     1440
gtacggcttc gtgcgggcct gcctgcgccg gctggtgccc ccaggcctct ggggctccag     1500
gcacaacgaa cgccgcttcc tcaggaacac caagaagttc atctccctgg ggaagcatgc     1560
caagctctcg ctgcaggagc tgacgtggaa gatgagcgtg cgggactgcg cttggctgcg     1620
caggagccca ggggttggct gtgttccggc cgcagagcac cgtctgcgtg aggagatcct     1680
ggccaagttc ctgcactggc tgatgagtgt gtacgtcgtc gagctgctca ggtctttctt     1740
ttatgtcacg gagaccacgt ttcaaaagaa caggctcttt ttctaccgga agagtgtctg     1800
gagcaagttg caaagcattg gaatcagaca gcacttgaag agggtgcagc tgcgggagct     1860
gtcggaagca gaggtcaggc agcatcggga agccaggccc gccctgctga cgtccagact     1920
ccgcttcatc cccaagcctg acgggctgcg gccgattgtg aacatggact acgtcgtggg     1980
agccagaacg ttccgcagag aaaagagggc cgagcgtctc acctcgaggg tgaaggcact     2040
gttcagcgtg ctcaactacg agcgggcgcg gcgccccggc ctcctgggcg cctctgtgct     2100
gggcctggac gatatccaca gggcctggcg caccttcgtg ctgcgtgtgc gggcccagga     2160
cccgccgcct gagctgtact ttgtcaaggt ggatgtgacg ggcgcgtacg acaccatccc     2220
ccaggacagg ctcacggagg tcatcgccag catcatcaaa ccccagaaca cgtactgcgt     2280
gcgtcggtat gccgtggtcc agaaggccgc ccatgggcac gtccgcaagg ccttcaagag     2340
ccacgtctct accttgacag acctccagcc gtacatgcga cagttcgtgg ctcacctgca     2400
ggagaccagc ccgctgaggg atgccgtcgt catcgagcag agctcctccc tgaatgaggc     2460
cagcagtggc ctcttcgacg tcttcctacg cttcatgtgc caccacgccg tgcgcatcag     2520
gggcaagtcc tacgtccagt gccaggggat cccgcagggc tccatcctct ccacgctgct     2580
ctgcagcctg tgctacggcg acatggagaa caagctgttt gcggggattc ggcgggacgg     2640
gctgctcctg cgtttggtgg atgatttctt gttggtgaca cctcacctca cccacgcgaa     2700
aaccttcctc aggaccctgg tccgaggtgt ccctgagtat ggctgcgtgg tgaacttgcg     2760
gaagacagtg gtgaacttcc ctgtagaaga cgaggccctg ggtggcacgg cttttgttca     2820
gatgccggcc cacggcctat tcccctggtg cggcctgctg ctggataccc ggaccctgga     2880
ggtgcagagc gactactcca gctatgcccg gacctccatc agagccagtc tcaccttcaa     2940
ccgcggcttc aaggctggga ggaacatgcg tcgcaaactc tttggggtct gcggctgaa      3000 gtgtcacagc ctgtttctgg atttgcaggt gaacagcctc cagacggtgt gcaccaacat     3060
ctacaagatc ctcctgctgc aggcgtacag gtttcacgca tgtgtgctgc agctcccatt     3120
tcatcagcaa gtttggaaga accccacatt tttcctgcgc gtcatctctg acacggcctc     3180
cctctgctac tccatcctga aagccaagaa cgcagggatg tcgctggggg ccaagggcgc     3240
```

```
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga ggggggggcg    3540
gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag cttttcctca ccaggagccc ggcttccact ccccacatag aatagtcca     3780 tccccagatt cgccattgtt cacccctcgc cctgccctcc tttgccttcc acccccacca    3840
tccaggtgga gaccctgaga aggaccctgg gagctctggg aatttggagt gaccaaaggt    3900
gtgccctgta cacaggcgag gaccctgcac ctggatgggg gtccctgtgg gtcaaattgg    3960
ggggaggtgc tgtgggagta aaatactgaa tatatgagtt tttcagtttt gaaaaaaa     4018
```

<210> SEQ ID NO 3
<211> LENGTH: 393
<212> TYPE: DNA
<213> ORGANISM: Artificial Sequence
<220> FEATURE:
<223> OTHER INFORMATION: hTERT targeting trans-splicing ribozyme

<400> SEQUENCE: 3

```
ggcaggaaaa gttatcaggc atgcacctgg tagctagtct ttaaaccaat agattgcatc      60
ggtttaaaag gcaagaccgt caaattgcgg gaaaggggtc aacagccgtt cagtaccaag     120
tctcagggga aactttgaga tggccttgca aagggtatgg taataagctg acggacatgg     180
tcctaaccac gcagccaagt cctaagtcaa cagatcttct gttgatatgg atgcagttca     240
cagactaaat gtcggtcggg aagatgtgta tcttctcata agatatagtc ggacctctcc     300
ttaatgggag ctagcggatg aagtgatgca acactggagc cgctgggaac taatttgtat     360
gcgaaagtat attgattagt tttggagtac tcg                                  393
```

<210> SEQ ID NO 4
<211> LENGTH: 1131
<212> TYPE: DNA
<213> ORGANISM: Artificial Sequence
<220> FEATURE:
<223> OTHER INFORMATION: Hsv-tk

<400> SEQUENCE: 4

```
atggcttcgt accctgcca tcaacacgcg tctgcgttcg accaggctgc gcgttctcgc       60
ggccatagca accgacgtac ggcgttgcgc cctcgccggc agcaagaagc cacggaagtc     120
cgcctggagc agaaaatgcc cacgctactg cgggtttata tagacggtcc tcacgggatg     180
gggaaaacca ccaccacgca actgctggtg gccctgggtt cgcgcgacga tatcgtctac     240
gtacccgagc cgatgactta ctggcaggtg ctggggggctt ccgagacaat cgcgaacatc     300
tacaccacac aaccaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccgcgccct caccctcatc     480
ttcgaccgcc atcccatcgc cgccctcctg tgctacccgg ccgcgcgata ccttatgggc     540
```

```
agcatgaccc cccaggccgt gctggcgttc gtggccctca tcccgccgac cttgcccggc    600
acaaacatcg tgttgggggc ccttccggag gacagacaca tcgaccgcct ggccaaacgc    660
cagcgccccg gcgagcggct tgacctggct atgctggccg cgattcgccg cgtttacggg    720
ctgcttgcca atacggtgcg gtatctgcag ggcggcgggt cgtggcggga ggattgggga    780
cagctttcgg ggacggccgt gccgccccag ggtgccgagc cccagagcaa cgcgggccca    840
cgaccccata tcggggacac gttatttacc ctgtttcggg cccccgagtt gctgccccc     900 aacggcgacc tgtacaacgt gtttgcctgg gccttggacg tcttggccaa acgcctccgt    960
cccatgcacg tctttatcct ggattacgac caatcgcccg ccggctgccg ggacgccctg   1020
ctgcaactta cctccgggat ggtccagacc cacgtcacca ccccggctc cataccgacg    1080 atctgcgacc tggcgcgcac gtttgcccgg gagatggggg aggctaactg a            1131

<210> SEQ ID NO 5
<211> LENGTH: 22
<212> TYPE: DNA
<213> ORGANISM: Artificial Sequence
<220> FEATURE:
<223> OTHER INFORMATION: miR-122T

<400> SEQUENCE: 5
caaacaccat tgtcacactc ca                                              22

<210> SEQ ID NO 6
<211> LENGTH: 181
<212> TYPE: DNA
<213> ORGANISM: Artificial Sequence
<220> FEATURE:
<223> OTHER INFORMATION: SD/SA sequence

<400> SEQUENCE: 6
agatctgaac tgaaaaacca gaaagttaac tggtaagttt agtcttttg tcttttattt      60 caggtccccgg atccggtggt ggtgcaaatc aaagaactgc tcctcagtgg atgttgcctt   120
tacttctagg cctgtacgga agtgttactt ctgctctaaa agctgcggaa ttgtacccag    180
g                                                                    181

<210> SEQ ID NO 7
<211> LENGTH: 589
<212> TYPE: DNA
<213> ORGANISM: Artificial Sequence
<220> FEATURE:
<223> OTHER INFORMATION: WPRE sequence

<400> SEQUENCE: 7
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttcgctttt cccctccct    300 attgccacgg cggaactcat cgccgcctgc cttgcccgct gctggacagg gctcggctg    360 ttgggcactg acaattccgt ggtgttgtcg gggaaatcat cgtcctttcc ttggctgctc   420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

```
<210> SEQ ID NO 8
<211> LENGTH: 326
<212> TYPE: DNA
<213> ORGANISM: Artificial Sequence
<220> FEATURE:
<223> OTHER INFORMATION: ribozyme antisense sequence

<400> SEQUENCE: 8
aaggccagca cgttcttcgc gccgcgctcg cacagcctct gcagcactcg ggccaccagc      60
tccttcaggc aggacacctg gcggaaggag ggggcggcgg ggggcggccg tgcgtcccag     120
ggcacgcaca ccaggcactg ggccaccagc gcgcggaaag ccgccgggtc cccgcgctgc     180
accagccgcc agccctgggg ccccaggcgc cgcacgaacg tggccagcgg cagcacctcg     240
cggtagtggc tgcgcagcag ggagcgcacg gctcggcagc ggggagcgcg cggcatcgcg     300
ggggtggccg gggccagggc ttccca                                          326

<210> SEQ ID NO 9
<211> LENGTH: 56
<212> TYPE: DNA
<213> ORGANISM: Artificial Sequence
<220> FEATURE:
<223> OTHER INFORMATION: Beta-globin poly(A) signal

<400> SEQUENCE: 9
aataaaggaa atttattttc attgcaatag tgtgttggaa ttttttgtgt ctctca          56

<210> SEQ ID NO 10
<211> LENGTH: 22
<212> TYPE: DNA
<213> ORGANISM: Artificial Sequence
<220> FEATURE:
<223> OTHER INFORMATION: ribozyme forward primer

<400> SEQUENCE: 10
ttccggagga cagacacatc ga                                               22

<210> SEQ ID NO 11
<211> LENGTH: 22
<212> TYPE: DNA
<213> ORGANISM: Artificial Sequence
<220> FEATURE:
<223> OTHER INFORMATION: ribozyme reverse primer

<400> SEQUENCE: 11
gcagataccg caccgtattg gc                                               22
```